(12) United States Patent
Ochiai et al.

(10) Patent No.: US 9,708,413 B2
(45) Date of Patent: Jul. 18, 2017

(54) GLYCOSYLATED LINKER, COMPOUND CONTAINING GLYCOSYLATED LINKER MOIETY AND PHYSIOLOGICALLY ACTIVE SUBSTANCE MOIETY OR SALT THEREOF, AND METHODS FOR PRODUCING SAID COMPOUND OR SALT THEREOF

(71) Applicant: Glytech, Inc., Kyoto (JP)

(72) Inventors: Hirofumi Ochiai, Kyoto (JP); Kenta Yoshida, Hyogo (JP)

(73) Assignee: Glytech, Inc., Kyoto (JP)

( * ) Notice: Subject to any disclaimer, the term of this patent is extended or adjusted under 35 U.S.C. 154(b) by 16 days.

(21) Appl. No.: 14/646,295

(22) PCT Filed: Oct. 30, 2013

(86) PCT No.: PCT/JP2013/079408
§ 371 (c)(1),
(2) Date: May 20, 2015

(87) PCT Pub. No.: WO2014/080730
PCT Pub. Date: May 30, 2014

(65) Prior Publication Data
US 2015/0299337 A1    Oct. 22, 2015

(30) Foreign Application Priority Data
Nov. 22, 2012  (JP) ................................. 2012-256947

(51) Int. Cl.
| A61K 39/00 | (2006.01) |
| C07K 17/10 | (2006.01) |
| A61K 47/48 | (2006.01) |
| C08B 37/00 | (2006.01) |
| C08H 1/00 | (2006.01) |
| A61K 38/00 | (2006.01) |

(52) U.S. Cl.
CPC ............. *C07K 17/10* (2013.01); *A61K 39/00* (2013.01); *A61K 47/48092* (2013.01); *C08B 37/00* (2013.01); *C08H 1/00* (2013.01); *A61K 38/00* (2013.01); *A61K 2039/627* (2013.01)

(58) Field of Classification Search
None
See application file for complete search history.

(56) References Cited

U.S. PATENT DOCUMENTS

| 2009/0082266 A1* | 3/2009 | Nakamura | .......... A61K 47/4823 514/1.1 |
| 2011/0053848 A1* | 3/2011 | Cleemann | ........ A61K 47/48215 514/11.3 |
| 2012/0264684 A1* | 10/2012 | Kajihara | .............. C07K 14/605 514/7.2 |

FOREIGN PATENT DOCUMENTS

| CN | 1648132 | 8/2005 |
| JP | 4-76001 A | 3/1992 |
| JP | 5-39306 A | 2/1993 |
| JP | 6-80705 A | 3/1994 |
| JP | 2001509144 A | 7/2001 |
| JP | 2007501870 A | 2/2007 |
| JP | 2007530423 | 11/2007 |
| JP | 2007530569 A | 11/2007 |
| JP | 2011510954 A | 4/2011 |
| WO | 2006095775 A1 | 9/2006 |
| WO | 2008155900 A1 | 12/2008 |
| WO | 2009095479 A2 | 8/2009 |

OTHER PUBLICATIONS

Bryne et al., "Sialic Acids: Carbohydrate Moieties that Influence the Biological and Physical Properties of Biopharmaceutical Proteins and Living Cells," Drug Discovery Today, vol. 12, Issues 7-8, Apr. 2007, pp. 319-326.
International Search Report, PCT Application No. PCT/JP2013/079408, May 30, 2014, 2 pgs.
Miller et al., "Adaptable Synthesis of C-Glycosidic Multivalent Carbohydrates and Succinamide-Linked Derivatization," Organic Letters, vol. 12, No. 22, pp. 5262-5265, 2010.
Extended European Search Report, Application No. 13857593.1, Jul. 27, 2016, 6 pgs.

* cited by examiner

*Primary Examiner* — Layla Berry
(74) *Attorney, Agent, or Firm* — Dennis A. Bennett; Chris Marion

(57) ABSTRACT

[Problem] The purpose is to provide a compound containing a carrier linker moiety and a physiologically active substance moiety or a salt of the compound, wherein a carrier in the carrier linker moiety is biodegradable and is soluble in water.
[Solution] The purpose can be achieved by employing a sugar chain as a carrier and focusing on the structure of a carrier-linker having a specified structure. A compound containing a carrier linker moiety and a physiologically active substance moiety or a salt of the compound is discovered.

24 Claims, 7 Drawing Sheets

[Figure 1]
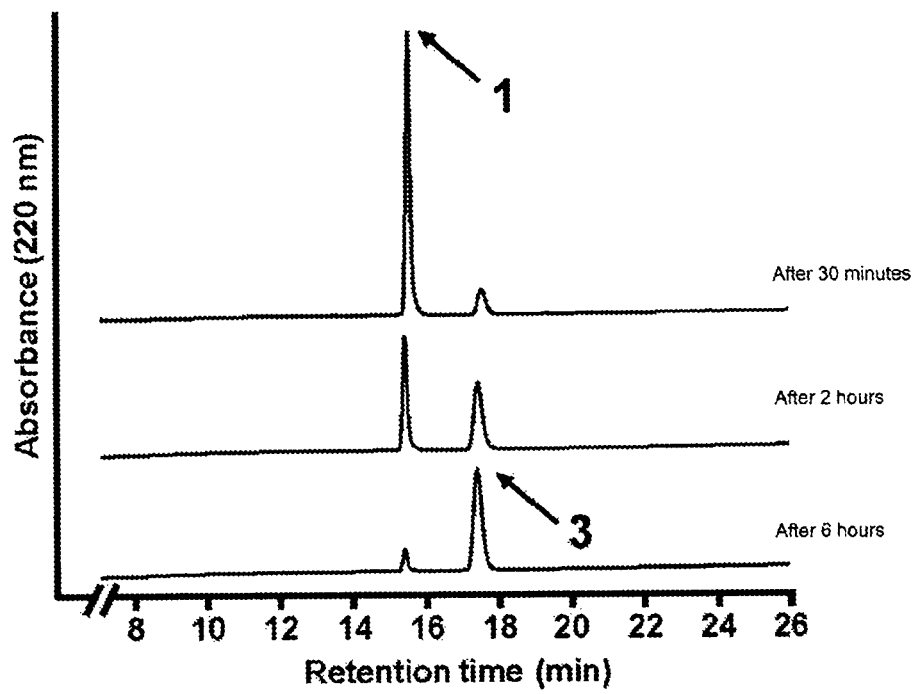

[Figure 2]
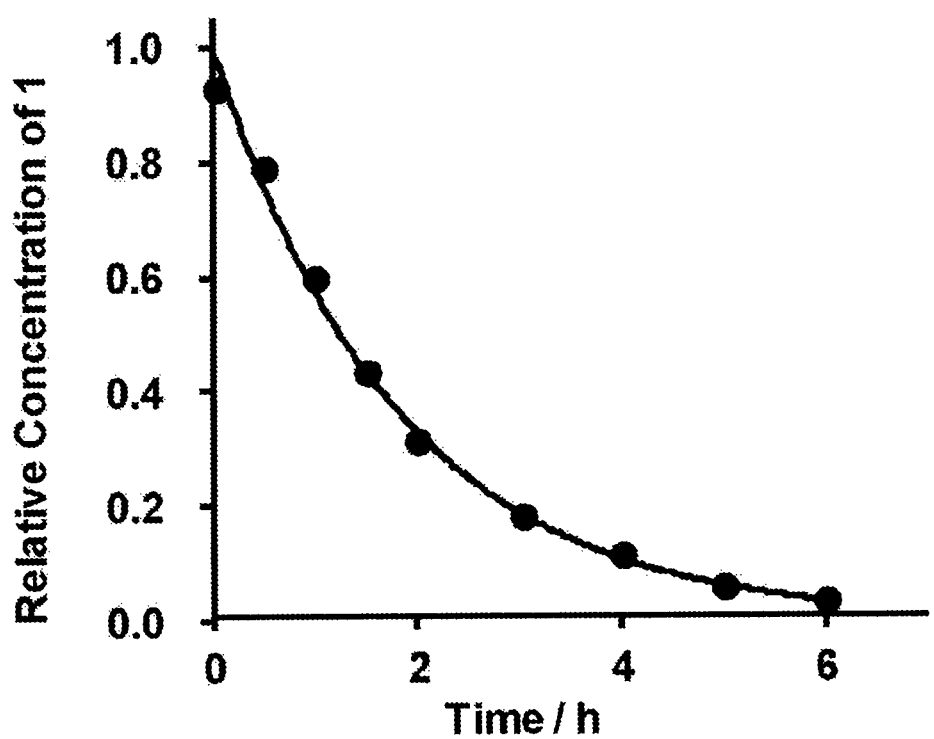

[Figure 3]
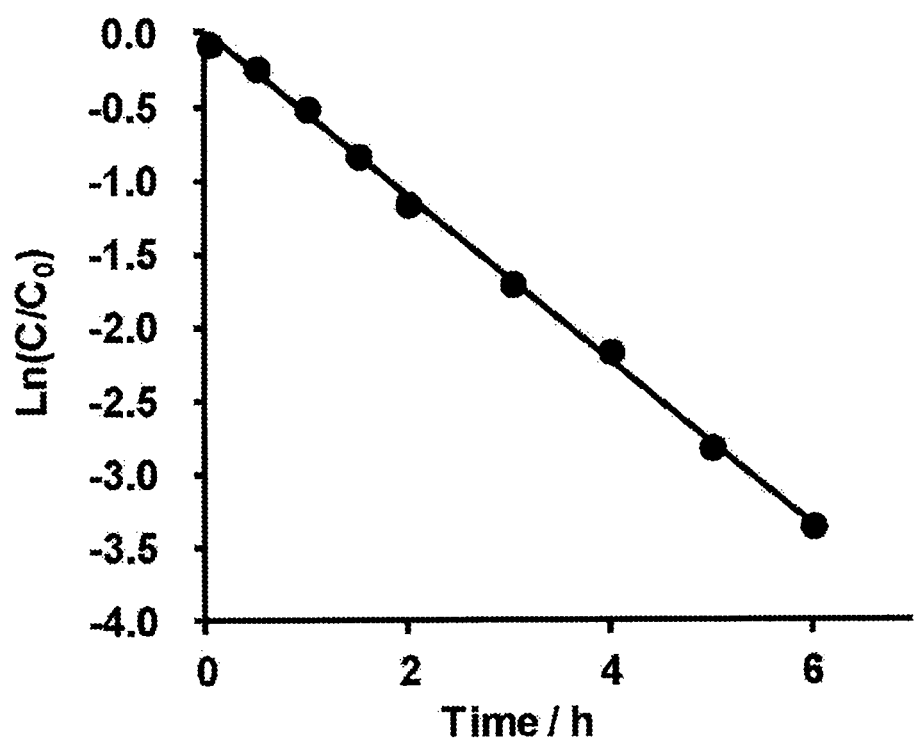

[Figure 4]
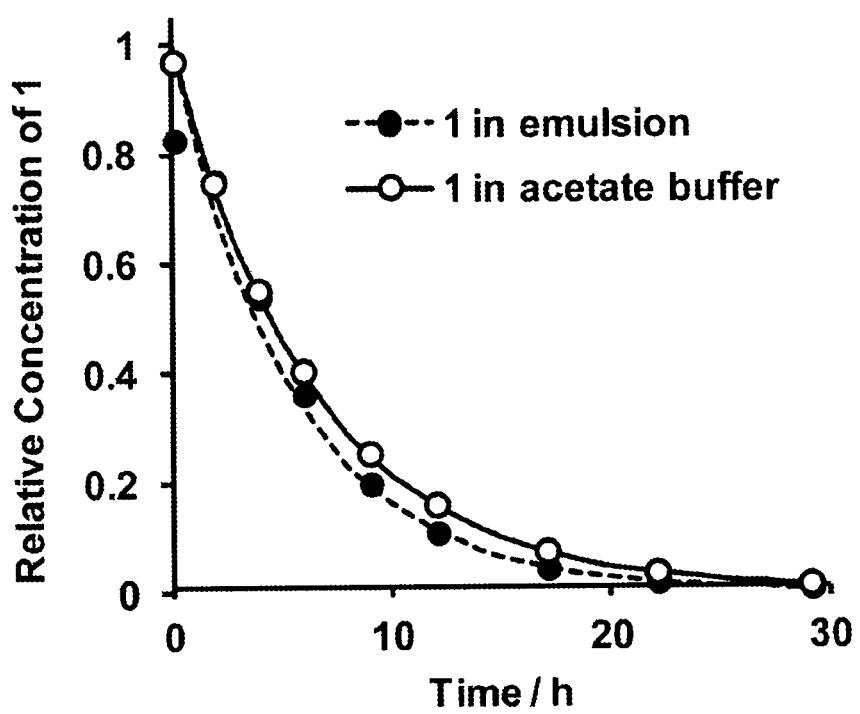

[Figure 5]
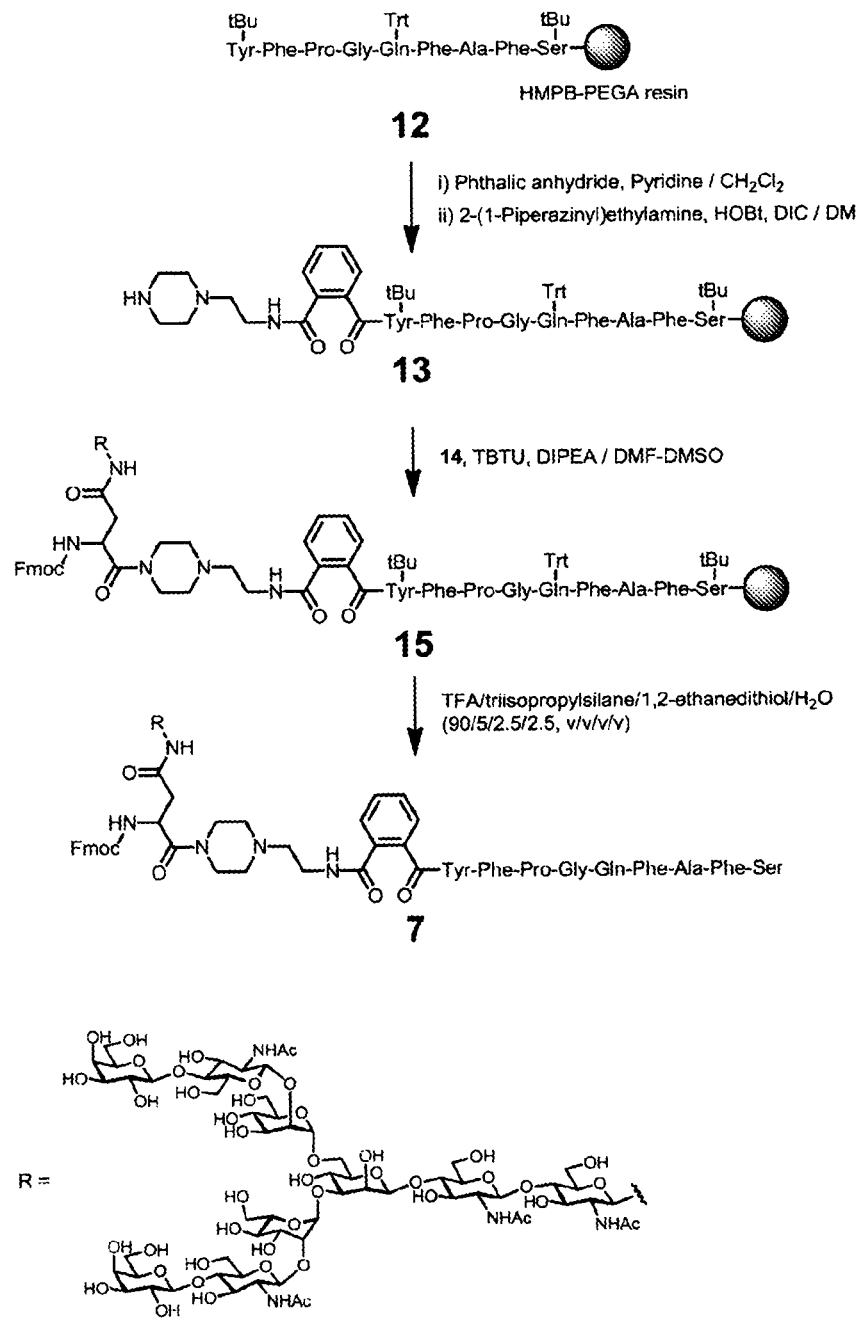

[Figure 6]
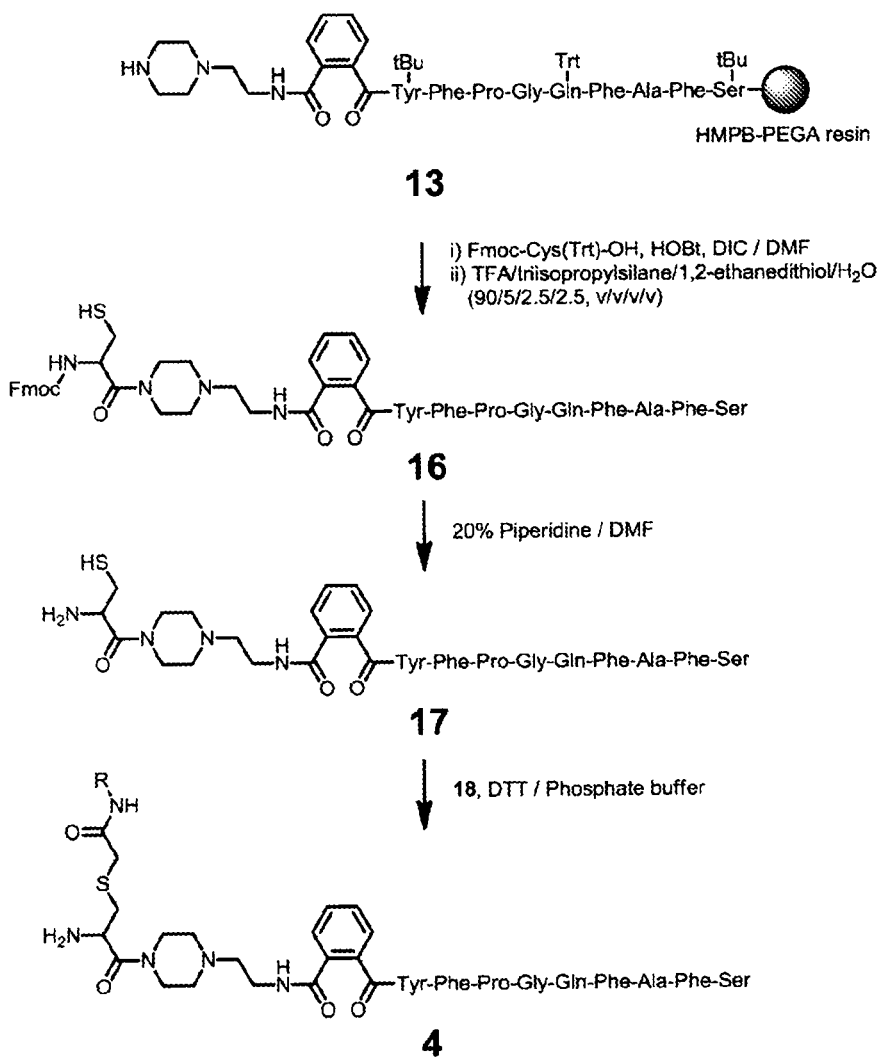

[Figure 7]
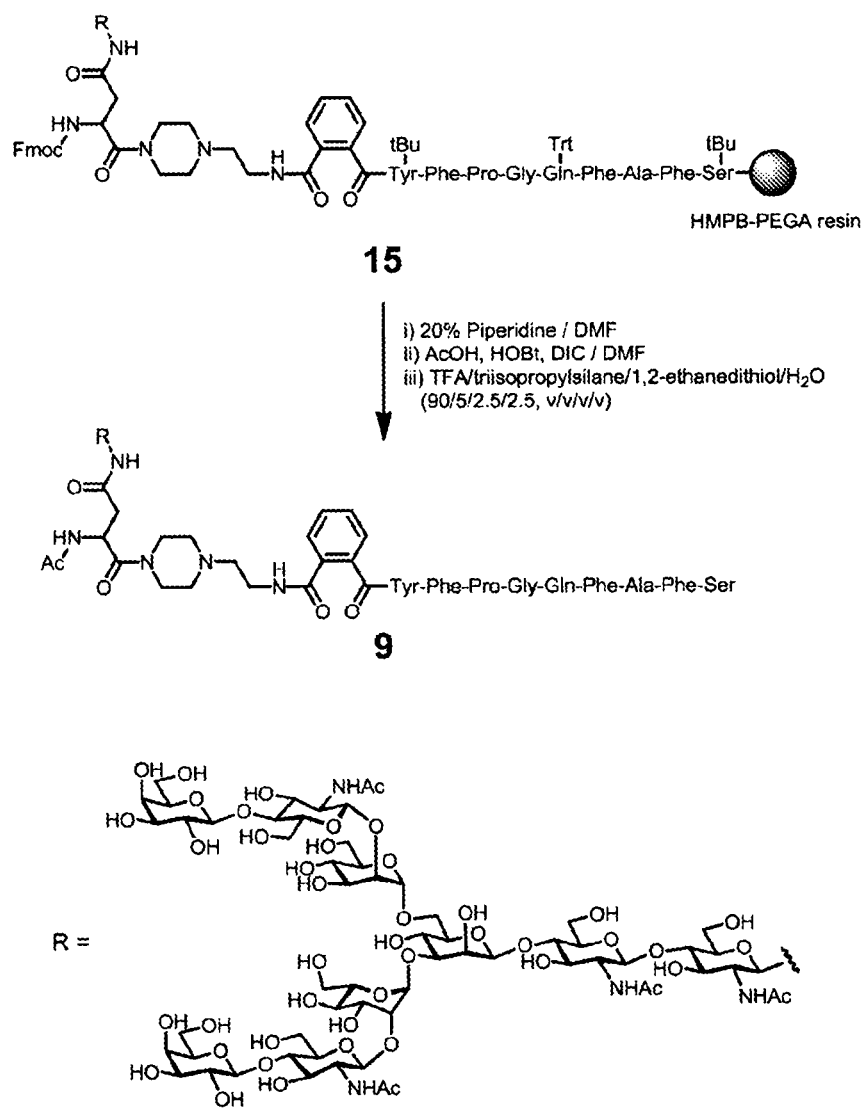

SEQUENCE LISTING

<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Tyr Phe Pro Gly Gln Phe Ala Phe Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: tert-butyl group
<220> FEATURE:
<221> NAME/KEY: BINDING
<222> LOCATION: (5)..(5)
<223> OTHER INFORMATION: trityl group
<220> FEATURE:
<221> NAME/KEY: BINDING
<222> LOCATION: (9)..(9)
<223> OTHER INFORMATION: tert-butyl group
<220> FEATURE:
<221> NAME/KEY: BINDING
<222> LOCATION: (9)..(9)
<223> OTHER INFORMATION: resin

<400> SEQUENCE: 2

Tyr Phe Pro Gly Gln Phe Ala Phe Ser
1               5

<210> SEQ ID NO 3
<211> LENGTH: 9

```
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: tert-butyl group
<220> FEATURE:
<221> NAME/KEY: BINDING
<222> LOCATION: (1)..(1)
<223> OTHER INFORMATION: phthaloyl type-linker moiety
<220> FEATURE:
<221> NAME/KEY: BINDING
<222> LOCATION: (5)..(5)
<223> OTHER INFORMATION: trityl group
<220> FEATURE:
<221> NAME/KEY: BINDING
<222> LOCATION: (9)..(9)
<223> OTHER INFORMATION: tert-butyl group
<220> FEATURE:
<221> NAME/KEY: BINDING
<222> LOCATION: (9)..(9)
<223> OTHER INFORMATION: resin

<400> SEQUENCE: 3

Tyr Phe Pro Gly Gln Phe Ala Phe Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: tert-butyl group
<220> FEATURE:
<221> NAME/KEY: BINDING
<222> LOCATION: (1)..(1)
<223> OTHER INFORMATION: Fmoc-Asn(asialo)type-phthaloyl type-linker
      moiety
<220> FEATURE:
<221> NAME/KEY: BINDING
<222> LOCATION: (5)..(5)
<223> OTHER INFORMATION: trityl group
<220> FEATURE:
<221> NAME/KEY: BINDING
<222> LOCATION: (9)..(9)
<223> OTHER INFORMATION: tert-butyl group
<220> FEATURE:
<221> NAME/KEY: BINDING
<222> LOCATION: (9)..(9)
<223> OTHER INFORMATION: resin

<400> SEQUENCE: 4

Tyr Phe Pro Gly Gln Phe Ala Phe Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc-Asn(asialo)type-phthaloyl type-linker
      moiety

<400> SEQUENCE: 5
```

```
Tyr Phe Pro Gly Gln Phe Ala Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Asn(asialo)type-phthaloyl type-linker moiety

<400> SEQUENCE: 6

Tyr Phe Pro Gly Gln Phe Ala Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc-Cys type-phthaloyl type-linker moiety

<400> SEQUENCE: 7

Tyr Phe Pro Gly Gln Phe Ala Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Cys type-phthaloyl type-linker moiety

<400> SEQUENCE: 8

Tyr Phe Pro Gly Gln Phe Ala Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Cys(GlcNAc)type-phthaloyl type-linker moiety

<400> SEQUENCE: 9

Tyr Phe Pro Gly Gln Phe Ala Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Chemically synthesized
<220> FEATURE:
```

```
<221> NAME/KEY: BINDING
<222> LOCATION: (1)..(1)
<223> OTHER INFORMATION: Cys(asialo)type-phthaloyl type-linker moiety

<400> SEQUENCE: 10

Tyr Phe Pro Gly Gln Phe Ala Phe Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Cys(disialo)type-phthaloyl type-linker moiety

<400> SEQUENCE: 11

Tyr Phe Pro Gly Gln Phe Ala Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc-Cys(disialo)type-phthaloyl type-linker
      moiety

<400> SEQUENCE: 12

Tyr Phe Pro Gly Gln Phe Ala Phe Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Ac-Asn(asialo)type-phthaloyl type-linker moiety

<400> SEQUENCE: 13

Tyr Phe Pro Gly Gln Phe Ala Phe Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Asn(asialo)type-tetrachlorophthaloyl
      type-linker moiety

<400> SEQUENCE: 14

Tyr Phe Pro Gly Gln Phe Ala Phe Ser
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Chemically synthesized

<400> SEQUENCE: 15

Arg Trp Gly Leu Leu Leu Ala Leu Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Fmoc group
<220> FEATURE:
<221> NAME/KEY: BINDING
<222> LOCATION: (1)..(1)
<223> OTHER INFORMATION: Pbf group
<220> FEATURE:
<221> NAME/KEY: BINDING
<222> LOCATION: (2)..(2)
<223> OTHER INFORMATION: Boc group

<400> SEQUENCE: 16

Arg Trp Gly Leu Leu Leu Ala Leu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Asn(asialo)type-phthaloyl type-linker moiety

<400> SEQUENCE: 17

Arg Trp Gly Leu Leu Leu Ala Leu Leu
1               5
```

GLYCOSYLATED LINKER, COMPOUND CONTAINING GLYCOSYLATED LINKER MOIETY AND PHYSIOLOGICALLY ACTIVE SUBSTANCE MOIETY OR SALT THEREOF, AND METHODS FOR PRODUCING SAID COMPOUND OR SALT THEREOF

This application is a U.S. National Stage Application under 35 U.S.C. §371 of International Application No. PCT/JP2013/079408, filed Oct. 30, 2013, which claims priority to Japan Application No. 2012-256947 filed Nov. 22, 2012. Each of the above-referenced applications is expressly incorporated by reference herein its entirety.

TECHNICAL FIELD

The present invention relates to a glycosylated linker, a compound containing a glycosylated linker moiety and a physiologically active substance moiety, or a salt thereof, and methods for producing said compound or salt thereof.

BACKGROUND ART

Some physiologically active substances cannot be (sufficiently) filter-sterilized due to their low water solubility in an attempt to administer them to organisms as drugs. Also, some physiologically active substances are difficult to dissolve in an aqueous solution or an emulsion prepared from the aqueous solution for administration to organisms.

Various methods have been attempted to improve the water solubility of drugs such as physiologically active substances. For example, a carrier-drug conjugate (so-called a drug derivative) is known in which a highly water-soluble carrier is covalently bonded to a drug. A hydrophilic amino acid sequence, polyethylene glycol (PEG), or the like is known as the carrier.

Such a drug derivative, however, differs in steric structure from the original drug and therefore exhibits different pharmacokinetic, immunogenic, toxicological, or pharmacological properties, etc., compared with the original drug. When the drug derivative is used as, for example, a vaccine, its antigenicity is known to be generally lower than that of the unmodified drug.

A drug with PEG added as a carrier (PEGylated drug) is resistant to biodegradation. Thus, the PEGylated drug, when continuously administered into an organism, might accumulate in the organism to cause chemical injury to the organism (Patent Literature 1). Furthermore, PEG has a molecular weight distribution (polydisperse nature). Thus, the PEGylation of drugs forms many monomeric isoforms having distinctive activity (different monomeric isoforms: structurally different proteins), because of the difference in the binding site or molecular weight of added PEG. These formed isoforms might compete with each other for binding to a drug acceptor molecule (Non Patent Literature 1).

A carrier-linker-drug conjugate has also been developed in which a drug and a carrier are bonded via a linker moiety. This conjugate is designed such that the bond between the carrier-linker moiety and the drug is cleaved at a target site (in blood, etc.) to release the drug itself. For such cleavage of the bond, light or enzymatic cleavage has been used as a trigger. Unfortunately, the in vivo light irradiation of the target site is difficult, and the light might damage the organism. Also, in the case of the enzymatic cleavage, the amount of an enzyme is known to largely differ among individuals or depending on administration sites. Thus, the problem of this approach is to cause variations in the effect of the drug therapy.

In this respect, the utilization of autohydrolysis based on intramolecular catalysis in the linker has been attempted for the cleavage of the carrier-linker moiety from the drug in the carrier-linker-drug conjugate. A conjugate in which a linker moiety is bonded through an amide bond to a drug via an amino group derived from the drug has been reported as this type of conjugate (Patent Literature 2). The cleavage mechanism of this conjugate is based on the cleavage of the amide bond by cyclization-activation resulting from cyclic imide formation in the linker.

CITATION LIST

Patent Literature

[Patent Literature 1] National Publication of International Patent Application No. 2007-530569
[Patent Literature 2] International Publication No. WO 2009/095479

Non Patent Literature

[Non Patent Literature 1] Barry Byrne et al., Drug Discovery Today, (2007), Vol. 12, pp. 319-326

SUMMARY OF INVENTION

Technical Problem

Patent Literature 2, however, has not paid attention to the biodegradability of the carrier. Furthermore, this literature has made no mention about the water solubility of the carrier-linker-drug conjugate.

An object of the present invention is to provide a compound comprising a carrier-linker moiety with a biodegradable and water-soluble carrier and a physiologically active substance moiety, or a salt thereof.

Solution to Problem

As a result of conducting diligent studies, the present inventors have adopted a sugar chain as a carrier and focused on the structure of a carrier-linker having the particular structure, thereby finding a compound comprising a carrier-linker moiety and a physiologically active substance moiety, or a salt thereof, which attains the above-mentioned object.

Specifically, the object of the present invention is attained by providing a compound comprising a glycosylated linker moiety and a physiologically active substance moiety, or a salt thereof, the compound being represented by the following formula (A):

$$R^1\text{—}X \tag{A}$$

wherein
$R^1$ represents the glycosylated linker moiety;
$R^1$ is represented by the following formula (I):

[Formula 1]

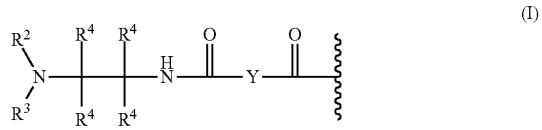

in the formula (I),
$R^2$ and $R^3$ each independently represent a hydrogen atom, an alkyl group having 1 to 16 carbon atoms, or an aryl group having 5 to 16 carbon atoms (provided that both of $R^2$ and $R^3$ are not hydrogen atoms at the same time), or $R^2$ and $R^3$ form a 3- to 7-membered heterocyclic ring together with the nitrogen atom to which they are bonded, wherein at least one hydrogen atom in the alkyl group, the aryl group, or the heterocyclic ring is replaced by a sugar chain, a glycosylated amino acid, or a glycosylated polypeptide;

each $R^4$ independently represents a hydrogen atom, an alkyl group having 1 to 16 carbon atoms, or an aryl group having 5 to 16 carbon atoms;

Y represents

[Formula 2]

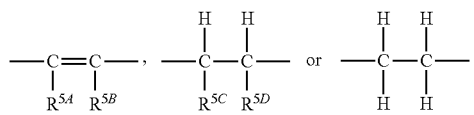

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and $R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded; and the wavy line represents a binding site to X;
X represents the physiologically active substance moiety, the physiologically active substance having at least one amino group, hydroxy group, thiol group, or carboxy group; and
the bonding of X to $R^1$ is a bond at the at least one amino group, hydroxy group, thiol group, or carboxy group.

According to one embodiment, in the compound of the present invention or a salt thereof, preferably,
the $R^1$ is represented by the following formula (I):

[Formula 3]

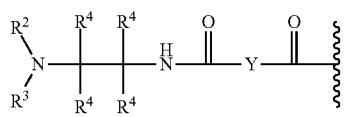

in the formula (I),
$R^2$ and $R^3$ form a 3- to 7-membered heterocyclic ring together with the nitrogen atom to which they are bonded, wherein the heterocyclic ring is selected from the group consisting of aziridine, azetidine, pyrroline, pyrrole, imidazole, imidazoline, pyrazole, pyrazoline, isoxazoline, thiazoline, isothiazoline, thiadiazoline, pyrrolidine, imidazolidine, pyrazolidine, oxazolidine, isoxazolidine, thiazolidine, isothiazolidine, thiadiazolidine, piperazine, piperidine, morpholine, thiomorpholine, thiazine, tetrazole, triazole, triazolidine, tetrazolidine, azepane, diazepane, azepine, and homopiperazine, at least one hydrogen atom in the heterocyclic ring is replaced by a glycosylated amino acid or a glycosylated polypeptide, and the replacement is a bond at the site of the amino acid or the polypeptide in the "glycosylated amino acid or glycosylated polypeptide";

each $R^4$ independently represents a hydrogen atom, an alkyl group having 1 to 16 carbon atoms, or an aryl group having 5 to 16 carbon atoms;

Y represents

[Formula 4]

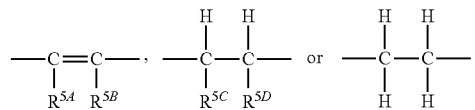

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R_{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and $R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded; and the wavy line represents a binding site to the X.

According to one embodiment, in the compound of the present invention or a salt thereof, preferably,
the $R^1$ is represented by the following formula (II):

[Formula 5]

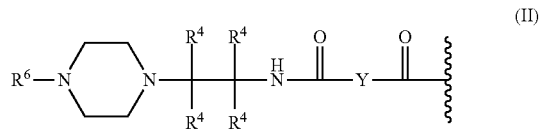

in the formula (II),
each $R^4$ independently represents a hydrogen atom, an alkyl group having 1 to 16 carbon atoms, or an aryl group having 5 to 16 carbon atoms;

Y represents

[Formula 6]

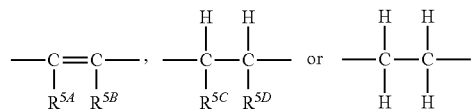

wherein $R^{5A}$ and $R^{5B}$ form aryl having 5 to 16 carbon atoms together with the carbon atom to which $R^{5A}$ is bonded and the carbon atom to which $R^{5B}$ is bonded, or both of $R^{5A}$ and $R^{5B}$ are hydrogen atoms, and $R^{5C}$ and $R^{5D}$ form cyclohexyl or norbornyl together with the carbon atom to which $R^{5C}$ is bonded and the carbon atom to which $R^{5D}$ is bonded;

$R^6$ represents a sugar chain, a glycosylated amino acid, or a glycosylated polypeptide; and the wavy line represents a binding site to the X.

According to one embodiment, in the compound of the present invention or a salt thereof, preferably, the physiologically active substance has a peptide moiety; and the bonding of the X to the $R^1$ is (1) an amide bond at the N-terminal amino group of the peptide moiety in the physiologically active substance, (2) an ester bond at a hydroxy group present in the side chain of a serine residue, a threonine residue, or a tyrosine residue of the peptide moiety in the physiologically active substance (but only in the case where the peptide moiety in the physiologically active substance has the serine residue, the threonine residue, or the tyrosine residue), (3) an acid anhydride bond at a carboxy group present in the side chain of an aspartic acid residue or a glutamic acid residue of the peptide moiety in the physiologically active substance (but only in the case where the peptide moiety in the physiologically active substance has the aspartic acid residue or the glutamic acid residue), (4) an amide bond at an amino group present in the side chain of a lysine residue, an asparagine residue, an arginine residue, a histidine residue, or a tryptophan residue of the peptide moiety in the physiologically active substance (but only in the case where the peptide moiety in the physiologically active substance has the lysine residue, the asparagine residue, the arginine residue, the histidine residue, or the tryptophan residue), (5) a thioester bond at a thiol group present in the side chain of a cysteine residue of the peptide moiety in the physiologically active substance (but only in the case where the peptide moiety in the physiologically active substance has the cysteine residue), or (6) an acid anhydride bond at the C-terminal carboxy group of the peptide moiety in the physiologically active substance.

According to one embodiment, in the compound of the present invention or a salt thereof, preferably, the $R^1$ is represented by the following formula (III):

[Formula 7]

(III)

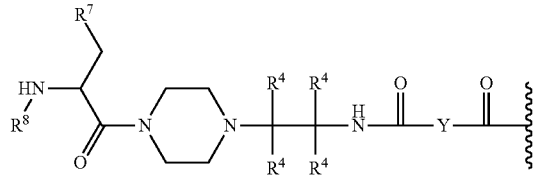

in the formula (III), each $R^4$ independently represents a hydrogen atom, an alkyl group having 1 to 16 carbon atoms, or an aryl group having 5 to 16 carbon atoms;

Y represents

[Formula 8]

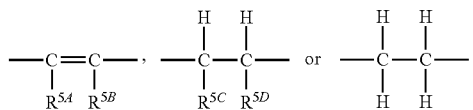

wherein $R^{5A}$ and $R^{5B}$ form aryl having 5 to 16 carbon atoms together with the carbon atom to which $R^{5A}$ is bonded and the carbon atom to which $R^{5B}$ is bonded, or both of $R^{5A}$ and $R^{5B}$ are hydrogen atoms, and $R^{5C}$ and $R^{5D}$ form cyclohexyl or norbornyl together with the carbon atom to which $R^{5C}$ is bonded and the carbon atom to which $R^{5D}$ is bonded;

$R^7$ represents —S—CH$_2$—CONH-sugar chain or —CONH-sugar chain;

$R^8$ represents a hydrogen atom, an acyl group having 1 to 16 carbon atoms, a carbamate protective group (e.g., an Fmoc group, a Boc group, a Z group, a Troc group, or an Alloc group), a sugar chain, an amino acid, a polypeptide, a glycosylated amino acid, or a glycosylated polypeptide; and the wavy line represents a binding site to X;

the physiologically active substance has at least one amino group; and the bonding of the X to the $R^1$ is a bond at the at least one amino group.

According to one embodiment of the present invention, preferably, the $R^1$ is represented by the following formula (IV):

[Formula 9]

(IV)

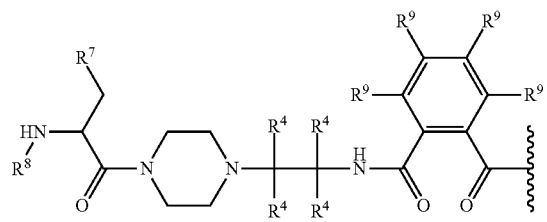

in the formula (IV), each $R^4$ independently represents a hydrogen atom, an alkyl group having 1 to 16 carbon atoms, or an aryl group having 5 to 16 carbon atoms;

$R^7$ represents —S—CH$_2$—CONH-sugar chain or —CONH-sugar chain;

$R^8$ represents a hydrogen atom, an acyl group having 1 to 16 carbon atoms, a carbamate protective group (e.g., an Fmoc group, a Boc group, a Z group, a Troc group, or an Alloc group), a sugar chain, an amino acid, a polypeptide, a glycosylated amino acid, or a glycosylated polypeptide;

each $R^9$ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group; and the wavy line represents a binding site to X;

the physiologically active substance has at least one amino group; and the bonding of the X to the $R^1$ is a bond at the at least one amino group.

According to one embodiment, in the compound of the present invention or a salt thereof, preferably, all of the four $R^4$ moieties in the formula (I), (II), (III), or (IV) are hydrogen atoms.

According to one embodiment, in the compound of the present invention or a salt thereof, preferably, at least one of the $R^9$ moieties in the formula (IV) is halogen.

According to one embodiment, in the compound of the present invention or a salt thereof, preferably, all of the four $R^9$ moieties in the formula (IV) are chlorine atoms.

According to one embodiment, in the compound of the present invention or a salt thereof, preferably, the sugar chain in the "glycosylated amino acid or glycosylated polypeptide" is bonded to Asn or Cys in the amino acid or the polypeptide.

According to one embodiment, in the compound of the present invention or a salt thereof, preferably, the sugar chain in the "glycosylated amino acid or glycosylated polypeptide" is bonded to the amino acid or the polypeptide without the mediation of a linker.

According to one embodiment, in the compound of the present invention or a salt thereof, preferably, the sugar chain in the "sugar chain, glycosylated amino acid, or glycosylated polypeptide" consists of 4 or more sugar residues.

According to one embodiment, in the compound of the present invention or a salt thereof, preferably, the sugar chain in the "sugar chain, glycosylated amino acid, or glycosylated polypeptide" is a biantennary complex-type sugar chain, a triantennary complex-type sugar chain, or a tetraantennary complex-type sugar chain.

According to one embodiment, in the compound of the present invention or a salt thereof, preferably, the sugar chain is a biantennary complex-type sugar chain selected from the group consisting of a disialo sugar chain, a monosialo sugar chain, an asialo sugar chain, a di-GlcNAc sugar chain, and a dimannose sugar chain.

According to one embodiment, in the compound of the present invention or a salt thereof, preferably, the sugar chain in the "sugar chain, glycosylated amino acid, or glycosylated polypeptide" is a sugar chain represented by the following formula:

[Formula 10]

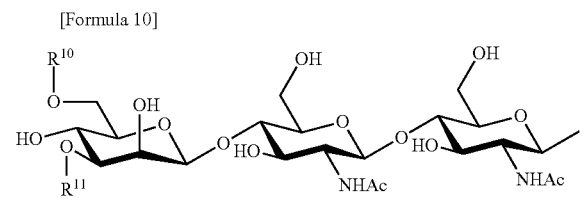

wherein $R^{10}$ and $R^{11}$ are the same or different and each represent

[Formula 11]

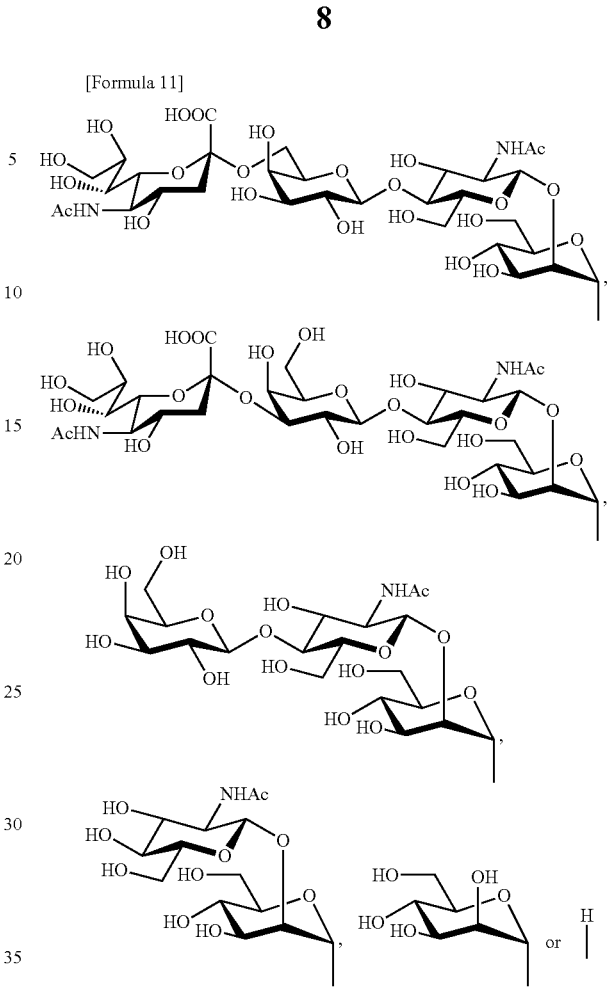

and Ac represents an acetyl group.

According to one embodiment, in the compound of the present invention or a salt thereof, preferably, the physiologically active substance is a low-molecular physiologically active substance or a biopolymer.

According to one embodiment, in the compound of the present invention or a salt thereof, preferably, the biopolymer is selected from the group consisting of a protein, a polypeptide, a polynucleotide, and a peptide nucleic acid.

According to one embodiment, in the compound of the present invention or a salt thereof, preferably, the compound or the salt thereof has improved water solubility compared with an unmodified physiologically active substance.

According to one embodiment, in the compound of the present invention or a salt thereof, preferably, the improved water solubility is 10 to 1,000,000 times the water solubility of the "unmodified physiologically active substance" in terms of molar concentration.

According to one embodiment, in the compound of the present invention or a salt thereof, preferably, the glycosylated linker moiety is autocatalytically cleaved in a manner dependent on pH and/or temperature.

One or any combination of two or more of the features of the present invention mentioned above is also included in the scope of the compound of the present invention or the salt thereof, as a matter of course.

In another aspect, the present invention provides a composition comprising the compound or the salt thereof, wherein sugar chains in the compound or the salt thereof are substantially homogeneous.

The composition of the present invention is preferably a pharmaceutical composition.

In an alternative aspect, the present invention provides
a pharmaceutical composition comprising
(I) the compound or the salt thereof, and
(II) a pharmacologically acceptable carrier.

According to one embodiment, in the pharmaceutical composition of the present invention, preferably,
the physiologically active substance immediately exerts its activity after administration to a subject.

According to one embodiment, preferably,
the pharmaceutical composition of the present invention is used in vaccination.

One or any combination of two or more of the features of the present invention mentioned above is also included in the scope of the (pharmaceutical) composition of the present invention, as a matter of course.

In a further alternative aspect, the present invention provides
a method for producing a compound comprising a glycosylated linker moiety and a physiologically active substance moiety, or a salt thereof, wherein
the physiologically active substance comprises a peptide moiety having at least one amino group, hydroxy group, thiol group, or carboxy group,
the production method comprising the following steps:
(a) synthesizing the peptide moiety on a resin by a solid-phase synthesis method;
(b) bonding a linker moiety represented by the following formula (I') to the "amino group, hydroxy group, thiol group, or carboxy group" in the peptide moiety synthesized in the step (a):

[Formula 12]

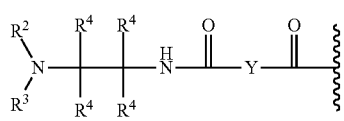

(I')

in the formula (I'),
$R^2$ and $R^3$ each independently represent a hydrogen atom, an alkyl group having 1 to 16 carbon atoms, or an aryl group having 5 to 16 carbon atoms (provided that both of $R^2$ and $R^3$ are not hydrogen atoms at the same time), or $R^2$ and $R^3$ form a 3- to 7-membered heterocyclic ring together with the nitrogen atom to which they are bonded;
each $R^4$ independently represents a hydrogen atom, an alkyl group having 1 to 16 carbon atoms or an aryl group having 5 to 16 carbon atoms;
Y represents

[Formula 13]

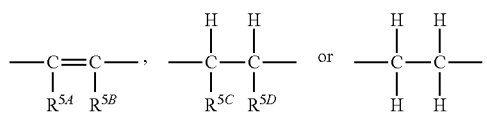

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and $R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded; and the wavy line represents a binding site to the "amino group, hydroxy group, thiol group, or carboxy group" in the peptide moiety; and (c) replacing at least one hydrogen atom in the alkyl group, the aryl group, or the heterocyclic ring represented by $R^2$ or $R^3$ in the linker moiety bonded to the "amino group, hydroxy group, thiol group, or carboxy group" in the peptide moiety by the step (b), with a sugar chain, a glycosylated amino acid, or a glycosylated polypeptide.

In a further alternative aspect, the present invention provides
a method for producing a compound comprising a glycosylated linker moiety and a physiologically active substance moiety, or a salt thereof, wherein
the physiologically active substance comprises a peptide moiety having at least one amino group, hydroxy group, thiol group, or carboxy group,
the production method comprising bonding a glycosylated linker represented by the following formula (I") to the "amino group, hydroxy group, thiol group, or carboxy group" in the peptide moiety by dehydration condensation:

[Formula 14]

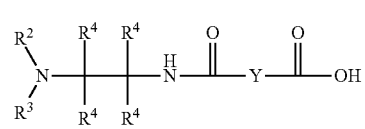

(I")

in the formula (I"),
$R^2$ and $R^3$ each independently represent a hydrogen atom, an alkyl group having 1 to 16 carbon atoms, or an aryl group having 5 to 16 carbon atoms (provided that both of $R^2$ and $R^3$ are not hydrogen atoms at the same time), or $R^2$ and $R^3$ form a 3- to 7-membered heterocyclic ring together with the nitrogen atom to which they are bonded, wherein
at least one hydrogen atom in the alkyl group, the aryl group, or the heterocyclic ring is replaced by a sugar chain, a glycosylated amino acid, or a glycosylated polypeptide;
each $R^4$ independently represents a hydrogen atom, an alkyl group having 1 to 16 carbon atoms, or an aryl group having 5 to 16 carbon atoms; and Y represents

[Formula 15]

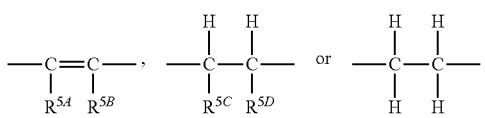

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and
$R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded.

One or any combination of two or more of the features of the present invention mentioned above is also included in the scope of the method for producing the compound of the present invention or the salt thereof, as a matter of course.

In an alternative aspect, the present invention provides
a compound or a salt thereof obtainable by any of the production methods.

In an alternative aspect, the present invention provides
a compound or a salt thereof obtained by any of the production methods.

One or any combination of two or more of the features of the present invention mentioned above is also included in the scope of the compound of the present invention or the salt thereof, as a matter of course.

In a further alternative aspect, the present invention provides
a glycosylated linker which may be used for bonding to a physiologically active substance having at least one amino group, hydroxy group, thiol group, or carboxy group, wherein
the glycosylated linker is represented by the following formula (B):

$R^1$-L     (B)

wherein
$R^1$ represents a glycosylated linker moiety;
$R^1$ is represented by the following formula (I):

[Formula 15]

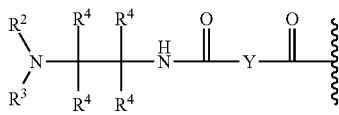

in the formula (I),
$R^2$ and $R^3$ each independently represent a hydrogen atom, an alkyl group having 1 to 16 carbon atoms, or an aryl group having 5 to 16 carbon atoms (provided that both of $R^2$ and $R^3$ are not hydrogen atoms at the same time), or $R^2$ and $R^3$ form a 3- to 7-membered heterocyclic ring together with the nitrogen atom to which they are bonded, wherein
at least one hydrogen atom in the alkyl group, the aryl group, or the heterocyclic ring is replaced by a sugar chain, a glycosylated amino acid, or a glycosylated polypeptide;
each $R^4$ independently represents a hydrogen atom, an alkyl group having 1 to 16 carbon atoms, or an aryl group having 5 to 16 carbon atoms;
Y represents

[Formula 17]

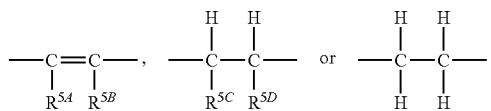

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and
$R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded; and
the wavy line represents a binding site to L; and
L represents a leaving group.

One or any combination of two or more of the features of the present invention mentioned above is also included in the scope of the glycosylated linker of the present invention, as a matter of course.

Advantageous Effects of Invention

The compound comprising a glycosylated linker moiety and a physiologically active substance moiety or the salt thereof according to the present invention is rich in hydroxy groups and has a highly polar sugar chain. The compound of the present invention or the salt thereof therefore has improved water solubility compared with an unmodified physiologically active substance. In addition, a sugar chain having biodegradable nature is used as a carrier. The compound of the present invention or the salt thereof therefore causes little chemical injury when administered to an organism.

BRIEF DESCRIPTION OF DRAWINGS

FIG. 1 is a diagram showing time-dependent change in the abundance of glycosylated (Asn (asialo)-type) linker-chemerin 9 conjugate (compound 1) and unmodified chemerin 9 (compound 3) dissolved in PBS at 37° C. and pH 7.4. The ordinate denotes absorbance at a wavelength of 220 nm. The abscissa denotes retention time (min). Peak 1 indicated by the arrow represents the glycosylated (Asn (asialo)-type) linker-chemerin 9 conjugate (compound 1). Peak 3 indicated by the arrow represents the unmodified chemerin 9.

FIG. 2 is a diagram showing the relative concentration vs. incubation time of the glycosylated (Asn (asialo)-type) linker-chemerin 9 conjugate (compound 1) dissolved in PBS (37° C., pH 7.4). The ordinate denotes the relative concentration. The abscissa denotes time (h). The phrase "Relative Concentration of 1" described in the ordinate means the relative concentration of the dissolved glycosylated (Asn (asialo)-type) linker-chemerin 9 conjugate (compound 1).

FIG. 3 is a diagram showing natural logarithm of the relative concentration vs. incubation time of the glycosylated (Asn (asialo)-type) linker-chemerin 9 conjugate (compound 1) dissolved in PBS (37° C., pH 7.4). The ordinate denotes the natural logarithm ($Ln(C/C_0)$) of the relative concentration. The abscissa denotes time (h).

FIG. 4 is a diagram showing the comparison of the relative concentration vs. incubation time at 25° C. of the glycosylated (Asn (asialo)-type) linker-chemerin 9 conjugate (compound 1) dissolved in a 0.1 M acetate buffer solution (pH 4.0) or an emulsion solution prepared on the basis of the acetate buffer solution. The ordinate denotes the relative concentration. The abscissa denotes time (h). The dotted line with filled circles ("1 in emulsion") and the line with open circles ("1 in acetate buffer") represent the relative concentration vs. incubation time of the glycosylated (Asn (asialo)-type) linker-chemerin 9 conjugate (compound 1) in the emulsion solution and in the 0.1 M acetate buffer solution, respectively. The phrase "Relative Concentration of 1" described in the ordinate means the relative concentration of the dissolved glycosylated (Asn (asialo)-type) linker-chemerin 9 conjugate (compound 1).

FIG. 5 is a diagram showing synthesis of glycosylated (Fmoc-Asn (asialo)-type) linker-chemerin 9 conjugate (compound 7) (SEQ ID NO: 5) [Formula 74].

FIG. 6 is a diagram showing synthesis of glycosylated (Cys (GlcNAc)-type) linker-chemerin 9 conjugate (compound 4)) [Formula 78].

FIG. 7 is a diagram showing synthesis of glycosylated (Ac-Asn (asialo)-type) linker-chemerin 9 conjugate (compound 9)) [Formula 88].

DESCRIPTION OF EMBODIMENTS

Hereinafter, preferred embodiments of the present invention will be described.

In the present specification, the phrase "physiologically active substance derivative having a glycosylated linker moiety" is used interchangeably with the "compound comprising a glycosylated linker moiety and a physiologically active substance moiety, or the salt thereof" according to the present invention. In the present specification, the term "conjugate" means a drug (physiologically active substance, etc.) bonded to a different substance (e.g., a carrier or a carrier-linker (glycosylated linker, etc.)).

The glycosylated linker of the present invention is a linker with a sugar chain added as a carrier. The glycosylated linker of the present invention may have two or more identical or different sugar chains.

In the present specification, a physiologically active substance moiety (X) and a glycosylated linker moiety ($R^1$) can be bonded to each other to form a compound comprising a glycosylated linker moiety and a physiologically active substance moiety, represented by the formula (A) "$R^1$—X", or a salt thereof.

In the present invention, the physiologically active substance can bind to the glycosylated linker moiety as a result of partial alteration (modification) of the structure of the physiologically active substance. Once the glycosylated linker moiety is cleaved, however, the physiologically active substance is released. Preferably, the released physiologically active substance is structurally the same as the compound before the bonding to the glycosylated linker moiety (before the modification). In the present specification, the physiologically active substance unbound with the glycosylated linker is referred to as an "unmodified physiologically active substance". Preferably, the unmodified physiologically active substance has the original pharmacokinetic, immunogenic, toxicological, or pharmacological properties of the physiologically active substance itself, while the properties may be altered or modified, for example. Preferably, the "compound comprising a glycosylated linker moiety and a physiologically active substance moiety, or the salt thereof" according to the present invention releases the unmodified physiologically active substance through the cleavage of the glycosylated linker moiety under predetermined conditions.

Preferably, the glycosylated linker of the present invention has no adverse effect on the pharmacokinetic, immunogenic, toxicological, or pharmacological properties, etc., of its binding partner physiologically active substance.

In the present specification, the "physiologically active substance" means, but not limited to, a substance that has a certain effect or influence either directly or indirectly on the physiological activity of an organism. The physiologically active substance may be intended to be used in vitro and in vivo. The physiologically active substance may exert no function in itself in vivo. In a certain embodiment, the physiologically active substance may be used interchangeably with a drug. The physiologically active substance may include substances useful as vaccines or medicines as well as substances that have no direct effect or influence on the physiological activity of an organism, for example, diagnostic agents. Also, the physiologically active substance may include naturally occurring substances as well as partial deletion, modification, or substitution products (also referred to as derivatives) thereof. The physiologically active substance may further include artificially synthesized substances (e.g., substances produced by a biological approach such as recombinant DNA technology or by a chemical synthetic approach such as a solid-phase peptide synthesis method) and fusion products of a portion of a naturally occurring substance and a portion of an artificially synthesized substance. Thus, the physiologically active substance according to the present invention also includes substances fused with, for example, a reporter protein such as GFP (green fluorescent protein) or a fluorescent dye such as fluorescein.

The physiologically active substance according to the present invention has at least one amino group, hydroxy group, thiol group, or carboxy group. The physiologically active substance according to the present invention is preferably a low-molecular physiologically active substance or a biopolymer having at least one amino group, hydroxy group, thiol group, or carboxy group.

In the present specification, the "biopolymer" may mean a macromolecular organic compound among the physiologically active substances. On the other hand, the "low-molecular physiologically active substance" may mean a low-molecular organic compound among the physiologically active substances. The biopolymer may be, for example, a polymer compound such as a protein, a nucleic acid, or a polysaccharide, or a portion thereof, or may be artificially synthesized. The low-molecular physiologically active substance may be, for example, a substance that can interact with the biopolymer in vivo, or may be artificially synthesized. In the present specification, however, the biopolymer and the low-molecular physiologically active substance may be the same as each other in some cases.

According to one embodiment, preferably, the biopolymer according to the present invention is a protein, a polypeptide, a polynucleotide, or a peptide nucleic acid having at least one amino group, hydroxy group, thiol group, or carboxy group, or contains such a protein, polypeptide, polynucleotide, or peptide nucleic acid in a portion of its structure. In the present specification, the portion derived from the protein or the polypeptide is also referred to as a "peptide moiety".

In the present specification, the "protein" is not particularly limited as long as the protein is composed of a plurality of amino acids joined through amide bonds. The protein includes known proteins, novel proteins, or their variants. In the present specification, the "variant" is a naturally or artificially partially altered compound of the protein. Examples of such alteration include alkylation, acylation (e.g., acetylation), amidation (e.g., C-terminal amidation of the protein), carboxylation, esterification, disulfide bond formation, glycosylation, lipidation, phosphorylation, hydroxylation, dehydration condensation, or labeling component bonding of one or more amino acid residues in the protein. Alternatively, examples of the variant include partial deletion, substitution, or fusion products of the structures of known proteins or novel proteins. When the biopolymer as the physiologically active substance is a protein, the protein may be synthesized by use of, but not limited to, a method generally known to those skilled in the art, for example, solid-phase synthesis, liquid-phase synthesis, cell-based synthesis, or separation and extraction of a naturally occurring protein.

In the present specification, the "polypeptide" and the "peptide" are used interchangeably with the protein, as a rule. However, the polypeptide and the peptide may be used to represent a portion of the structure of the protein or to represent a relatively short amino acid chain without assuming a higher order structure (i.e., a fragment of the protein). The polypeptide or the peptide according to the present invention may also include, for example, dipeptide composed of 2 amino acids joined, tripeptide composed of 3 amino acids joined, tetrapeptide composed of 4 amino acids joined, and oligopeptide typically composed of 10 or less amino acids joined.

In the present specification, the "amino acid" is used in the broadest sense and includes natural amino acids, for example, serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gin), threonine (Thr), cysteine (Cys), methionine (Met), phenylalanine (Phe), tryptophan (Trp), and proline (Pro) as well as nonnatural amino acids such as amino acid variants and derivatives. Considering this broad definition, those skilled in the art should naturally understand that examples of the amino acid used in the present specification include: L-amino acids; D-amino acids; chemically modified amino acids such as amino acid variants and amino acid derivatives; amino acids that do not serve as protein constituents in vivo, such as norleucine, β-alanine, and ornithine; and chemically synthesized compounds having the properties of amino acids generally known to those skilled in the art. Examples of the nonnatural amino acids include α-methyl-amino acids (α-methylalanine, etc.), D-amino acids (D-aspartic acid, D-glutamic acid, etc.), histidine-like amino acids (2-amino-histidine, β-hydroxy-histidine, homohistidine, α-fluoromethyl-histidine, α-methyl-histidine, etc.), amino acids having extra methylene in their side chains ("homo"amino acids), and amino acids in which a carboxylic acid functional group amino acid in a side chain is replaced by a sulfonic acid group (cysteic acid, etc.).

In the present specification, the "polynucleotide" includes, but is not limited to: single- or double-stranded DNA or RNA having a 2- to 2000-nucleotide sequence; single- or double-stranded siRNA, miRNA, or nucleic acid (DNA or RNA) aptamers; and chemically modified compounds thereof. Examples of such modification include, but are not limited to, modification with other chemical groups that further impart electric charge, polarizability, hydrogen bond, electrostatic interaction, or fluxionality to the whole or a portion of the polynucleotide. The polynucleotide may be an oligonucleotide having 20 base pairs or a smaller size.

In the present specification, the "peptide nucleic acid" is not limited and means a modified nucleic acid having a N-(2-aminoethyl)glycine backbone converted from the sugar phosphate backbone of a nucleic acid (DNA or RNA). The peptide nucleic acid may be further modified by a method generally known to those skilled in the art.

According to one embodiment, the biopolymer according to the present invention includes, but is not limited to, for example, adrenocorticotropic hormone (ACTH), oxytocin, adenosine deaminase, agalsidase, α1 antitrypsin, α1 protease inhibitor, alteplase, amylin, Symlin, anistreplase, ancrod serine protease, antithrombin III, antitrypsin, aprotinin, asparaginase, atosiban, biphalin, bivalirudin, bone morphogenetic protein, pancreatic trypsin inhibitor, cadherin fragment, calcitonin (e.g., salmon-derived), collagenase, complement C1 esterase inhibitor, conotoxin, cytokine receptor fragment, DNase, dynorphin A, endorphin, enfuvirtide, enkephalin, erythropoietin, exendin (exendin-3 or exendin-4, etc.), factor VII (factor VIIa), factor VIII (factor Villa), factor IX, fibrinolysin, fibroblast growth factor (FGF), growth hormone-releasing peptide 2 (GHRP-2), follicle-stimulating hormone, gramicidin, ghrelin, desacyl ghrelin, granulocyte colony-stimulating factor (G-CSF), galactosidase, glucagon, glucagon-like peptide (exenatide, GLP-1, GLP-2, etc.), glucocerebrosidase, granulocyte macrophage colony-stimulating factor (GM-CSF), heat shock protein (HSP), phospholipase-activating protein (PLAP), chorionic gonadotropin, hemoglobin, hirudin, human serine protease inhibitor, hyaluronidase, iduronidase, immunoglobulin (IgG Fc region, etc.), interleukin (1α, 1β, 2, 3, 4, 5, 7, 8, 9, 10, 11, 12, 13, 14, 15, 17, 18, or 21, etc.), IL-1 receptor antagonist (IL-1ra), insulin, insulin-like growth factor, insulin-like growth factor-binding protein (IGFBP), interferon (α (α2a, α2b, α2c, etc.), β (β1a and β1b), γ (γ1a and γ1b), λ, ω, ε, κ, etc.), intracellular adhesion molecule, keratinocyte growth factor (KGF), P-selectin glycoprotein ligand (PSGL), transforming growth factor, lactase, leptin, leuprolide, luteinizing hormone, natriuretic peptide (ANP, BNP, or CNP, or fragments thereof), neuropeptide Y, pancrelipase, pancreatic polypeptide, papain, parathyroid hormone (parathormone, etc.), platelet-derived growth factor (PDGF), pepsin, peptide YY, platelet-activating factor acetylhydrolase (PAF-AH), prolactin, protein A, protein C, thymosin al, octreotide, selectin, sermorelin, soluble tumor necrosis factor receptor, superoxide dismutase (SOD), somatropin (growth hormone), somatoprim, somatostatin, streptokinase, sucrase, terlipressin, tetanus toxin C fragment, tilactase, thrombin, thymosin, thyroid-stimulating hormone, thyrotropin, tumor necrosis factor (TNF), TNF receptor, tissue plasminogen activator (tPA), thyroid hormone (calcitonin, etc.), urodilatin, urate oxidase, urokinase, hapten, vaccines containing antigens or the like (cancer vaccines, HIV antigens, hepatitis A vaccines, hepatitis B vaccines (HBs antigens, etc.), influenza vaccines, Lyme disease vaccines, etc.), vascular endothelial growth factor (VEGF), chemerin), HER2 protein (human epithelial growth factor receptor), epithelial growth factor (EGF), vasoactive intestinal peptide, vasopressin, ziconotide, lectin, choline esterase, amylase, and pepsin, and variants thereof.

According to one embodiment, examples of the low-molecular physiologically active substance according to the present invention include central nervous system stimulants, anti-infective agents, anti-allergic agents, immune-regulating agents, anti-obesity agents, anticoagulants, antidiabetic agents, anticancer agents, antineoplastic agents, antimicrobial agents, antimycotic agents, analgesics, contraceptives, anti-inflammatory agents, steroids, vasodilators, vasoconstrictors, and cardiovascular agents having at least one amino group, hydroxy group, thiol group, or carboxy group.

According to one embodiment, the low-molecular physiologically active substance according to the present invention includes, but not limited to, for example, acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, amrinone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamide, cephalexin, clinafloxacin, ciprofloxacin, deferoxamine, delavirdine, desipramine, daunorubicin, dexmethylphenidate, dexmethylphenidate, diaphenylsulfone, dizocilpine, dopamine, dobutamine, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecainide, fluvoxamine, fosamprenavir, frovatriptan, furosemide, fluoxetine, gabapentin, gatifloxacin, gemifloxacin, gentamycin, grepafloxacin, hexylcaine, hydralazine, hydrochlorothiazide, icofungipen, idarubicin, imiquimod, isoproterenol, isradipine, kanamycin A, ketamine, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantrone, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazine, sulfamerazine, sertraline, spectinomycin, sulfalene, sulfamethoxazole, tacrine, tamsulosin, terbutaline, timolol, tirofiban, tobramycin, tocainide, tosufloxacin, trandolapril, tranexamic acid, tranylcypromine, trimetrexate, trovafloxacin, valaciclovir, valganciclovir, vancomycin, viomycin, viloxazine, zalcitabine, penicillin, cephalosporin, streptomycin, destomycin, kasugamycin, tylosin, erythromycin, oleandomycin, spiramycin, lincomycin, colistin, bacitracin, salinomycin, monensin, lasalocid, tetracycline, chloramphenicol, virginiamycin, sulfadimethoxine, oxolinic acid, piromidic acid, difurazone, zearalenone, deoxynivalenol, patulin, fumonisin, ochratoxin, tetrodotoxin, okadaic acid, saxitoxin, and gonyautoxin.

The physiologically active substance moiety according to the present invention is bonded at the at least one amino group, hydroxy group, thiol group, or carboxy group of the physiologically active substance to the glycosylated linker moiety or the linker moiety (non-glycosylated linker moiety). The amino group is preferably a primary amino group or a secondary amino group.

In the present specification, the "glycosylated amino acid" is an amino acid bonded to a sugar chain. The sugar chain and the amino acid may be bonded to each other without the mediation of a linker or may be bonded to each other via a linker. The binding site between the sugar chain and the amino acid is not particularly limited and is preferably the reducing end of the sugar chain to which the amino acid is bonded. The amino acid to be bonded to the sugar chain is not particularly limited by its type, and any of natural amino acids, nonnatural amino acids, and D-amino acids can be used. The glycosylated amino acid is preferably glycosylated Asn as in a N-linked sugar chain, or glycosylated Ser or glycosylated Thr as in an O-linked sugar chain, from the viewpoint that the glycosylated amino acid is structurally identical or similar to an in vivo glycopeptide (glycoprotein).

When the sugar chain and the amino acid are bonded to each other via a linker, the amino acid in the glycosylated amino acid is preferably an amino acid having two or more carboxy groups in the molecule, such as aspartic acid or glutamic acid; an amino acid having two or more amino groups in the molecule, such as lysine, arginine, asparagine, histidine, or tryptophan; an amino acid having a hydroxy group in the molecule, such as serine, threonine, or tyrosine; an amino acid having a thiol group in the molecule, such as cysteine; or an amino acid having an amide group in the molecule, such as asparagine or glutamine, from the viewpoint of easy bonding to the linker. Particularly, the amino acid in the glycosylated amino acid is preferably aspartic acid, glutamic acid, lysine, arginine, serine, threonine, cysteine, asparagine, or glutamine, more preferably cysteine or asparagine, from the viewpoint of reactivity.

When the sugar chain and the amino acid are bonded to each other via a linker, any linker used in the art can be widely used. Examples of the linker can include:

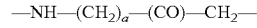
—NH—(CH$_2$)$_a$—(CO)—CH$_2$— wherein a represents an integer and is preferably an integer of 0 to 4, though there is no limitation unless it inhibits the linker functions of interest; C$_{1-10}$ polymethylene;

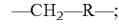
—CH$_2$—R—;

wherein R represents a group formed by the elimination of one hydrogen atom from a group selected from the group including substituted or unsubstituted alkyl, substituted or unsubstituted alkenyl, substituted or unsubstituted alkynyl, substituted or unsubstituted aryl, a substituted or unsubstituted carbocyclic group, and a substituted or unsubstituted heterocyclic ring group; and

—(CO)—(CH$_2$)$_a$—(CO)— wherein a represents an integer and is preferably an integer of 0 to 4, though there is no limitation unless it inhibits the linker functions of interest.

According to one embodiment, when the sugar chain and the amino acid are bonded without the mediation of a linker in the glycosylated amino acid according to the present invention, for example, a hydrogen atom on the side chain amino group of asparagine may be replaced by the reducing end of the sugar chain. In this case, a leaving group present in the reducing end of the sugar chain is not limited and may be, for example, chlorine, bromine, or fluorine.

According to one embodiment, when the sugar chain and the amino acid are bonded via a linker in the glycosylated amino acid according to the present invention, for example, a hydrogen atom on the side chain thiol group of cysteine may be bonded to the reducing end of the sugar chain via the linker (e.g., in the case of a linker —CH$_2$—CONH—, the reducing end of the sugar chain is bonded to the nitrogen atom in the linker). In this case, a leaving group in the linker bonded to the reducing end of the sugar chain is not limited and may be, for example, chlorine, bromine, or fluorine.

In the present specification, the "glycosylated polypeptide" is not particularly limited as long as the glycosylated polypeptide is a compound in which at least one sugar chain is added to a protein (or polypeptide or peptide). In the present specification, the glycosylated polypeptide is used interchangeably with a "glycoprotein" or a "glycopeptide". The glycosylated polypeptide may be a polypeptide containing the glycosylated amino acid mentioned above. The binding manner between the sugar chain and the amino acid in the glycosylated polypeptide, and the types of amino acids constituting the polypeptide, etc., may be defined similarly to those in the glycosylated amino acid according to the present invention. The amino acid (residue) at which the polypeptide is bonded to the sugar chain is not limited to the N or C terminus of the polypeptide and may be any appropriate amino acid (residue) constituting the polypeptide. The amino acid residues in the glycosylated polypeptide according to the present invention may be preferably 2 to 100 amino acid residues, more preferably 2 to 10 amino acid residues. In the glycosylated polypeptide according to the present invention, the amino acids other than the amino acid at which the polypeptide is bonded to the sugar chain can be relatively arbitrarily selected. Those skilled in the art understand that according to one embodiment, the amino acid at which the polypeptide is bonded to the sugar chain is, for example, asparagine, cysteine, glutamine, or lysine, while the amino acids other than the amino acid at which the polypeptide is bonded to the sugar chain (e.g., an amino acid to be bonded to the (glycosylated) linker moiety) are not particularly limited.

The amino acid constituting the glycosylated amino acid or the glycosylated polypeptide according to the present invention is preferably an amino acid present in vivo, from the viewpoint of administering the compound of the present invention or the salt thereof into an organism.

In the present specification, the "sugar chain" includes a compound composed of two or more unit sugars (monosaccharides and/or derivatives thereof) linked as well as a compound consisting of one unit sugar (monosaccharide and/or derivative thereof). Examples of such a sugar chain include, but are not limited to, monosaccharides and polysaccharides (glucose, galactose, mannose, fucose, xylose, N-acetylglucosamine, N-acetylgalactosamine, sialic acid, and complexes and derivatives thereof) contained in vivo as well as degraded polysaccharides and sugar chains degraded or induced from complex biomolecules including glycoproteins, proteoglycans, glycosaminoglycans, and glycolipids. When two or more unit sugars are linked, the unit sugars may be bonded to each other by dehydration condensation through a glycoside bond. The sugar chain may be linear or may be branched.

In the present specification, the "sugar chain" also includes derivatives of the sugar chain. Examples of the sugar chain derivatives include, but are not limited to, sugar chains constituted by sugars which are sugars having a carboxy group (e.g., aldonic acid which is carboxylic acid derived from oxidation at the C1 position (e.g., D-gluconic acid oxidized from D-glucose) and uronic acid which is carboxylic acid derived from a terminal C atom (D-glucuronic acid oxidized from D-glucose)), sugars having an amino group or an amino group derivative (e.g., an acetylated amino group) (e.g., N-acetyl-D-glucosamine and N-acetyl-D-galactosamine), sugars having both an amino group and a carboxy group (e.g., N-acetylneuraminic acid (sialic acid) and N-acetylmuramic acid), deoxidized sugars (e.g., 2-deoxy-D-ribose), sulfated sugars containing a sulfuric acid group, and phosphorylated sugars containing a phosphoric acid group.

According to one embodiment, the sugar chain according to the present invention may be a sugar chain that is present as a glycoconjugate (glycoprotein (or glycopolypeptide), proteoglycan, or glycolipid, etc.) in vivo. Alternatively, according to another embodiment, the sugar chain may be a carbohydrate that is not present as a glycoconjugate in vivo.

The sugar chain that is present as a glycoconjugate in vivo is preferred from the viewpoint of administering the compound of the present invention or the salt thereof to an organism. Examples of such a sugar chain include, but are not limited to, N-linked sugar chains and O-linked sugar chains, which are sugar chains bonded to proteins to form glycoproteins in vivo. In the glycoprotein having an O-linked sugar chain, for example, N-acetylgalactosamine (GalNAc), N-acetylglucosamine (GlcNAc), xylose, or fucose is bonded through an O-glycoside bond to Ser or Thr of a peptide, and a sugar chain is further added to this sugar residue. Examples of the N-linked sugar chain can include high-mannose-type, complex-type, and hybrid-type. A complex-type N-linked sugar chain is preferred.

Preferred examples of the complex-type sugar chain used in the present invention include sugar chains represented by the following formula:

[Formula 18]

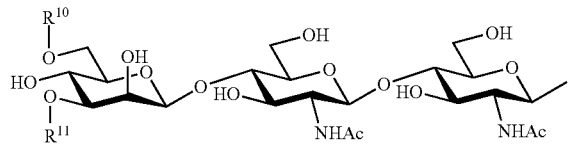

wherein $R^{10}$ and $R^{11}$ are the same or different and each represent

[Formula 19]

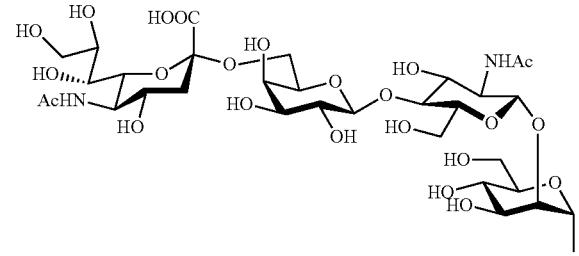

-continued

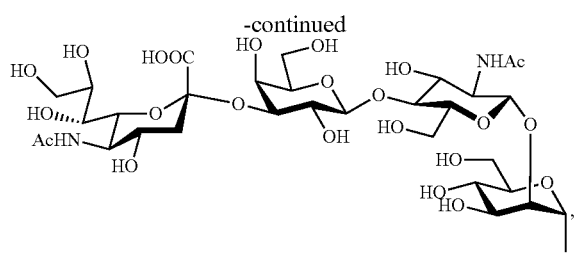

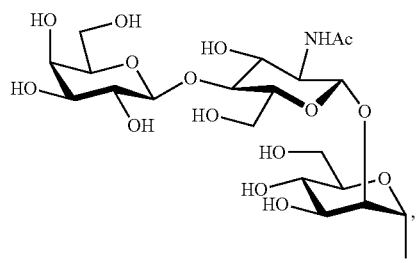

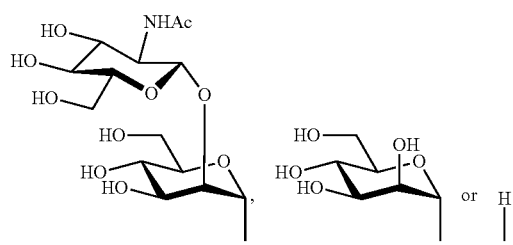

and Ac represents an acetyl group.

According to one embodiment, the sugar chain in the "glycosylated amino acid or glycosylated polypeptide" according to the present invention is preferably a sugar chain consisting of 4 or more, for example, 5 or more, 7 or more, particularly, 9 or more, or 11 or more sugars. The present inventor has found that, surprisingly, a larger number of sugars constituting the added sugar chain further improves the water solubility of the compound of the present invention or the salt thereof, but does not influence its half-life.

According to a preferred embodiment, the sugar chain in the glycosylated amino acid or the glycosylated polypeptide according to the present invention is a biantennary complex-type sugar chain (i.e., a complex-type sugar chain having two branches). A feature of the complex-type sugar chain is to comprise two or more types of monosaccharides and to have a basic structure shown below and a lactosamine structure represented by Galβ1-4GlcNAc, though there is no limitation.

[Formula 20]

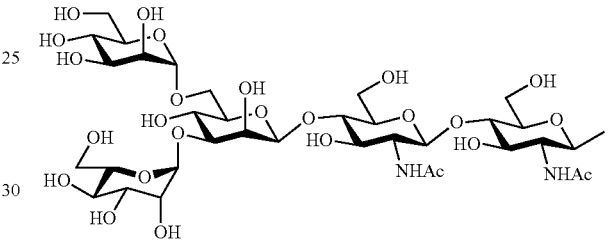

The biantennary complex-type sugar chain is not limited and refers to a sugar chain in which one sugar chain composed of 0 to 3 sugars is bonded to each of two mannose residues at the ends of the basic structure. The biantennary complex-type sugar chain is preferably, for example, a disialo sugar chain shown below:

[Formula 21]

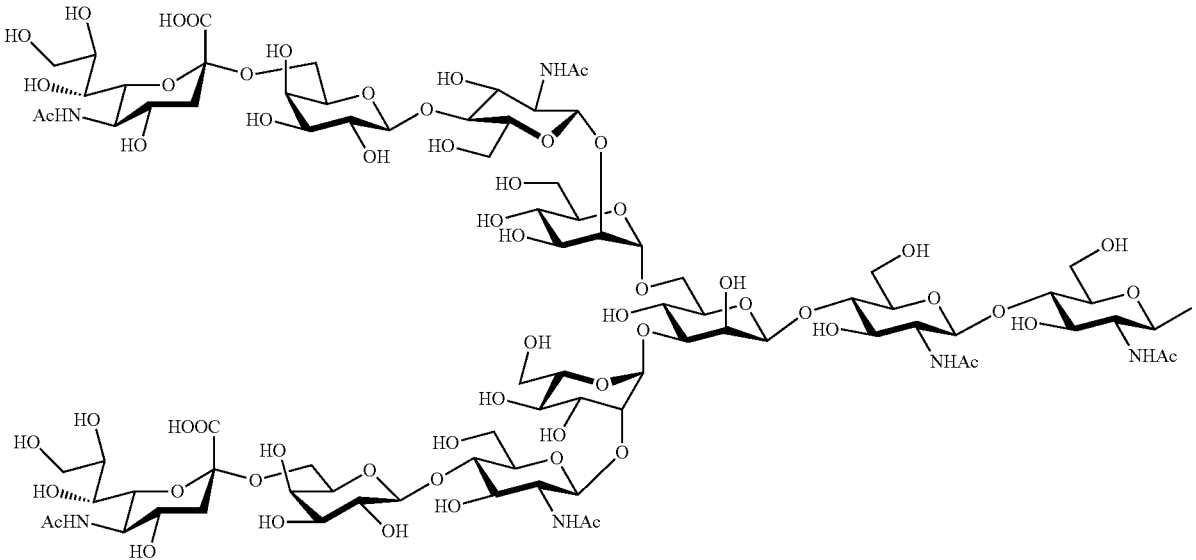

a monosialo sugar chain shown below:
[Formula 22]
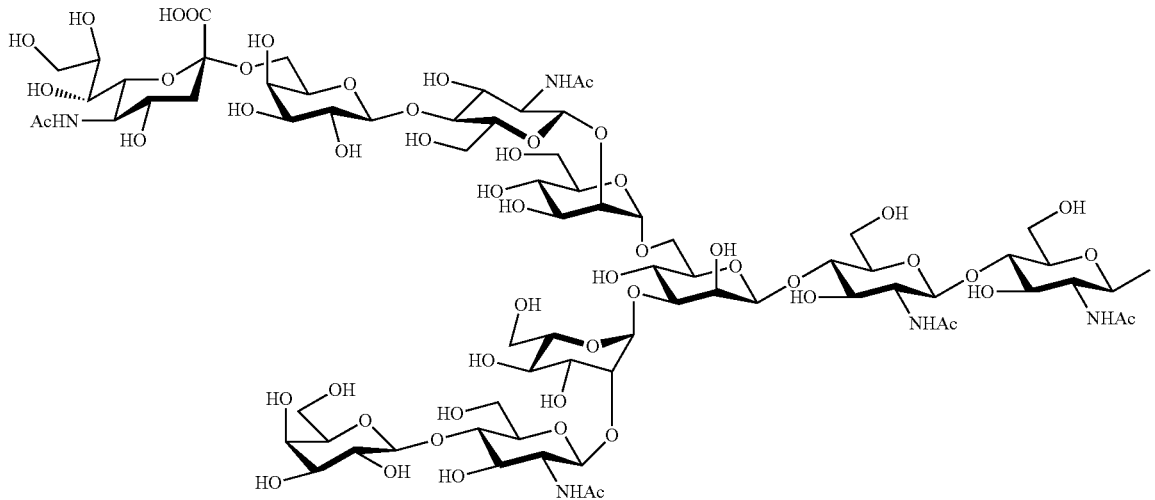
[Formula 23]
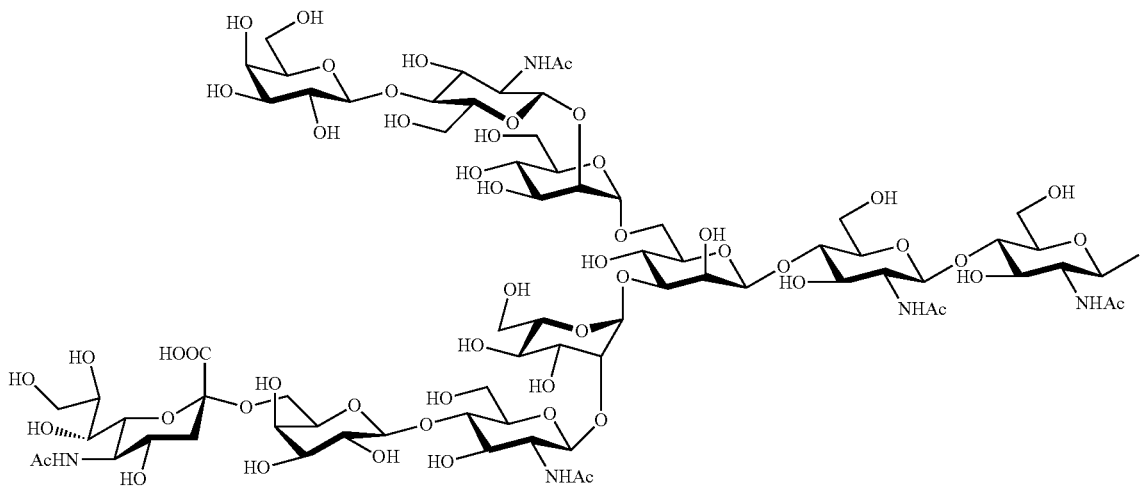

an asialo sugar chain shown below:

[Formula 24]

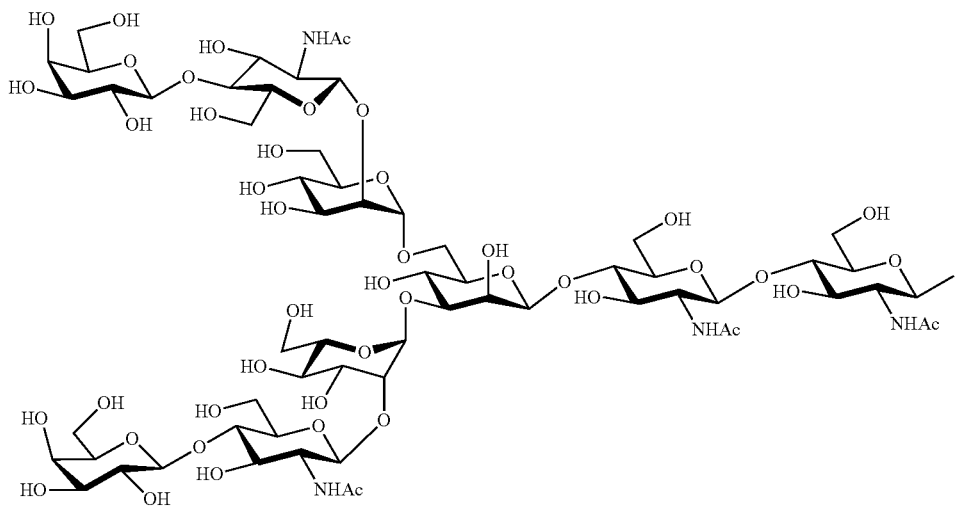

a di-GlcNAc sugar chain shown below:

[Formula 25]

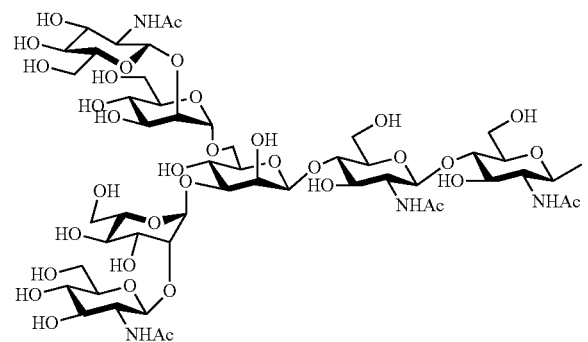

or a dimannose sugar chain shown below:

[Formula 26]

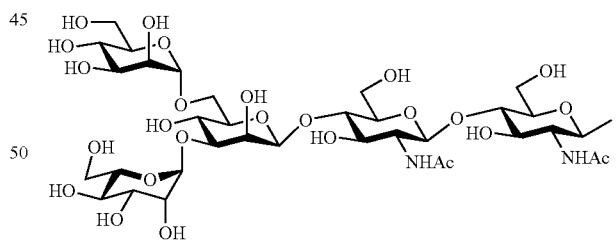

According to another embodiment, the complex-type sugar chain according to the present invention may include, in addition to the biantennary complex-type sugar chain described above, triantennary complex-type sugar chains (complex-type sugar chains having three branches) and tetraantennary complex-type sugar chains (complex-type sugar chains having four branches). Examples of the triantennary and tetraantennary complex-type sugar chains can include, but are not limited to, trisialo sugar chains shown below:

[Formula 27]
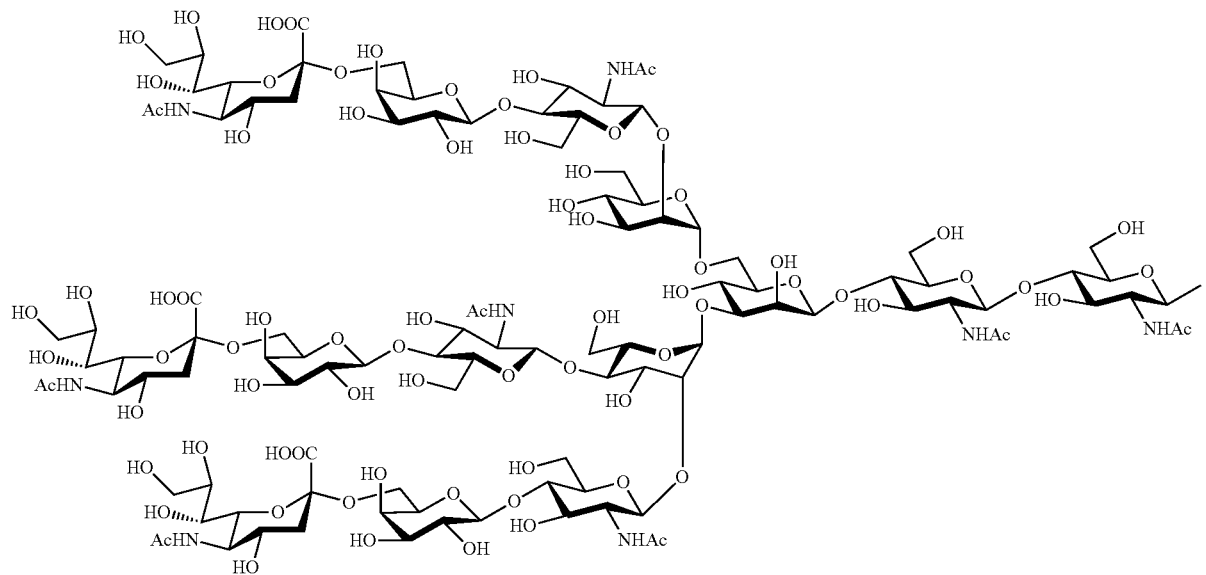
[Formula 28]
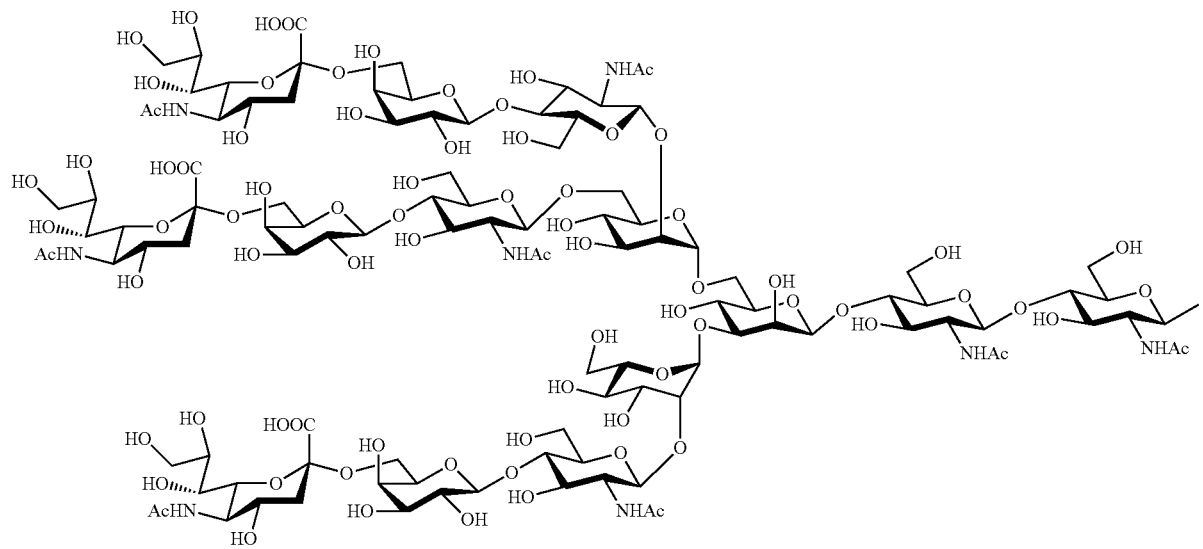

and tetrasialo sugar chains shown below:

[Formula 29]

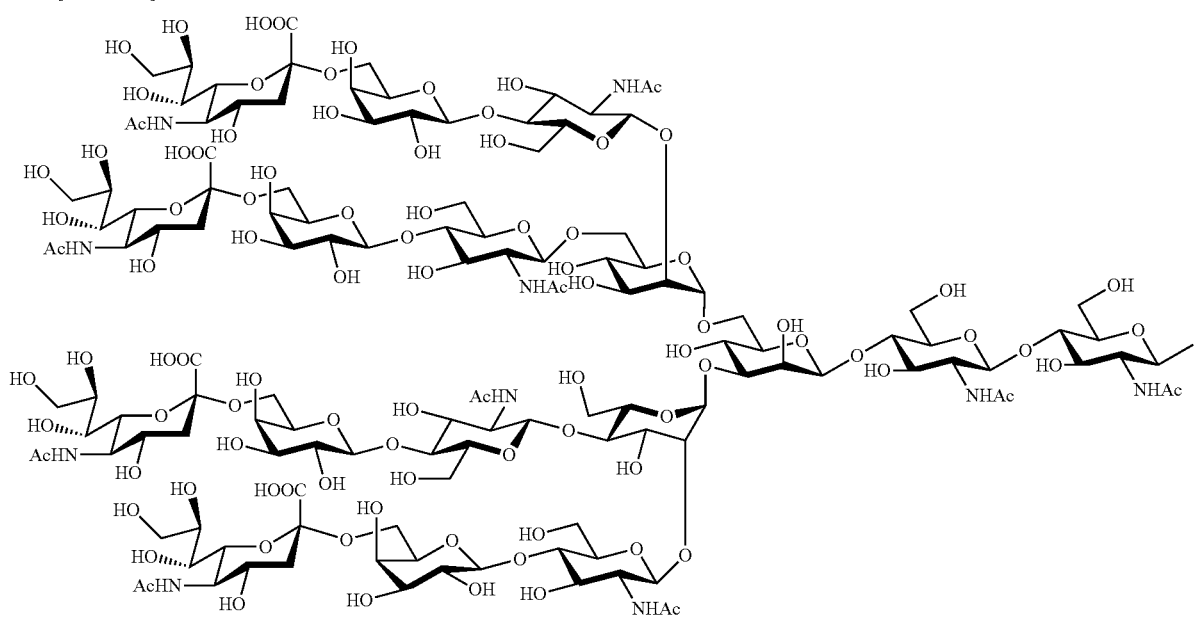

Further examples of the triantennary and tetraantennary complex-type sugar chains can include sugar chains derived from these trisialo sugar chains or tetrasialo sugar chains by the deletion of one or more sugars from the non-reducing end.

According to an alternative embodiment, the sugar chain according to the present invention may be a high-mannose-type sugar chain. The high-mannose-type sugar chain used in the present invention is a sugar chain in which two or more mannose residues are further bonded to the basic structure of the complex-type sugar chain mentioned above. The high-mannose-type sugar chain is preferably a sugar chain containing 5 to 9 mannose residues as found in mammals and may be a sugar chain containing a larger number of mannose residues as found in yeasts. Examples of the high-mannose-type sugar chain preferably used in the present invention can include high-mannose-5 (M-5) shown below:

[Formula 30]

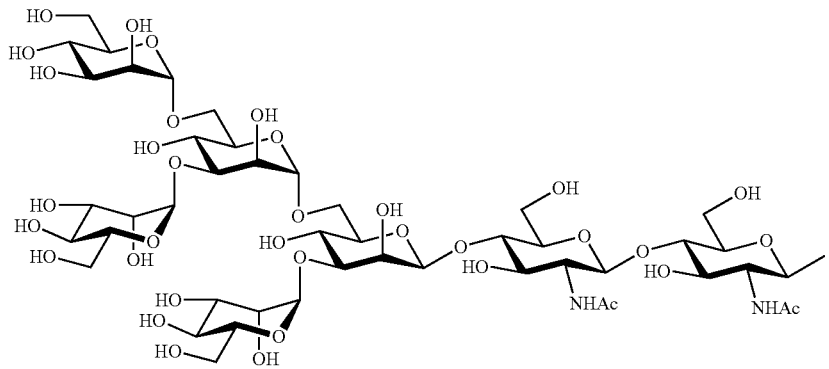

and high-mannose-9 (M-9) shown below:

[Formula 31]

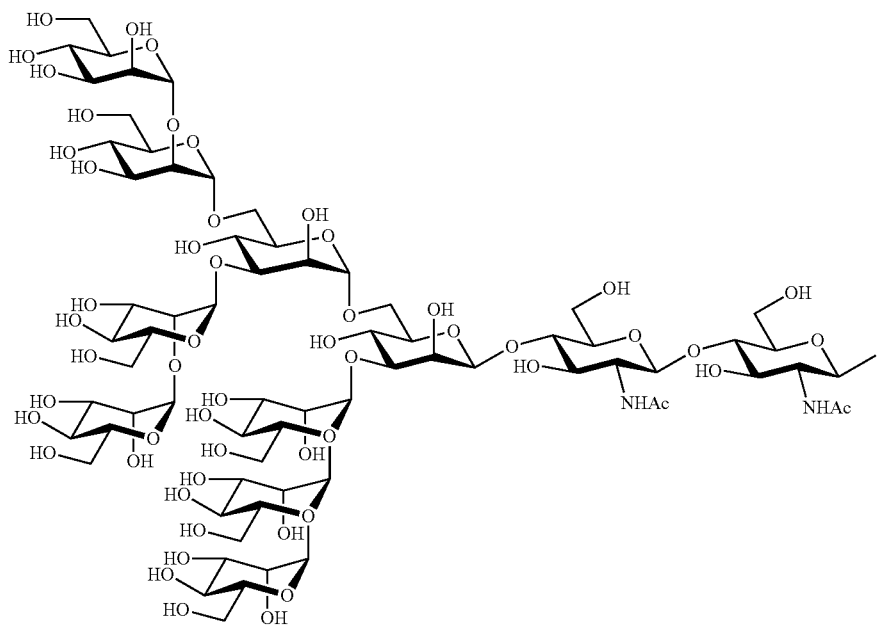

According to an alternative embodiment, the sugar chain according to the present invention may be a sugar chain having a linear structure. Examples of such a sugar chain include oligohyaluronic acid. The oligohyaluronic acid according to the present invention is not limited and may be a sugar chain in which 4 to 32 sugars, preferably 4 to 16 sugars, more preferably 4 to 8 sugars, alternating between N-acetylglucosamine and glucuronic acid are bonded in a linear form. Particularly preferred examples of the oligohyaluronic acid used in the present invention include sugar chains of 2 units (4 sugars) or more and 8 units (16 sugars) or less when a unit consisting of N-acetylglucosamine and glucuronic acid is defined as 1 unit. A sugar chain of 2 units (4 sugars) to 4 units (8 sugars) is further preferred, and a sugar chain of 2 units (4 sugars) is most preferred.

Examples of the hyaluronic acid preferably used in the present invention include
oligohyaluronic acid of 4 sugars shown below:

[Formula 32]

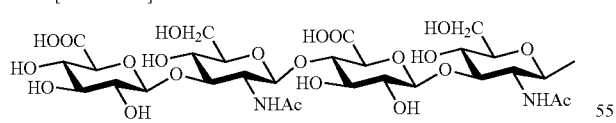

and oligohyaluronic acid of 8 sugars shown below:

[Formula 33]

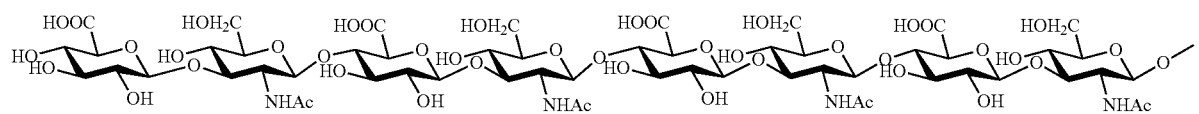

According to a further alternative embodiment, examples of the complex-type sugar chain according to the present invention can include various sugars (e.g., fucose) attached to sugar chains. For example, at least one more fucose residues may be added to N-acetylglucosamine at the non-reducing end of the sugar chain (biantennary complex-type sugar chain, triantennary complex-type sugar chain, tetraantennary complex-type sugar chain, etc.).

Examples of the fucose-attached complex-type sugar chain (fucose-containing complex-type sugar chain) can include, but are not limited to, fucose-containing complex-type sugar chains shown below:

[Formula 34]

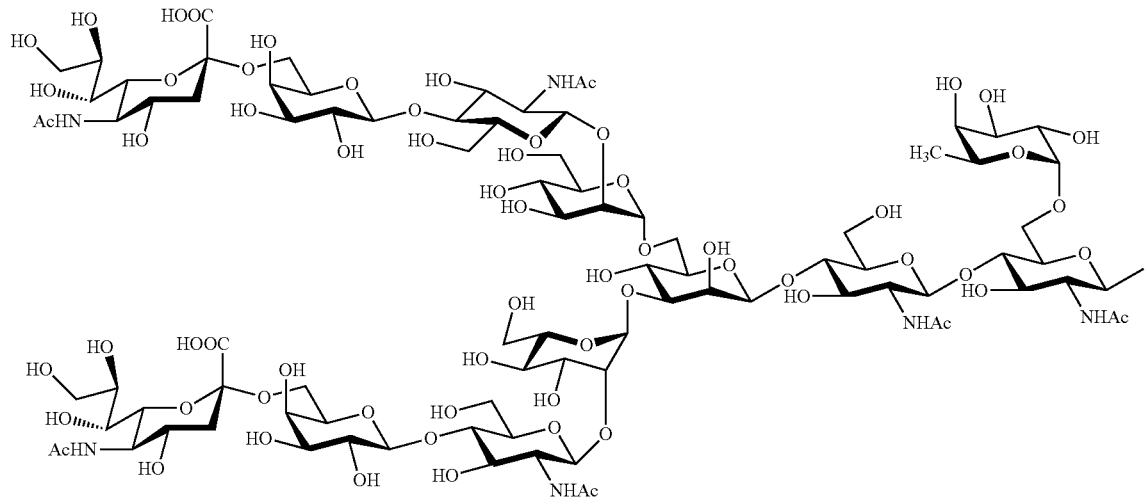

[Formula 35]

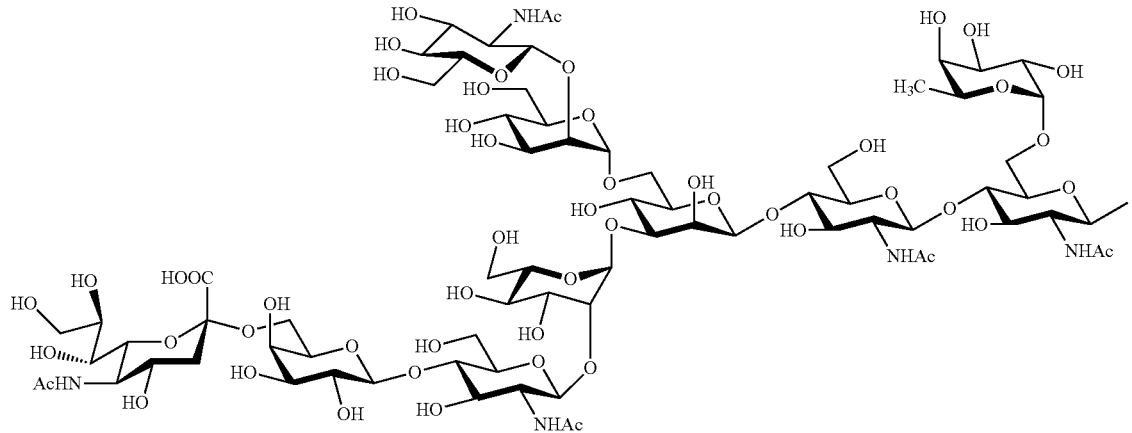

[Formula 36]
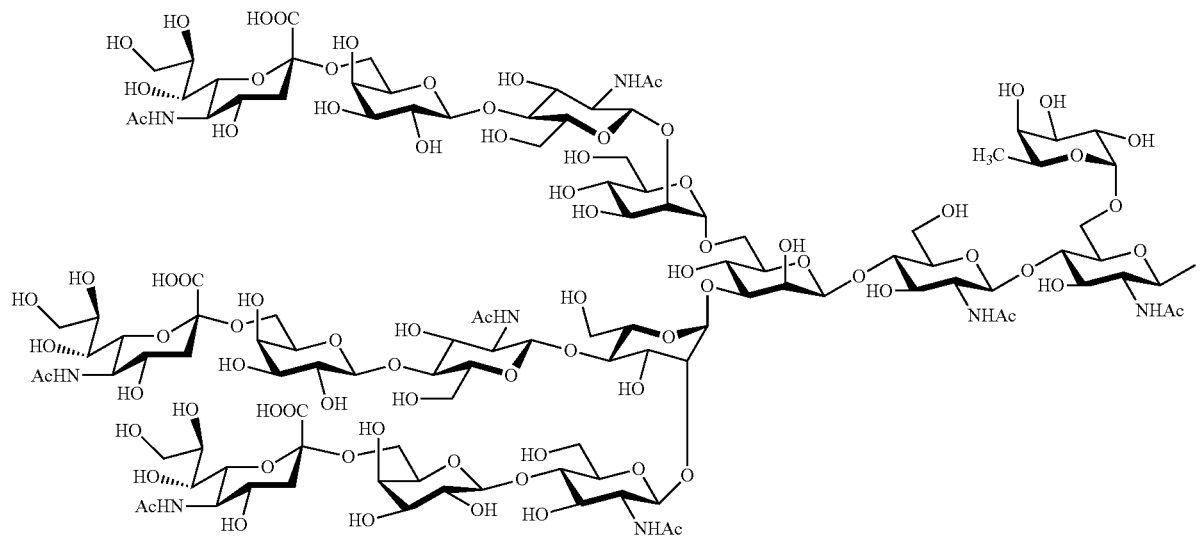
[Formula 37]
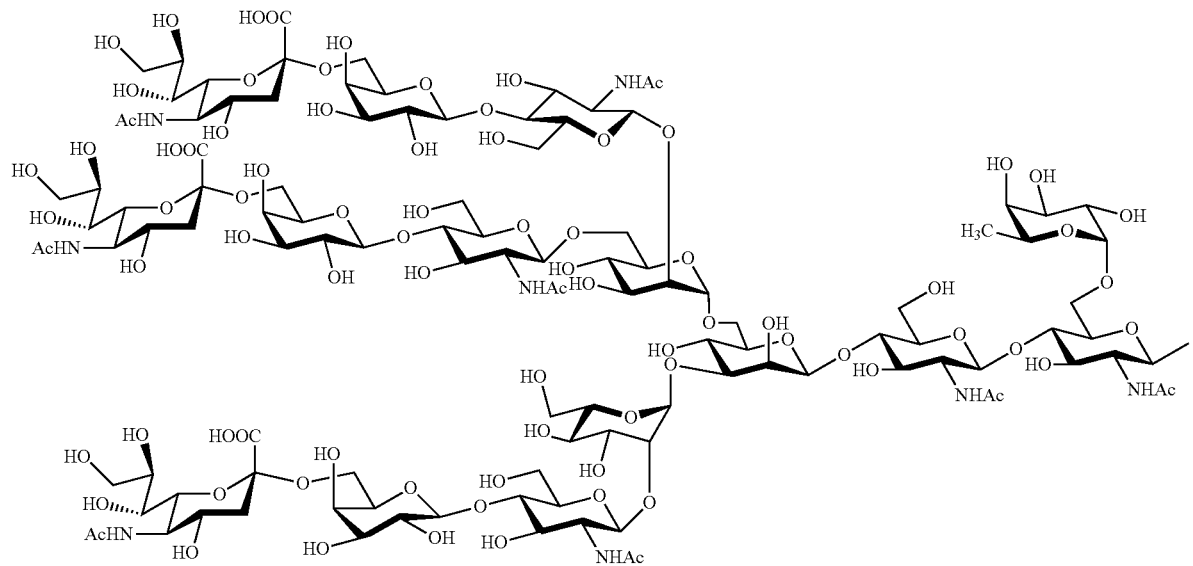

[Formula 38]

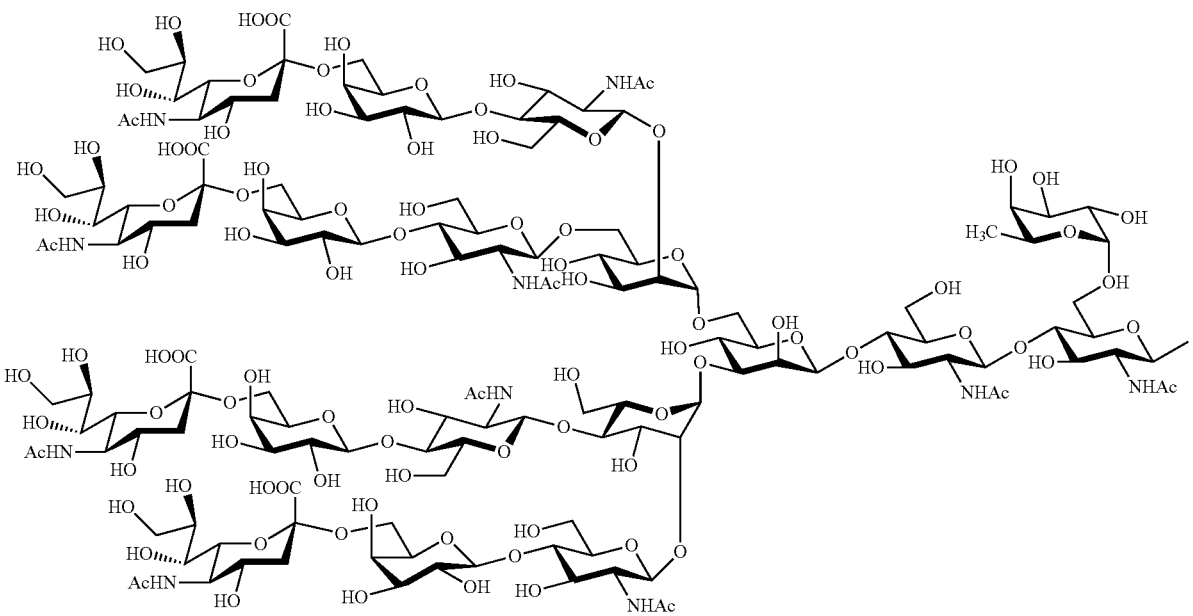

Further examples thereof can include sugar chains derived from these fucose-containing complex-type sugar chains by the deletion of one or more sugars from the non-reducing end.

According to an alternative embodiment, typical examples of the complex-type sugar chain of the present invention can also include sugar chains having a polylactosamine structure or a sialylpolylactosamine structure represented by the following formula:

[Formula 39]

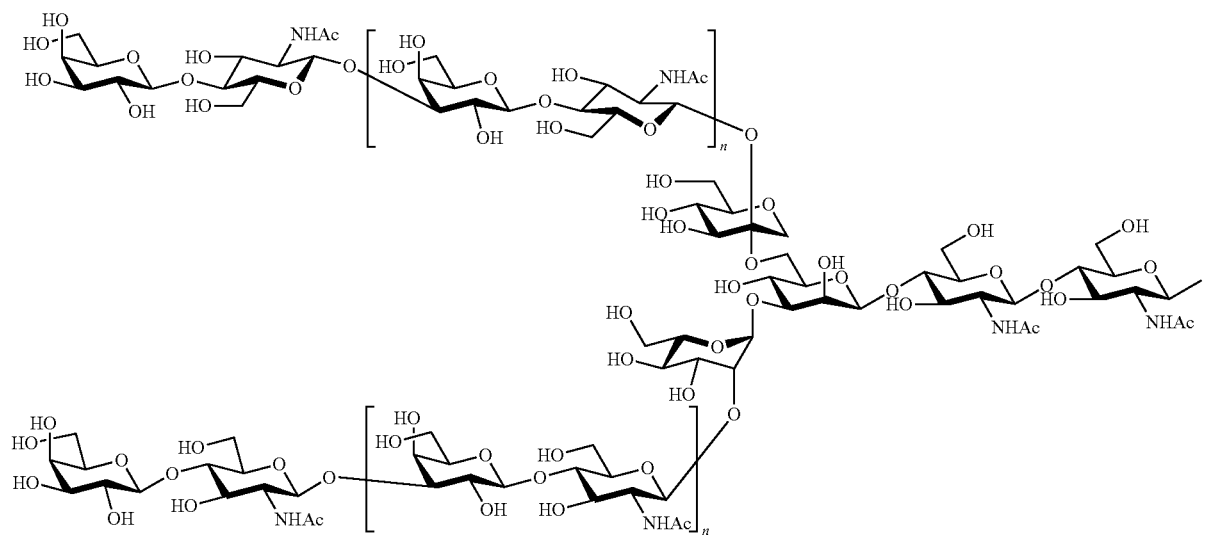

wherein n represents an integer of 2 to 3

[Formula 40]

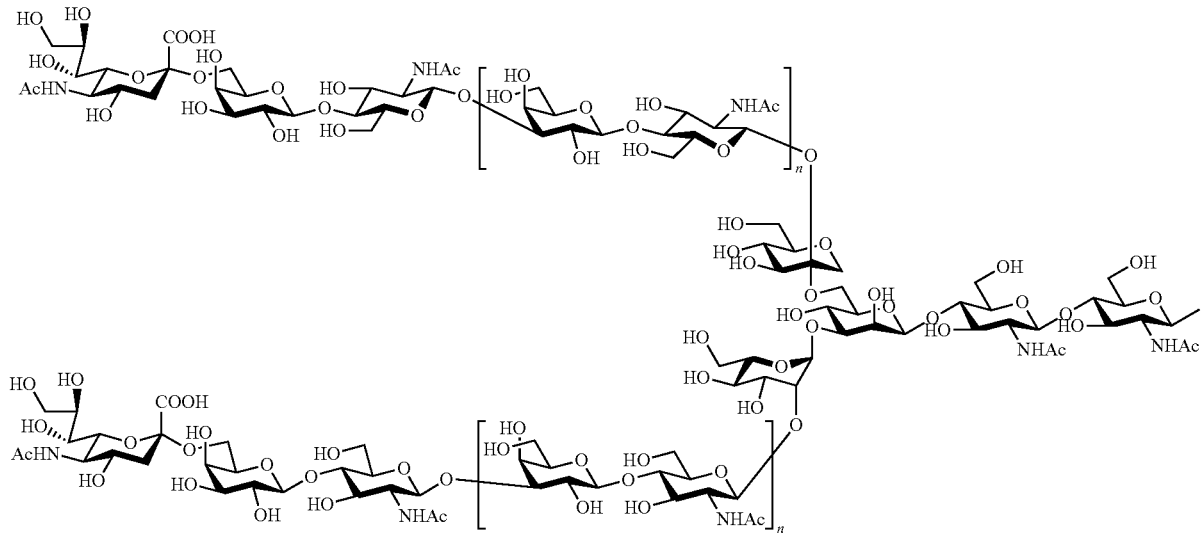

wherein n represents an integer of 2 to 3.

Further examples thereof can include sugar chains derived from these sugar chains having a polylactosamine structure or a sialylpolylactosamine structure by the deletion of one or more sugars from the non-reducing end.

In the present invention, the biantennary complex-type sugar chain, the triantennary complex-type sugar chain, the tetraantennary complex-type sugar chain, the high-mannose-type sugar chain, the oligohyaluronic acid, the fucose-containing complex-type sugar chain, the sugar chain having a polylactosamine structure, and the sugar chain having a sialylpolylactosamine structure also include sugar chains differing in binding pattern from the examples represented by the chemical formulas, in addition to those specifically shown in the chemical formulas in the present specification. Such a sugar chain is also preferably used as the sugar chain according to the present invention. Examples of such a sugar chain include disialo sugar chains and monosialo sugar chains in which sialic acid and galactose are bonded through a (α2→3) bond.

For the sugar chains listed above, a hydroxy group and/or a carboxy group in each sugar residue constituting each sugar chain may be protected with a protective group. The protective group is, for example, a protective group generally known to those skilled in the art which is introduced for the purpose of protecting the hydroxy group and/or the carboxy group in the sugar residue through chemical reaction. More specific examples thereof can include, but are not limited to, an alkyl group (methyl group, ethyl group, etc.), a benzyl group, an acyl group (acetyl group, benzoyl group, pivaloyl group, etc.), a tert-butyldimethylsilyl group, a tert-butyldiphenylsilyl group, a phenacyl group, and an allyl group.

In the present invention, preferred examples of the sugar chain can include sugar chains structurally identical (sugar chains identical in the types of constituent sugars and binding patterns thereof) to sugar chains that are bonded to proteins to form glycoproteins in human bodies (e.g., sugar chains described in "FEBS LETTERS Vol. 50, No. 3, February 1975"), and sugar chains derived from these sugar chains by the deletion of one or more sugars from the non-reducing end, i.e., sugar chains shown in Tables 1 to 4 below, from the viewpoint that problems such as antigenicity can be circumvented in light of application to the field of production of medicines etc.

TABLE 1
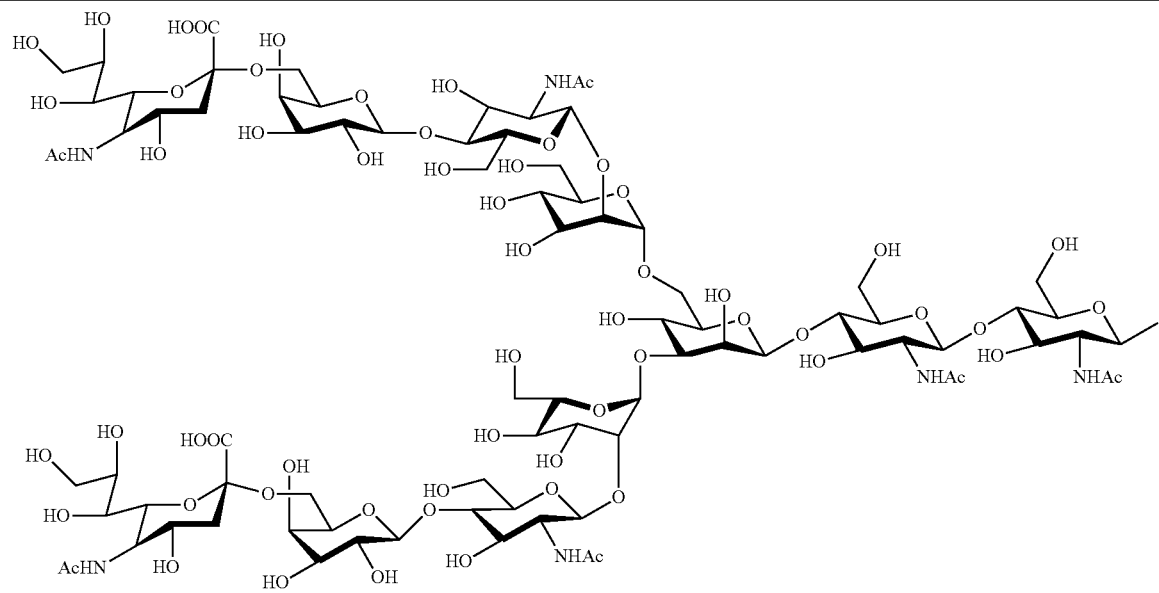
1S2S-11NC, 1
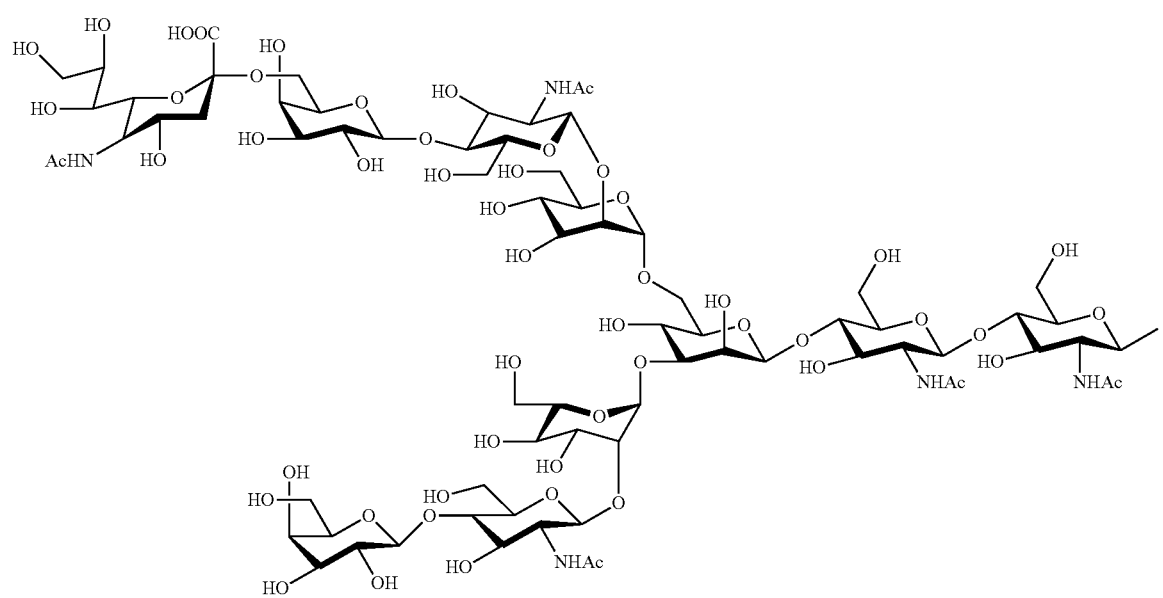
1S2G-10NC, 2

TABLE 1-continued
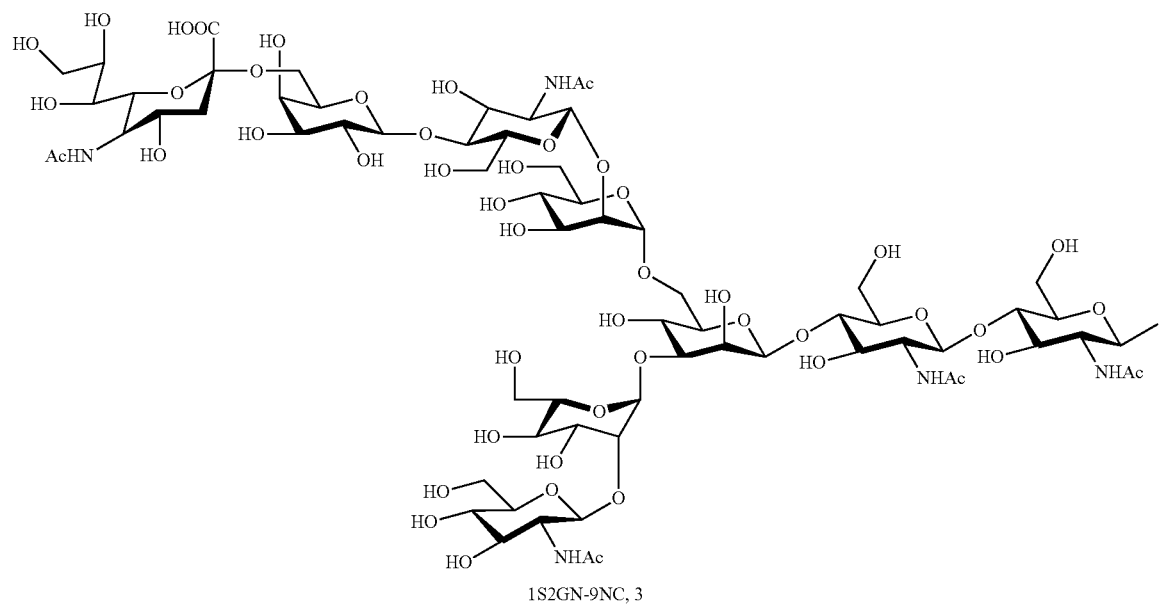
1S2GN-9NC, 3
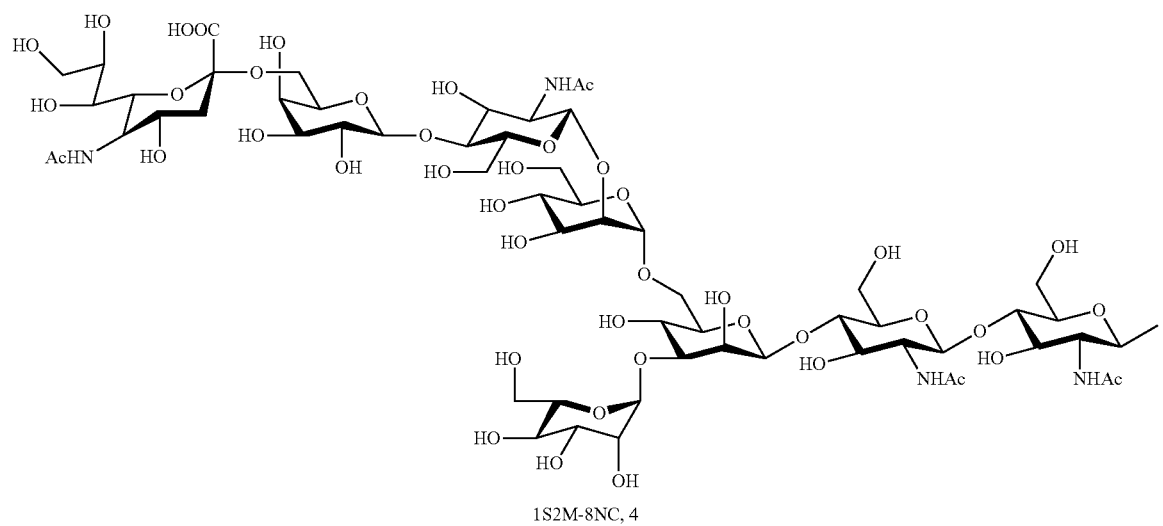
1S2M-8NC, 4
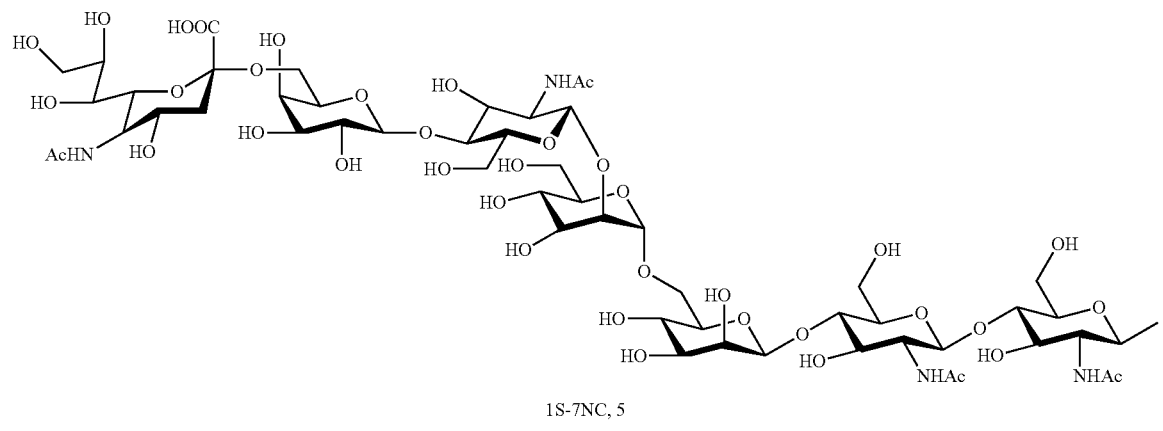
1S-7NC, 5

TABLE 1-continued
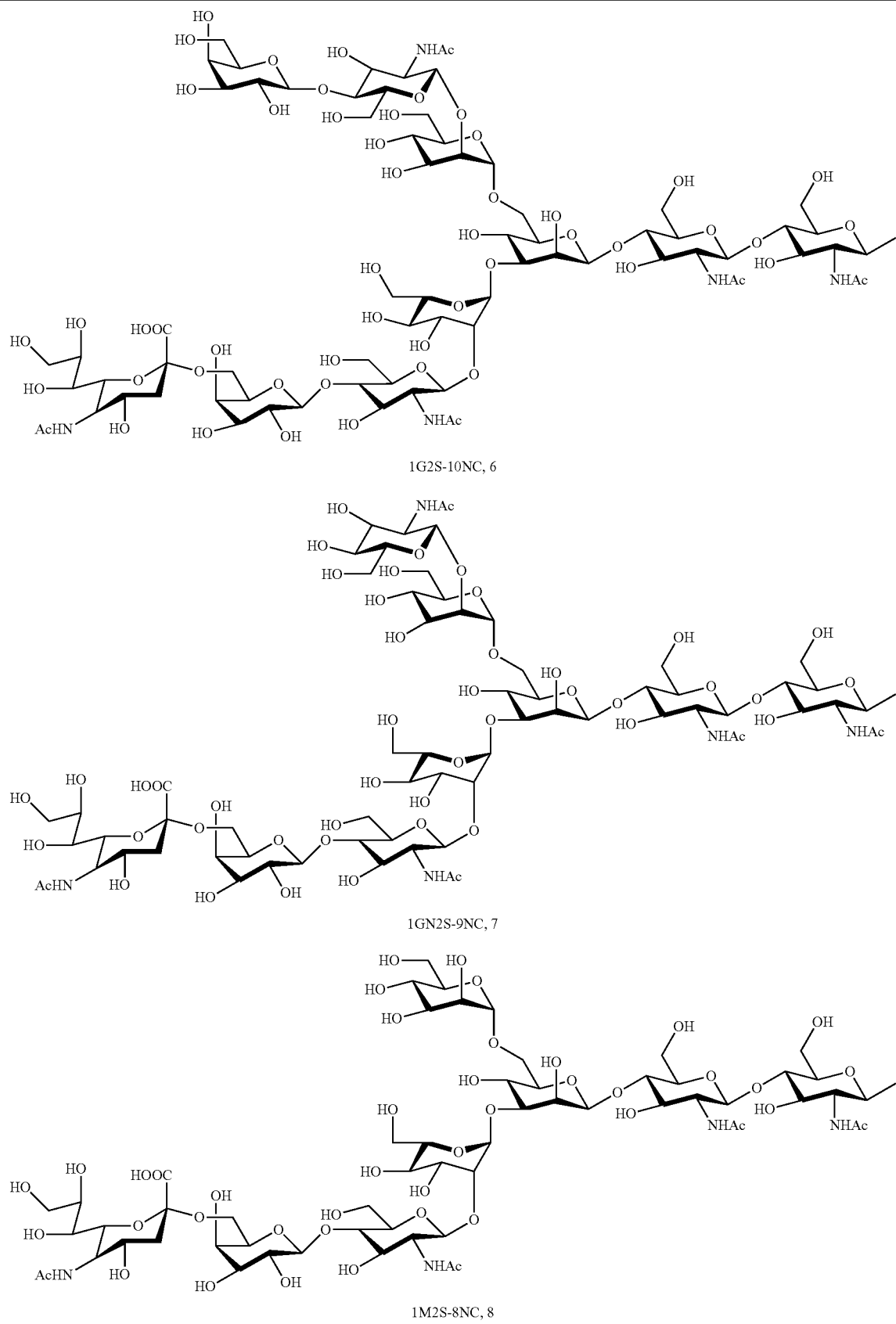
1G2S-10NC, 6
1GN2S-9NC, 7
1M2S-8NC, 8

TABLE 1-continued
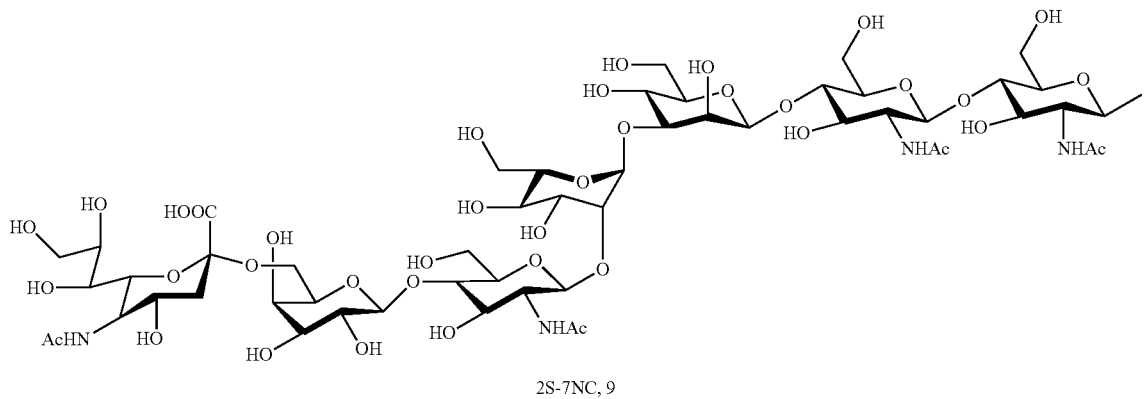
2S-7NC, 9
TABLE 2
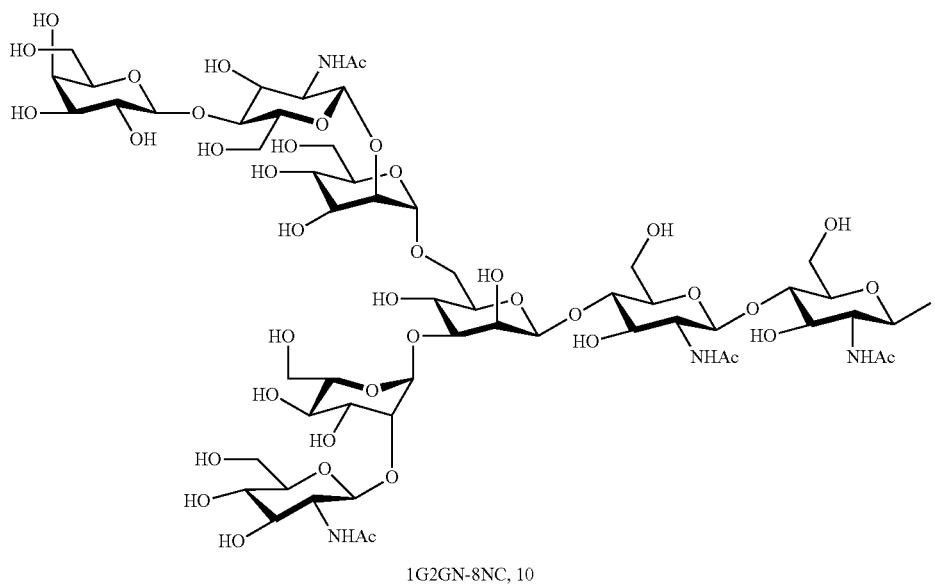
1G2GN-8NC, 10
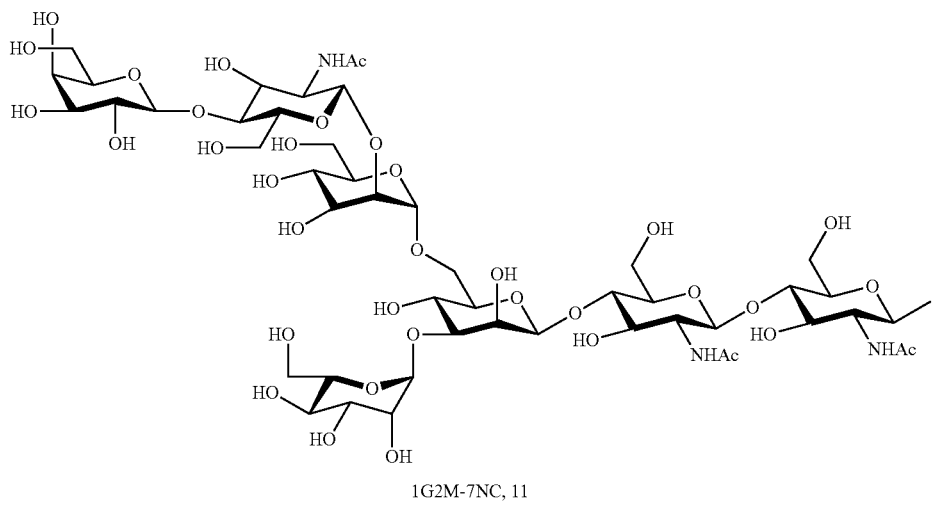
1G2M-7NC, 11

TABLE 2-continued
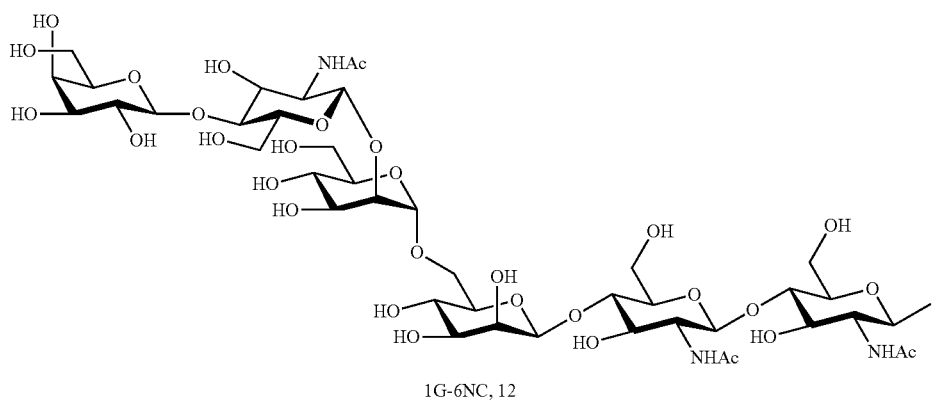
1G-6NC, 12
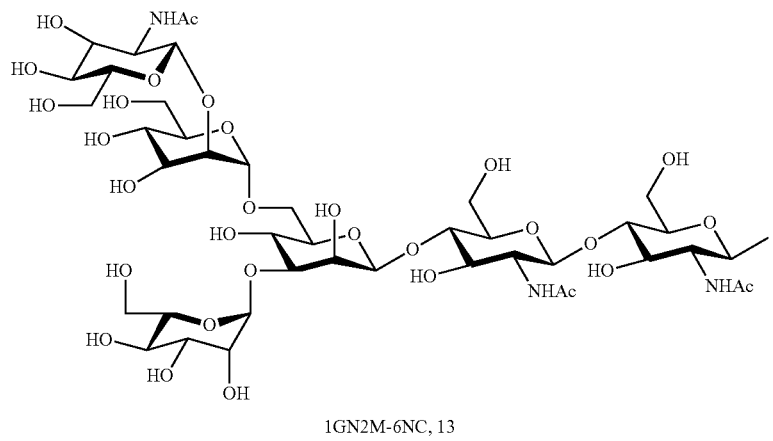
1GN2M-6NC, 13
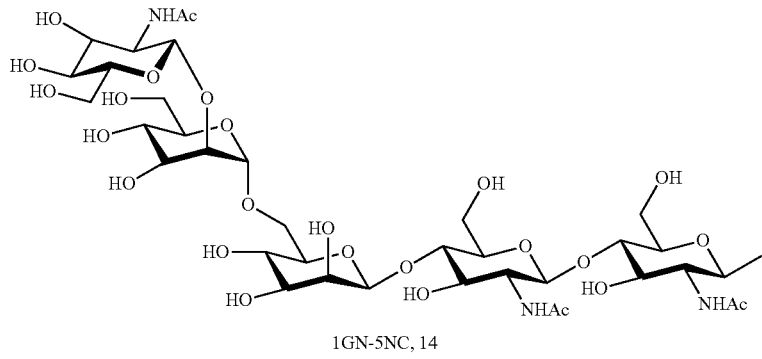
1GN-5NC, 14
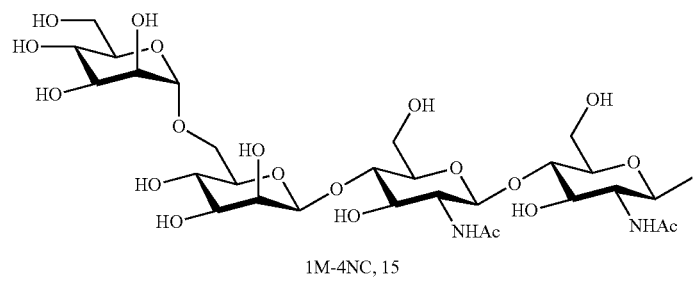
1M-4NC, 15

TABLE 2-continued
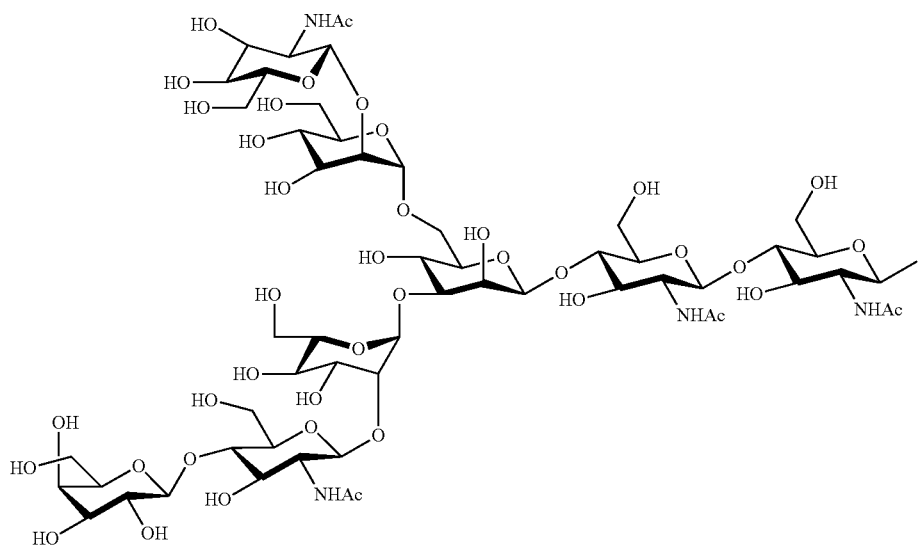
1GN2G-8NC, 16
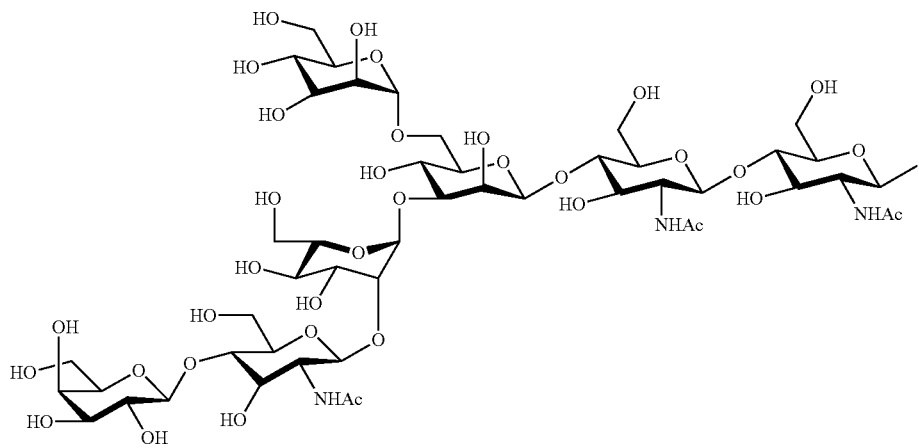
1M2G-7NC, 17
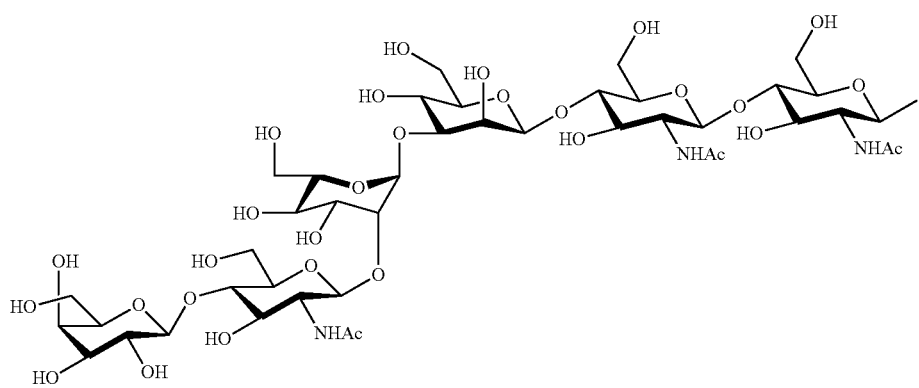
2G-6NC, 18

TABLE 2-continued
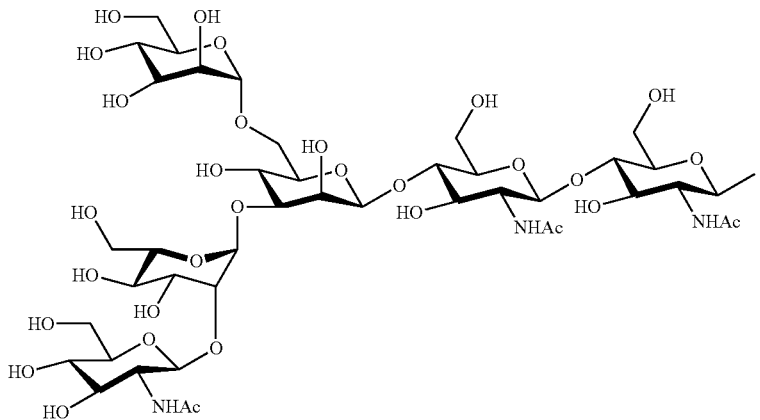
1M2GN-5NC, 19
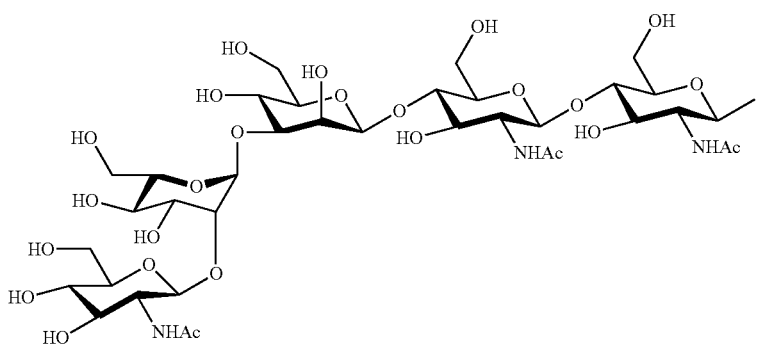
2GN-5NC, 20
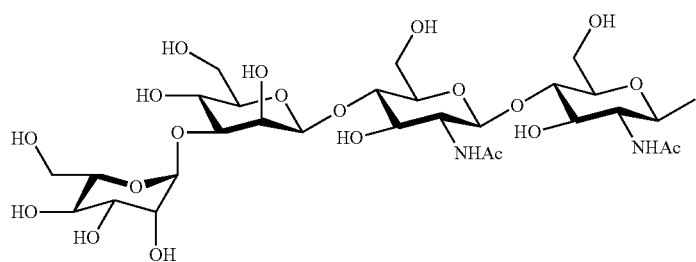
2M-4NC, 21

TABLE 2-continued
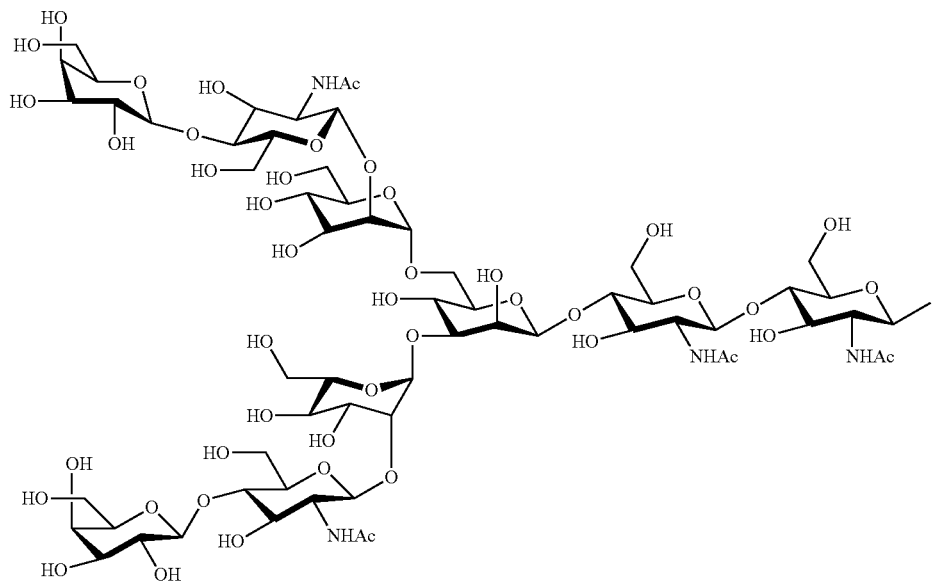
1G2G-9NC, 22
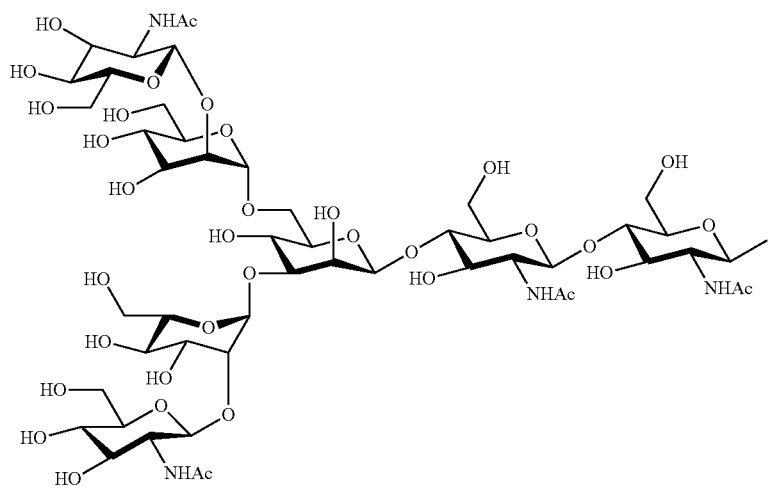
1GN2GN-7NC, 23
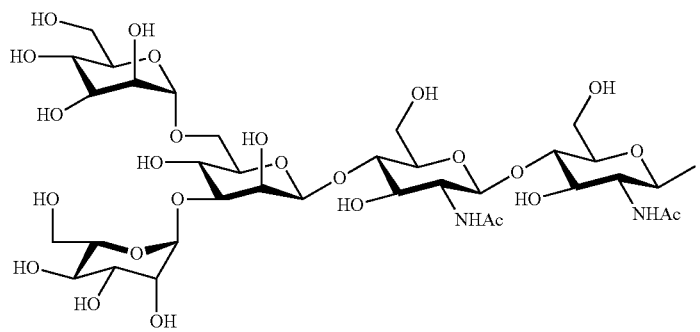
1M2M-5NC, 24

TABLE 3
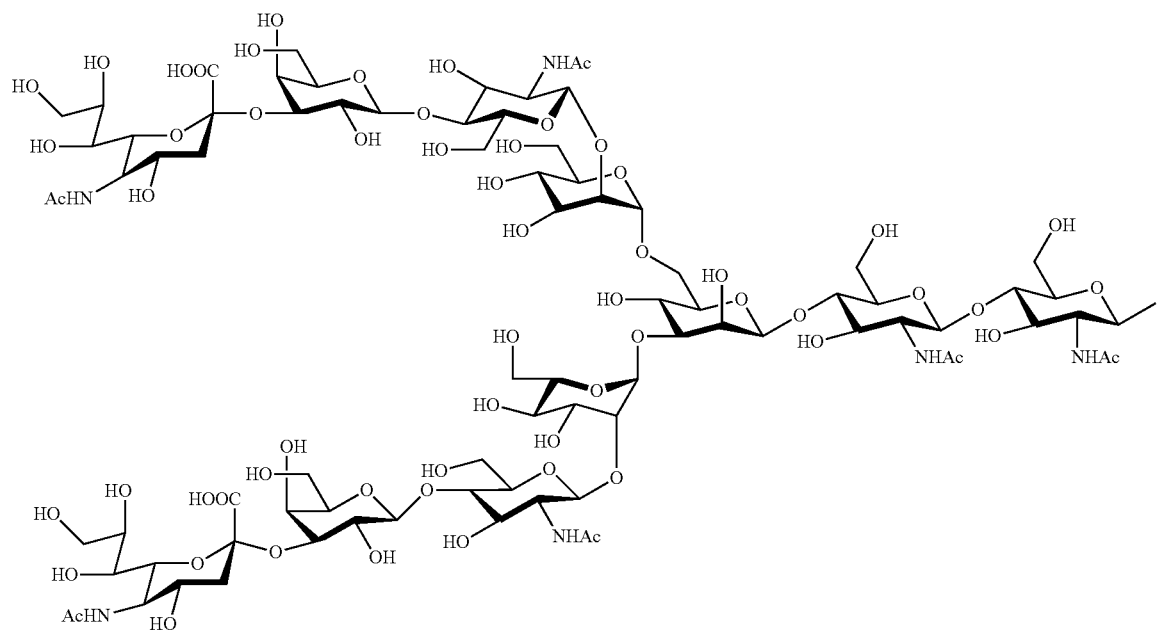
1S(3)2S(3)-11NC, 25
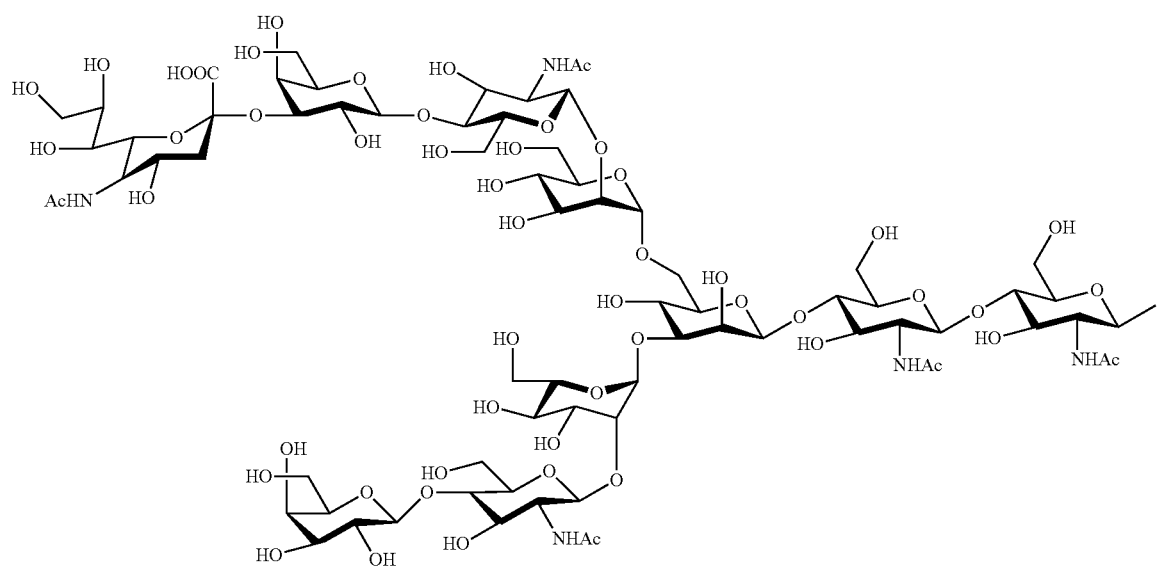
1S(3)2G-10NC, 26

TABLE 3-continued
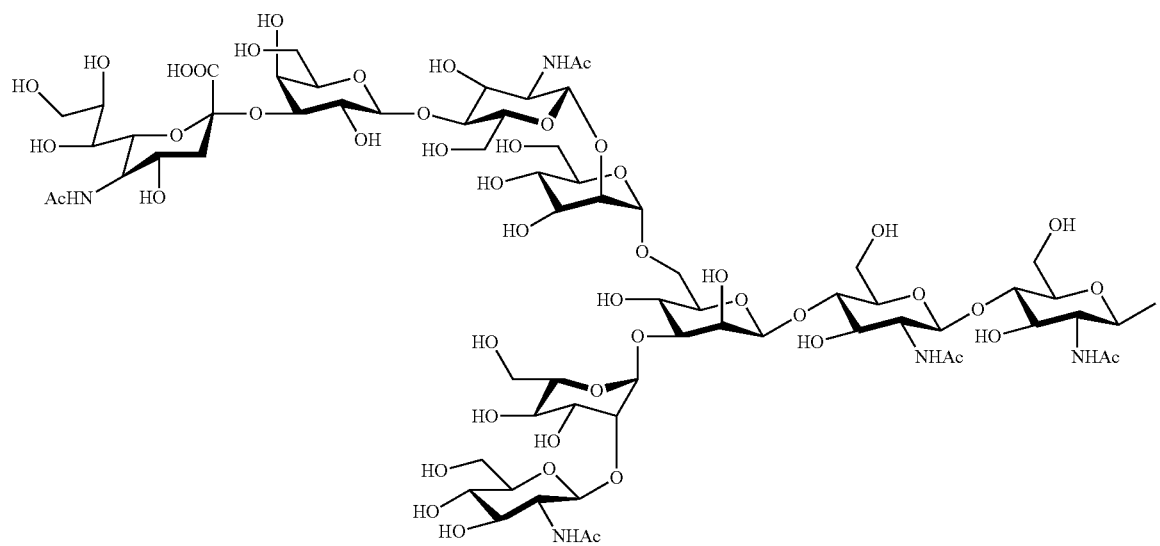
1S(3)2GN-9NC, 27
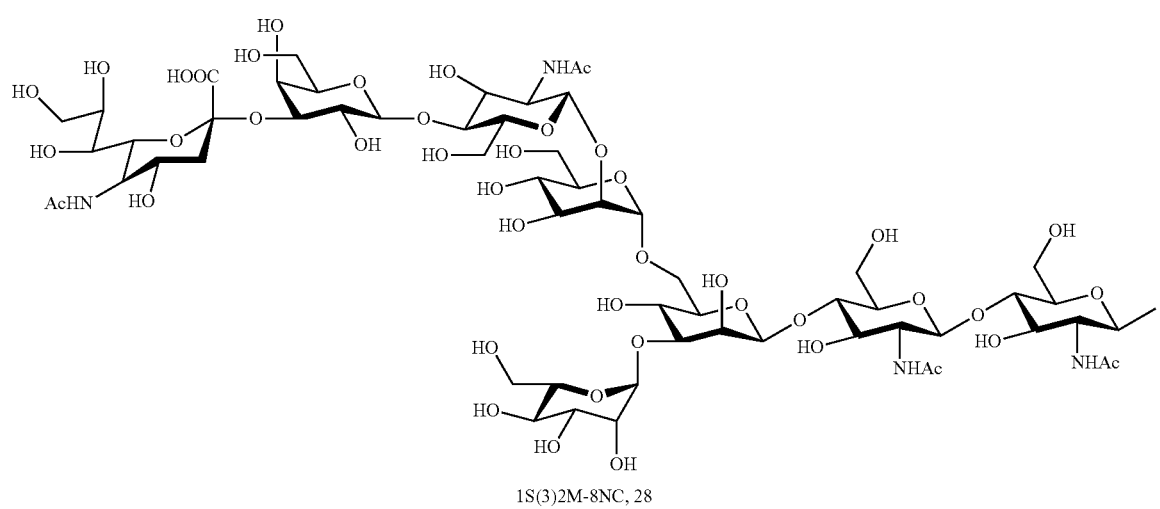
1S(3)2M-8NC, 28
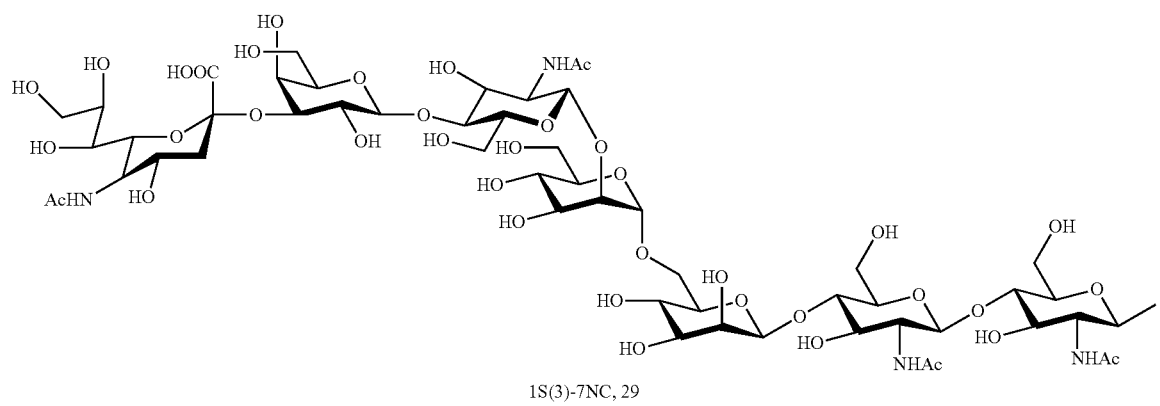
1S(3)-7NC, 29

TABLE 3-continued
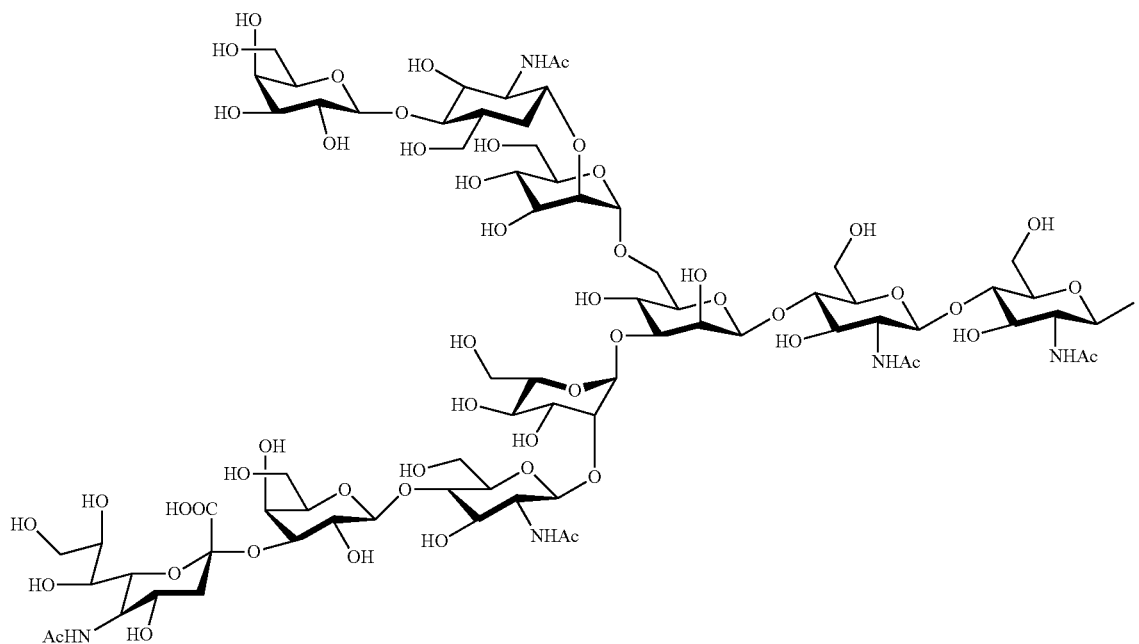
1G2S(3)-10NC, 30
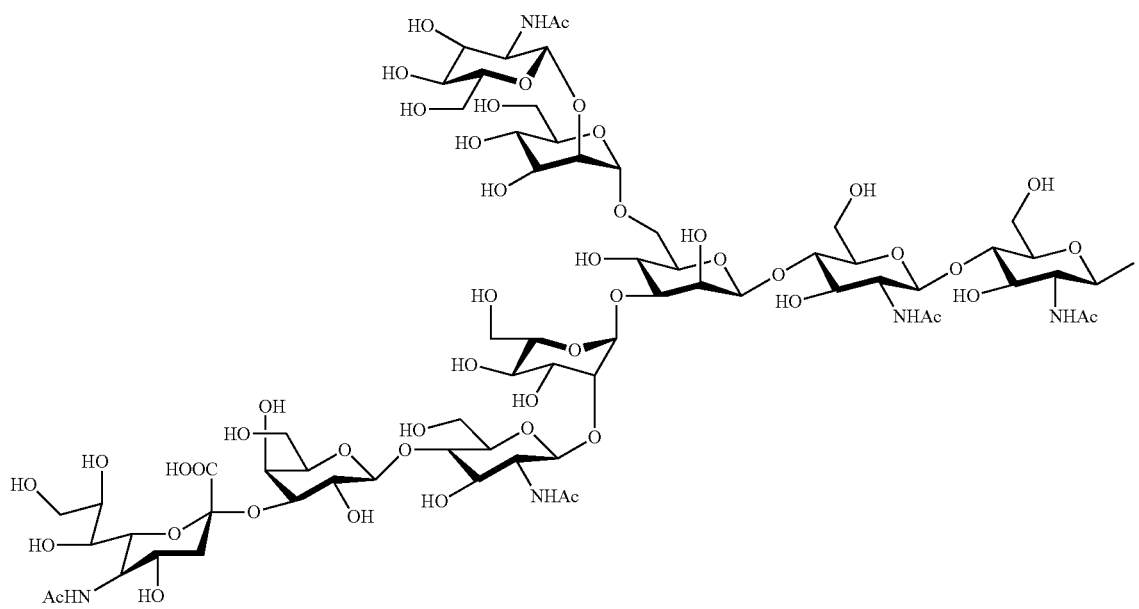
1GN2S(3)-9NC, 31

TABLE 3-continued
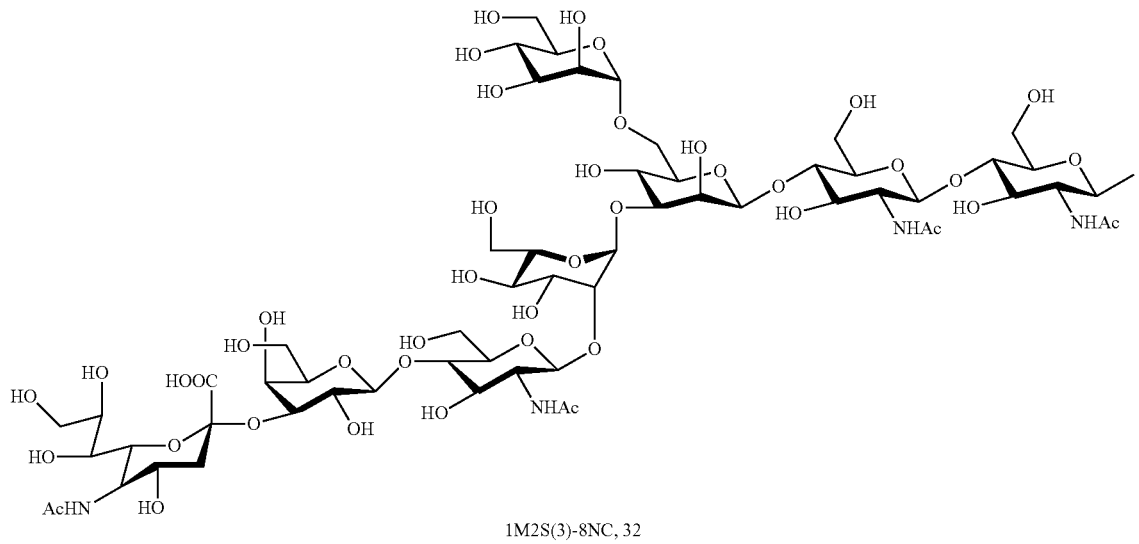
1M2S(3)-8NC, 32
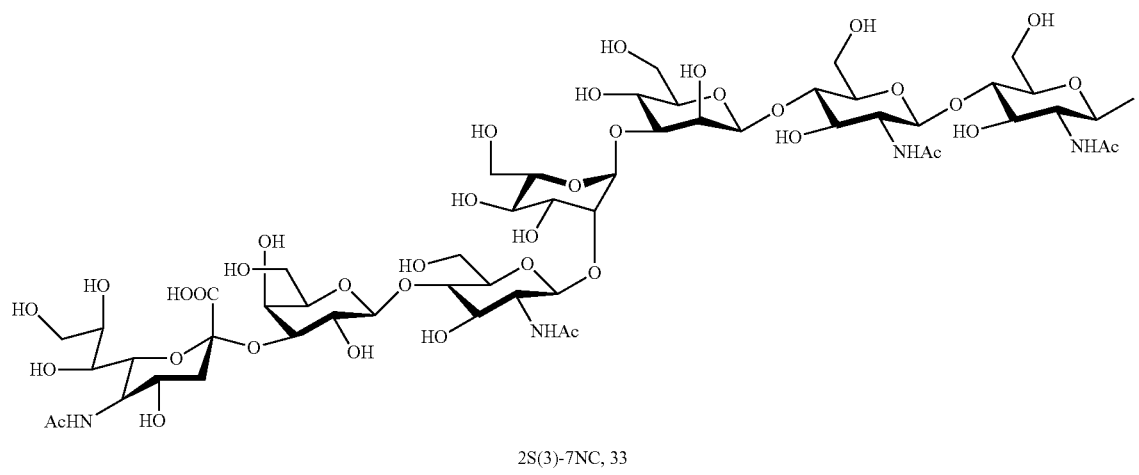
2S(3)-7NC, 33

TABLE 4

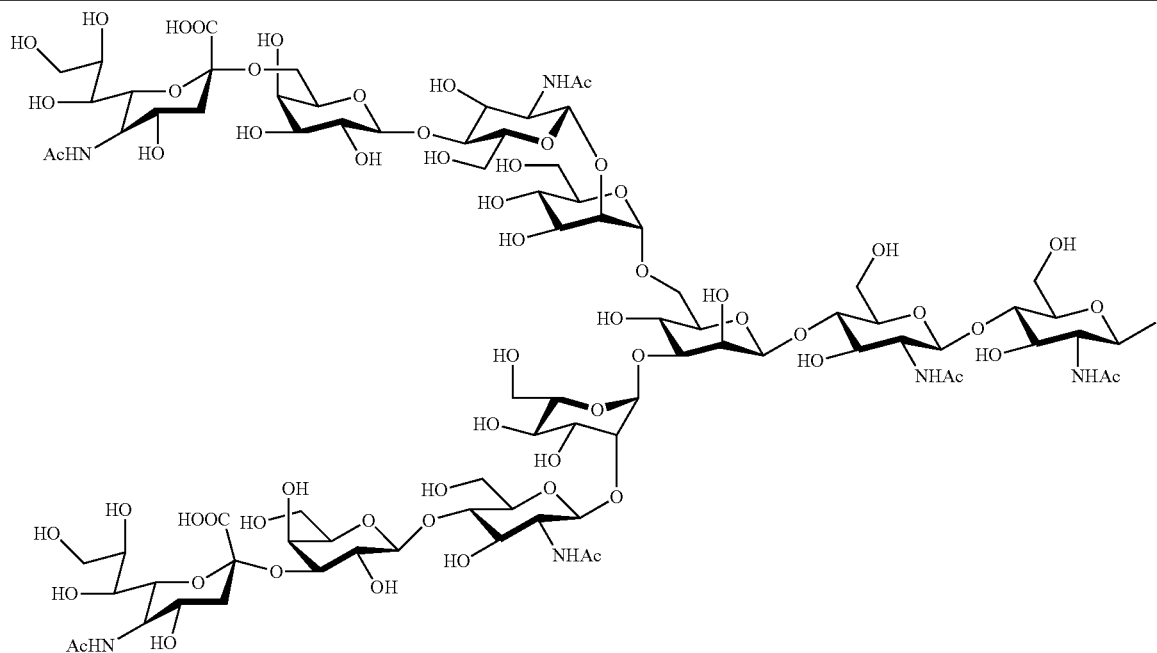

1S2S(3)-11NC, 34

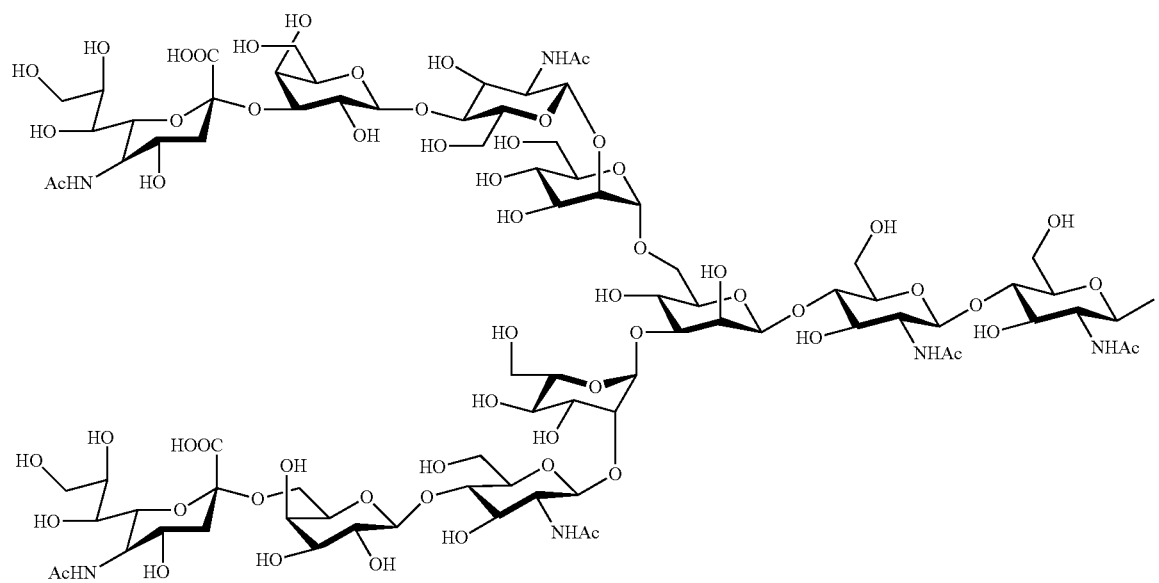

1S(3)2S-11NC, 35

According to a preferred embodiment, the structure of the sugar chain in the sugar chain, the glycosylated amino acid, or the glycosylated polypeptide according to the present invention is substantially homogeneous. The substantially homogeneous structure of the sugar chain in the sugar chain, the glycosylated amino acid, or the glycosylated polypeptide means that the type of each constituent sugar, binding order, and binding pattern between sugars are substantially identical when the sugar chains in the compound of the present invention or the salt thereof and the glycosylated linker of the present invention are compared, or means that the glycosylation site in the amino acid and/or the polypeptide, the type of each sugar constituting the sugar chain, binding order, and binding pattern between sugars are substantially identical when the glycosylated amino acids and/or the glycosylated polypeptides in the compound of the present invention or the salt thereof and the glycosylated linker of the present invention are compared. In this context, the phrase "substantially identical" means that at least 90% or more, preferably 95% or more, more preferably 99% or more sugar chains are structurally uniform. According to a further preferred embodiment, not only the structure of the sugar chain but the structure of the glycosylated amino acid and/or the glycosylated polypeptide according to the present invention are substantially homogeneous. The substantially homogeneous structure of the glycosylated amino acid and/ or the glycosylated polypeptide means that the type, structure, etc., of the sugar chain, the glycosylated amino acid, and/or the glycosylated polypeptide in the compound of the present invention or the salt thereof or the glycosylated linker of the present invention are substantially identical. In this context, the phrase "substantially identical" means that at least 90% or more, preferably 95% or more, more preferably 99% or more glycosylated amino acids and/or glycosylated polypeptides are structurally uniform. When the glycosylated linker according to the present invention has two or more sugar chains (i.e., when a plurality of sugar chains are present in one compound), and when the composition or the pharmaceutical composition of the present invention contains a plurality of compounds each comprising a glycosylated linker moiety and a physiologically active substance moiety, or salts thereof (i.e., when a plurality of compounds or salts thereof are present), all structures of the sugar chains in the sugar chains and the glycosylated amino acids and/or the glycosylated polypeptides preferably are substantially homogeneous. Furthermore, in these cases, all structures of the glycosylated amino acids and/or the glycosylated polypeptides more preferably are substantially homogeneous. The glycosylated amino acid and the glycosylated polypeptide having such a homogeneous sugar chain has constant quality and is particularly preferred in the field of the production of medicines, assays, etc. The ratio of homogeneous sugar chains can be measured by a method using, for example, HPLC, capillary electrophoresis, NMR, or mass spectrometry. The physiologically active substance to be bonded to the glycosylated linker or the linker (having a non-glycosylated structure) according to the present invention is preferably bonded with the same binding pattern.

The glycosylated amino acid or the glycosylated polypeptide having a substantially homogeneous amino acid sequence and/or sugar chain, used in the present invention, can be produced by a glycosylation step in combination with a peptide production method generally known to those skilled in the art, such as solid-phase synthesis, liquid-phase synthesize, cell-based synthesis, separation and extraction of a natural product. For such a method for producing the glycosylated amino acid or the glycosylated polypeptide, see, for example, International Publication Nos. WO 2010/021126, WO 2004/005330, and WO 2009/153960, Japanese Patent Laid-Open No. 2001-302695, International Publication No. WO 2005/095331, Japanese Patent Laid-Open No. 2009-242372, and Biochimica et Biophysica Acta 1526 (2001) pp. 242-248.

For the method for producing the sugar chain, see, for example, International Publication Nos. WO 03/008431, WO 2004/058984, WO 2004/008431, WO 2004/058824, WO 2004/070046, and WO 2007/011055.

According to one embodiment, the glycosylated polypeptide used in the present invention may include, but is not limited to, for example: glycosylated amino acids or glycosylated polypeptides in which a sugar chain unbound with an amino acid is bonded directly or via a linker to an amino acid or an amino acid on a polypeptide; glycosylated amino acids or glycosylated polypeptides derived from these glycosylated amino acids or glycosylated polypeptides as a result of elongating the already added sugar chain by the further addition of a sugar or a sugar chain to the added sugar chain; glycosylated polypeptides in which one or more (e.g., 2 to 30, preferably 2 to 10) amino acids are bonded to, for example, an amino group and/or a carboxy group, in a glycosylated amino acid and an amino acid or a polypeptide is further linked thereto; and glycosylated polypeptides in which a sugar chain bound with an amino acid is bonded to an amino acid on a polypeptide via a linker.

Alternatively, the glycosylated amino acid or the glycosylated polypeptide having the desired sugar chain structure may be efficiently obtained by the transfer of various sugars (e.g., fucose) to the glycosylated amino acid or the glycosylated polypeptide according to the present invention using glycosyltransferase. For example, the glycosylated amino acid or the glycosylated polypeptide having the desired sugar chain structure containing fucose can be obtained by the transfer of fucose using glycosyltransferase (e.g., fucosyltransferase). Also, the glycosylated amino acid or the glycosylated polypeptide having the desired sugar chain structure with a distinctive binding pattern can be obtained depending on the glycosyltransferase used.

Generally commercially available fucose or chemically synthesized fucose can be used as the fucose.

Generally commercially available, naturally occurring, or genetically recombined fucosyltransferase can be used. The fucosyltransferase used can be appropriately selected according to the type of the fucose to be transferred. Specific examples thereof can include fucosyltransferase V (human, recombinant, plasma-derived, serum-derived, milk-derived, or liver-derived), which is an enzyme transferring fucose to N-acetylglucosamine at the non-reducing end of sugar chain asparagine. Alternatively, fucose may be transferred by shifting the equilibrium by pH adjustment or the like using fucose hydrolase.

Hereinafter, each substituent in the glycosylated linker, the glycosylated linker moiety, the linker, or the linker moiety according to the present invention will be further described.

[$R^2$ and/or $R^3$]

$R^2$ and $R^3$ each independently represent a hydrogen atom, an alkyl group having 1 to 16 carbon atoms, or an aryl group having 5 to 16 carbon atoms (provided that both of $R^2$ and $R^3$ are not hydrogen atoms at the same time), or $R^2$ and $R^3$ form a 3- to 7-membered heterocyclic ring together with the nitrogen atom to which they are bonded. According to a preferred embodiment, $R^2$ and $R^3$ form a 3- to 7-membered heterocyclic ring together with the nitrogen atom to which they are bonded, though there is no limitation.

When $R^2$ and $R^3$ form a 3- to 7-membered heterocyclic ring together with the nitrogen atom to which they are bonded, the 3- to 7-membered heterocyclic ring may contain up to the maximum number of double bonds and may further have, in addition to the nitrogen atom adjacent to $R^2$ and $R^3$, a heteroatom selected from the group including a sulfur atom, an oxygen atom, and a nitrogen atom. According to one embodiment, the heteroatom is preferably selected from the group consisting of a sulfur atom, an oxygen atom, and a nitrogen atom. The 3- to 7-membered heterocyclic ring is not limited and is preferably selected from the group including aziridine, azetidine, pyrroline (2-pyrroline, 3-pyrroline, etc.), pyrrole, imidazole, imidazoline, pyrazole, pyrazoline, isoxazoline (3-isoxazoline, 4-isoxazoline, etc.), thiazoline (4-thiazoline, etc.), isothiazoline, thiadiazoline, pyrrolidine, imidazolidine, pyrazolidine, oxazolidine, isoxazolidine, thiazolidine, isothiazolidine, thiadiazolidine, piperazine, piperidine, morpholine, thiomorpholine, thiazine, tetrazole, triazole, triazolidine, tetrazolidine, azepane, diazepane, azepine, and homopiperazine.

According to one embodiment, the 3- to 7-membered heterocyclic ring may have one or more substituents at its replaceable positions. Examples of the substituents include, but are not limited to, alkyl having 1 to 16 carbon atoms, alkenyl having 2 to 16 carbon atoms, alkynyl having 2 to 16 carbon atoms, aryl having 5 to 16 carbon atoms, cycloalkyl having 3 to 8 carbon atoms, cycloalkenyl having 3 to 8 carbon atoms, hydroxy, mercapto, cyano, carbamoyl, carboxy, alkoxycarbonyl having 1 to 4 carbon atoms (e.g., methoxycarbonyl and ethoxycarbonyl), halogen, groups represented by —$(OA^1)n$-$OA^2$ [wherein $A^1$ represents alkylene having 1 to 4 carbon atoms, $A^2$ represents alkyl having 1 to 4 carbon atoms, and n represents an integer of 0 to 3] (e.g., methoxy, ethoxy, propoxy, isopropoxy, butoxy, isobutoxy, sec-butoxy, tert-butoxy, ethoxyethoxy, and methoxyethoxyethoxy), phenoxy, halogenophenoxy (e.g., o-, m-, or p-chlorophenoxy, and o-, m-, or p-bromophenoxy), alkylthio having 1 to 4 carbon atoms (e.g., methylthio, ethylthio, n-propylthio, isopropylthio, n-butylthio, and tert-butylthio), phenylthio, alkylsulfinyl having 1 to 4 carbon atoms (e.g., methylsulfinyl and ethylsulfinyl), alkylsulfonyl having 1 to 4 carbon atoms (e.g., methylsulfonyl and ethylsulfonyl), haloalkyl having 1 to 10 carbon atoms (e.g., difluoromethyl, trifluoromethyl, trifluoroethyl, and trichloroethyl), formyl, alkanoyl having 1 to 5 carbon atoms (e.g., acetyl), and benzoyl. Further examples thereof include, but are not limited to, unsubstituted or substituted amino, i.e., alkanoylamino having 1 to 6 carbon atoms (e.g., acetylamino and propionylamino), alkylamino having 1 to 16 carbon atoms (e.g., methylamino, ethylamino, n-propylamino, isopropylamino, n-butylamino, isobutylamino, sec-butylamino, tert-butylamino, pentylamino, hexylamino, heptylamino, octylamino, nonylamino, decylamino, undecylamino, dodecylamino, tridecylamino, tetradecylamino, pentadecylamino, and hexadecylamino, wherein these alkyl groups may each be substituted by a hydroxy group), and dialkylamino having 1 to 4 carbon atoms (e.g., dimethylamino, diethylamino, N-methyl-N-ethylamino, and N-methyl-N-propylamino).

When $R^2$ and/or $R^3$ is an alkyl group having 1 to 16 carbon atoms, the alkyl group having 1 to 16 carbon atoms may be a substituted or unsubstituted, linear or branched aliphatic hydrocarbon group. Examples of the alkyl group having 1 to 16 carbon atoms can include a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, and a n-hexadecyl group. Examples of the "alkyl group having 1 to 16 carbon atoms" as a branched aliphatic hydrocarbon group can include an isobutyl group, an isodecyl group, a 2-ethylhexyl group, a 2-octyl-dodecyl group, a neopentyl group, and a tert-butyl group. Examples of one or more substituents in the linear or branched aliphatic hydrocarbon group can include, each independently, an alkoxy group having 1 to 10 carbon atoms (e.g., methoxy, ethoxy, propoxy, and butoxy), an amino group, a hydroxy group, a thiol group, a carboxy group, or a halogen atom (e.g., fluorine, chlorine, bromine, and iodine).

According to one embodiment, when $R^2$ and/or $R^3$ is an alkyl group having 1 to 16 carbon atoms, the alkyl group having 1 to 16 carbon atoms is preferably a substituted or unsubstituted alkyl group having 1 to 10 carbon atoms. According to a more preferred embodiment, the alkyl group having 1 to 16 carbon atoms may be a substituted or unsubstituted alkyl group having 1 to 7 carbon atoms.

When $R^2$ and/or $R^3$ is an aryl group having 5 to 16 carbon atoms, the aryl group having 5 to 16 carbon atoms may be a substituted or unsubstituted aryl group. When one or more hydrogen atoms in the aryl group are replaced by substituents, examples of the substituents can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carboxy group, a halogen atom (e.g., fluorine, chlorine, bromine, and iodine), or an alkyl halide group having 1 to 4 carbon atoms (e.g., a methyl chloride group). Examples of the substituted or unsubstituted aryl group can include, but are not limited to, a phenyl group, a biphenyl group, a naphthyl group, an anthranyl group, a phenanthryl group, an anthryl group, an o-tolyl group, a m-tolyl group, a p-tolyl group, a xylyl group, an ethylphenyl group, and a benzyl group.

According to one embodiment, when $R^2$ and/or $R^3$ is an aryl group having 5 to 16 carbon atoms, the aryl group having 5 to 16 carbon atoms is preferably a substituted or unsubstituted aryl group having 5 to 10 carbon atoms. According to a more preferred embodiment, the aryl group having 5 to 16 carbon atoms may be a substituted or unsubstituted aryl group having 5 to 8 carbon atoms, for example, a phenyl group, an o-tolyl group, a m-tolyl group, a p-tolyl group, or a benzyl group.

[$R^4$]

Each $R^4$ independently represents a hydrogen atom, an alkyl group having 1 to 16 carbon atoms, or an aryl group having 5 to 16 carbon atoms.

When one or more of the $R^4$ moieties is an alkyl group having 1 to 16 carbon atoms, the alkyl group having 1 to 16 carbon atoms may be the same as the alkyl group having 1 to 16 carbon atoms mentioned above in relation to $R^2$ and/or $R^3$.

According to one embodiment, when one or more of the $R^4$ moieties is an alkyl group having 1 to 16 carbon atoms, the alkyl group having 1 to 16 carbon atoms is preferably a substituted or unsubstituted alkyl group having 1 to 10 carbon atoms. According to a more preferred embodiment, the alkyl group having 1 to 16 carbon atoms may be a substituted or unsubstituted alkyl group having 1 to 5 carbon atoms, for example, a methyl group, an ethyl group, or a propyl group.

When one or more of the $R^4$ moieties is an aryl group having 5 to 16 carbon atoms, the aryl group having 5 to 16 carbon atoms may be the same as the aryl group having 5 to 16 carbon atoms mentioned above in relation to $R^2$ and/or $R^3$.

According to one embodiment, when one or more of the $R^4$ moieties is an aryl group having 5 to 16 carbon atoms, the aryl group having 5 to 16 carbon atoms is preferably a substituted or unsubstituted aryl group having 5 to 10 carbon atoms. According to a more preferred embodiment, the aryl group having 5 to 16 carbon atoms may be a substituted or unsubstituted aryl group having 5 to 8 carbon atoms, for example, a phenyl group, an o-tolyl group, a m-tolyl group, a p-tolyl group, or a benzyl group.

All of the $R^4$ moieties may be the same, or 3 of the $R^4$ moieties may be the same. Alternatively, both of the two adjacent $R^4$ moieties bonded to different carbon atoms, both of the two $R^4$ moieties bonded to the same carbon atom, or both of the two opposite $R^4$ moieties bonded to different carbon atoms may be the same.

Preferably, at least one of the four $R^4$ moieties is a hydrogen atom. More preferably, at least any two of the four $R^4$ moieties are hydrogen atoms. Further preferably, at least any three of the four $R^4$ moieties are hydrogen atoms. Most preferably, all of the four $R^4$ moieties are hydrogen atoms.

[Y]
Y represents

[Formula 41]

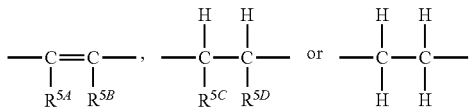

wherein
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group, and
$R^{5C}$ and $R^{5D}$ may form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded.

According to a preferred embodiment, Y in the glycosylated linker, the glycosylated linker moiety, or the linker moiety according to the present invention is

[Formula 42]

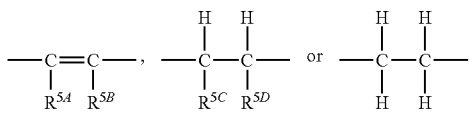

wherein
$R^{5A}$ and $R^{5B}$ form aryl having 5 to 16 carbon atoms together with the carbon atom to which $R^{5A}$ is bonded and the carbon atom to which $R^{5B}$ is bonded, or both of $R^{5A}$ and $R^{5B}$ are hydrogen atoms, and
$R^{5C}$ and $R^{5D}$ may form cyclohexyl or norbornyl together with the carbon atom to which $R^{5C}$ is bonded and the carbon atom to which $R^{5D}$ is bonded.

[$R^{5A}$ and/or $R^{5B}$]
$R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or $R^{5A}$ and $R^{5B}$ each independently represent a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group.

When $R^{5A}$ and $R^{5B}$ form aryl having 5 to 16 carbon atoms together with the carbon atom to which $R^{5A}$ is bonded and the carbon atom to which $R^{5B}$ is bonded, the aryl having 5 to 16 carbon atoms may be the same as the aryl group having 5 to 16 carbon atoms mentioned above in relation to $R^2$ and/or $R^3$.

According to one embodiment, when $R^{5A}$ and $R^{5B}$ form aryl having 5 to 16 carbon atoms together with the carbon atom to which $R^{5A}$ is bonded and the carbon atom to which $R^{5B}$ is bonded, the aryl having 5 to 16 carbon atoms is preferably substituted or unsubstituted aryl having 5 to 10 carbon atoms. According to a more preferred embodiment, the aryl having 5 to 16 carbon atoms may be substituted or unsubstituted aryl having 5 to 8 carbon atoms, for example, phenyl, o-tolyl, m-tolyl, p-tolyl, or benzyl.

When $R^{5A}$ and $R^{5B}$ form cycloalkenyl having 5 to 16 carbon atoms together with the carbon atom to which $R^{5A}$ is bonded and the carbon atom to which $R^{5B}$ is bonded, the cycloalkenyl having 5 to 16 carbon atoms may be substituted or unsubstituted cycloalkenyl. Examples of the unsubstituted cycloalkenyl include, but are not limited to, the cycloalkyl having 4 to 16 carbon atoms mentioned later in relation to $R^{5C}$ and $R^{5D}$ and further having one or more unsaturated bonds such as double bonds. Examples thereof can include cyclopentenyl, cyclohexenyl, cycloheptenyl, cyclooctenyl, cyclononenyl, cyclodecenyl, cycloundecenyl, cyclododecenyl, cyclotridecenyl, cyclotetradecenyl, cyclopentadecenyl, and cyclohexadecenyl. When one or more hydrogen atoms in the cycloalkenyl are replaced by substituents, examples of the substituents can include, each independently, an alkyl group having 1 to 4 carbon atoms, an alkoxy group having 1 to 4 carbon atoms (e.g., a methoxy group, an ethoxy group, a propoxy group, and a butoxy group), an amino group, a hydroxy group, a thiol group, a carboxy group, a halogen atom (e.g., fluorine, chlorine, bromine, and iodine), or an alkyl halide group having 1 to 4 carbon atoms (e.g., a methyl chloride group).

According to one embodiment, when $R^{5A}$ and $R^{5B}$ form cycloalkenyl having 5 to 16 carbon atoms together with the carbon atom to which $R^{5A}$ is bonded and the carbon atom to which $R^{5B}$ is bonded, the cycloalkenyl having 5 to 16 carbon atoms is preferably substituted or unsubstituted cycloalkenyl having 5 to 10 carbon atoms. According to a more preferred embodiment, the cycloalkenyl having 5 to 16 carbon atoms may be substituted or unsubstituted cycloalkenyl having 5 to 8 carbon atoms, for example, cyclohexenyl.

When $R^{5A}$ and $R^{5B}$ form bicyclyl having 7 to 13 carbon atoms together with the carbon atom to which $R^{5A}$ is bonded and the carbon atom to which $R^{5B}$ is bonded, the bicyclyl having 7 to 13 carbon atoms may be substituted or unsubstituted bicyclyl. As an example, the unsubstituted bicyclyl may have one or more unsaturated bonds such as double bonds and may have one or more heteroatoms in some cases, though there is no limitation. Also preferably, each ring of the bicyclyl may contain a 3- to 6-membered ring. When one or more hydrogen atoms in the bicyclyl are replaced by substituents, examples of the substituents can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carbonyl group, a carboxy group, a halogen atom (e.g., fluorine, chlorine, bromine, and iodine), or an alkyl halide group having 1 to 4 carbon atoms (e.g., a methyl chloride group). Examples of the bicyclyl having 7 to 13 carbon atoms can include, but are not limited to, azulenyl and naphthyl.

According to one embodiment, when $R^{5A}$ and $R^{5B}$ form bicyclyl having 7 to 13 carbon atoms together with the carbon atom to which $R^{5A}$ is bonded and the carbon atom to which $R^{5B}$ is bonded, the bicyclyl having 7 to 13 carbon atoms may be substituted or unsubstituted bicyclyl having 7 to 10 carbon atoms, for example, naphthyl.

When $R^{5A}$ and $R^{5B}$ form tricyclyl having 9 to 14 carbon atoms together with the carbon atom to which $R^{5A}$ is bonded and the carbon atom to which $R^{5B}$ is bonded, the tricyclyl having 9 to 14 carbon atoms may be substituted or unsubstituted tricyclyl. As an example, the unsubstituted tricyclyl may have one or more unsaturated bonds such as double bonds and may have one or more heteroatoms in some cases, though there is no limitation. Also preferably, each ring of the tricyclyl may contain 3 to 6 members. When one or more hydrogen atoms in the tricyclyl are replaced by substituents, examples of the substituents can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carbonyl group, a carboxy group, a halogen atom (e.g., fluorine, chlorine, bromine, and iodine), or an alkyl halide group having 1 to 4 carbon atoms (e.g., a methyl chloride group). Examples of the tricyclyl having 9 to 14 carbon atoms can include, but are not limited to, anthracenyl, phenanthryl, acenaphthenyl, acenaphthylenyl, fluorenyl, and their derivatives, for example, their hydrogenated products.

According to one embodiment, when $R^{5A}$ and $R^{5B}$ form tricyclyl having 9 to 14 carbon atoms together with the carbon atom to which $R^{5A}$ is bonded and the carbon atom to which $R^{5B}$ is bonded, the tricyclyl having 9 to 14 carbon atoms is preferably substituted or unsubstituted tricyclyl having 12 to 14 carbon atoms. According to a more preferred embodiment, the tricyclyl having 9 to 14 carbon atoms may be substituted or unsubstituted tricyclyl having 14 carbon atoms, for example, phenanthryl.

When $R^{5A}$ and $R^{5B}$ form quinone having 6 to 14 carbon atoms together with the carbon atom to which $R^{5A}$ is bonded and the carbon atom to which $R^{5B}$ is bonded, the quinone having 6 to 14 carbon atoms may be substituted or unsubstituted quinone. Examples of the unsubstituted quinone can include, but are not limited to, benzoquinone, anthraquinone, and naphthoquinone. The quinone also includes compounds in isomeric relationships, for example, o-benzoquinone and p-benzoquinone. When one or more hydrogen atoms in the quinone are replaced by substituents, examples of the substituent can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carbonyl group, a carboxy group, a halogen atom (e.g., fluorine, chlorine, bromine, and iodine), or an alkyl halide group having 1 to 4 carbon atoms (e.g., a methyl chloride group).

According to one embodiment, when $R^{5A}$ and $R^{5B}$ form quinone having 6 to 14 carbon atoms together with the carbon atom to which $R^{5A}$ is bonded and the carbon atom to which $R^{5B}$ is bonded, the quinone having 6 to 14 carbon atoms is preferably substituted or unsubstituted quinone having 6 to 10 carbon atoms. According to a more preferred embodiment, the quinone having 6 to 14 carbon atoms may be substituted or unsubstituted quinone having 6 carbon atoms, for example, benzoquinone.

When $R^{5A}$ and $R^{5B}$ form a 5- to 10-membered heterocyclic ring together with the carbon atom to which $R^{5A}$ is bonded and the carbon atom to which $R^{5B}$ is bonded, the 5- to 10-membered heterocyclic ring may be a substituted or unsubstituted heterocyclic ring. As an example, the unsubstituted heterocyclic ring may contain up to the maximum number of double bonds and may have one or more heteroatoms selected from the group including a nitrogen atom, a sulfur atom, an oxygen atom, and a nitrogen atom, though there is no limitation. In some cases, the heterocyclic ring may be a bicyclic or tricyclic ring having one or more heteroatoms (in such a case, the bicyclic or tricyclic heterocyclic ring having one or more heteroatoms may be, for example, the bicyclyl having 7 to 13 carbon atoms or the tricyclyl having 9 to 14 carbon atoms mentioned above). Examples of the heterocyclic ring can include, but are not limited to, a pyrazole ring, a pyrrole ring, a furan ring, a thiophene ring, an imidazole ring, a thiazole ring, an isothiazole ring, an oxazole ring, an isoxazole ring, a pyridine ring, a pyrazine ring, a pyrimidine ring, and a pyridazine ring. When one or more hydrogen atoms in the heterocyclic ring are replaced by substituents, examples of the substituents can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carbonyl group, a carboxy group, a halogen atom (e.g., fluorine, chlorine, bromine, and iodine), or an alkyl halide group having 1 to 4 carbon atoms (e.g., methyl chloride group).

According to one embodiment, when $R^{5A}$ and $R^{5B}$ form a 5- to 10-membered heterocyclic ring together with the carbon atom to which $R^{5A}$ is bonded and the carbon atom to which $R^{5B}$ is bonded, the heterocyclic ring is preferably a substituted or unsubstituted 5- to 8-membered heterocyclic ring. According to a more preferred embodiment, the heterocyclic ring may be a substituted or unsubstituted 5- to 7-membered heterocyclic ring, for example, a pyridine ring.

When $R^{5A}$ and $R^{5B}$ do not form a ring together with the carbon atom to which $R^{5A}$ is bonded and the carbon atom to which $R^{5B}$ is bonded, $R^{5A}$ and $R^{5B}$ may be each independently a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, an amino group, a substituted or unsubstituted phenyl group, or a benzyl group. Examples of the substituted phenyl group may include, but are not limited to, an o-tolyl group, a m-tolyl group, and a p-tolyl group. The acyl group having 1 to 3 carbon atoms is preferably a formyl group or an acetyl group. According to a preferred embodiment, when $R^{5A}$ and $R^{5B}$ do not form a ring together with the carbon atom to which $R^{5A}$ is bonded and the carbon atom to which $R^{5B}$ is bonded, $R^{5A}$ and $R^{5B}$ are each independently a hydrogen atom, a methyl group, an ethyl group, a propyl group, or a phenyl group. According to a more preferred embodiment, both of $R^{5A}$ and $R^{5B}$ are hydrogen atoms, methyl groups, or phenyl groups.

[$R^{5C}$ and/or $R^{5D}$]

When $R^{5C}$ and $R^{5D}$ form cycloalkyl having 4 to 16 carbon atoms together with the carbon atom to which $R^{5C}$ is bonded and the carbon atom to which $R^{5D}$ is bonded, the cycloalkyl having 4 to 16 carbon atoms may be substituted or unsubstituted cycloalkyl. Examples of the unsubstituted cycloalkyl can include, but are not limited to, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, and cyclohexadecyl. When one or more hydrogen atoms in the cycloalkyl are replaced by substituents, examples of the substituents can include, each independently, an alkyl group having 1 to 4 carbon atoms, an alkoxy group having 1 to 4 carbon atoms (e.g., methoxy, ethoxy, propoxy, and butoxy), an amino group, a hydroxy group, a thiol group, a carboxy group, a halogen atom (e.g., fluorine, chlorine, bromine, and iodine), or an alkyl halide group having 1 to 4 carbon atoms (e.g., a methyl chloride group).

According to one embodiment, when $R^{5C}$ and $R^{5D}$ form cycloalkyl having 4 to 16 carbon atoms together with the carbon atom to which $R^{5C}$ is bonded and the carbon atom to which $R^{5D}$ is bonded, the cycloalkyl having 4 to 16 carbon atoms is preferably substituted or unsubstituted cycloalkyl having 4 to 10 carbon atoms. According to a more preferred embodiment, the cycloalkyl having 4 to 16 carbon atoms may be substituted or unsubstituted cycloalkyl having 4 to 8 carbon atoms, for example, cyclopentyl, cyclohexyl, or cycloheptyl.

When $R^{5C}$ and $R^{5D}$ form cycloalkenyl having 5 to 16 carbon atoms together with the carbon atom to which $R^{5C}$ is bonded and the carbon atom to which $R^{5D}$ is bonded, the cycloalkenyl having 5 to 16 carbon atoms may be the same as the cycloalkenyl having 5 to 16 carbon atoms mentioned above in relation to $R^{5A}$ and/or $R^{5B}$.

According to one embodiment, when $R^{5C}$ and $R^{5D}$ form cycloalkenyl having 5 to 16 carbon atoms together with the carbon atom to which $R^{5C}$ is bonded and the carbon atom to which $R^{5D}$ is bonded, the cycloalkenyl having 5 to 16 carbon atoms is preferably substituted or unsubstituted cycloalkenyl having 5 to 10 carbon atoms. According to a more preferred embodiment, the cycloalkenyl having 5 to 16 carbon atoms may be substituted or unsubstituted cycloalkenyl having 5 to 8 carbon atoms, for example, cyclohexenyl.

When $R^{5C}$ and $R^{5D}$ form bicyclyl having 7 to 13 carbon atoms together with the carbon atom to which $R^{5C}$ is bonded and the carbon atom to which $R^{5D}$ is bonded, the bicyclyl having 7 to 13 carbon atoms may be the same as the bicyclyl having 7 to 13 carbon atoms mentioned above in relation to $R^{5A}$ and/or $R^{5B}$.

According to one embodiment, when $R^{5C}$ and $R^{5D}$ form bicyclyl having 7 to 13 carbon atoms together with the carbon atom to which $R^{5C}$ is bonded and the carbon atom to which $R^{5D}$ is bonded, the bicyclyl having 7 to 13 carbon atoms is preferably substituted or unsubstituted bicyclyl having 7 to 10 carbon atoms. According to a more preferred embodiment, the bicyclyl having 7 to 13 carbon atoms may be substituted or unsubstituted bicyclyl having 7 to 9 carbon atoms, for example, norbornyl or hexachloronorbornyl.

When $R^{5C}$ and $R^{5D}$ form tricyclyl having 9 to 14 carbon atoms together with the carbon atom to which $R^{5C}$ is bonded and the carbon atom to which $R^{5D}$ is bonded, the tricyclyl having 9 to 14 carbon atoms may be the same as the tricyclyl having 9 to 14 carbon atoms mentioned above in relation to $R^{5A}$ and/or $R^{5B}$.

According to one embodiment, when $R^{5C}$ and $R^{5D}$ form tricyclyl having 9 to 14 carbon atoms together with the carbon atom to which $R^{5C}$ is bonded and the carbon atom to which $R^{5D}$ is bonded, the tricyclyl having 9 to 14 carbon atoms is preferably substituted or unsubstituted tricyclyl having 12 to 14 carbon atoms. According to a more preferred embodiment, the tricyclyl having 9 to 14 carbon atoms may be substituted or unsubstituted tricyclyl having 14 carbon atoms, for example, tetradecahydrophenanthryl.

When $R^{5C}$ and $R^{5D}$ form a 5- to 10-membered heterocyclic ring together with the carbon atom to which $R^{5C}$ is bonded and the carbon atom to which $R^{5D}$ is bonded, the 5- to 10-membered heterocyclic ring may be the same as the 5- to 10-membered heterocyclic ring mentioned above in relation to $R^{5A}$ and/or $R^{5B}$.

According to one embodiment, when $R^{5C}$ and $R^{5D}$ form a 5- to 10-membered heterocyclic ring together with the carbon atom to which $R^{5C}$ is bonded and the carbon atom to which $R^{5D}$ is bonded, the heterocyclic ring is preferably a substituted or unsubstituted 5- to 8-membered heterocyclic ring. According to a more preferred embodiment, the heterocyclic ring may be a substituted or unsubstituted 5- to 7-membered heterocyclic ring, for example, epoxycyclohexyl.

[$R^8$, $R^{8A}$, and $R^{8'}$]

$R^8$ represents a hydrogen atom, an acyl group having 1 to 16 carbon atoms, a carbamate protective group (e.g., an Fmoc group, a Boc group, a Z group, a Troc group, or an Alloc group), an amino acid, a polypeptide, a sugar chain, a glycosylated amino acid, or a glycosylated polypeptide. According to one particular embodiment, $R^8$ may be a hydrogen atom, an acyl group having 1 to 16 carbon atoms, an Fmoc group, a Boc group, a Z group, a Troc group, or an Alloc group. $R^{8A}$ represents a protective group such as an acyl group having 1 to 16 carbon atoms, an Fmoc group, a Boc group, a Z group, a Troc group, or an Alloc group. $R^{8'}$ represents a protective group such as an acyl group having 1 to 16 carbon atoms, an Fmoc group, a Boc group, a Z group, a Troc group, or an Alloc group.

When $R^8$, $R^{8A}$, or $R^{8'}$ is an acyl group having 1 to 16 carbon atoms, the acyl group having 1 to 16 carbon atoms may be a substituted or unsubstituted acyl group. Examples of the substituted or unsubstituted acyl group can include, but are not limited to, a formyl group, an acetyl group, a methylcarbonyl group, an ethylcarbonyl group, a n-propylcarbonyl group, an iso-propylcarbonyl group, a n-butylcarbonyl group, an iso-butylcarbonyl group, a sec-butylcarbonyl group, a tert-butylcarbonyl group, a n-pentylcarbonyl group, an iso-pentylcarbonyl group, a neopentylcarbonyl group, a 2-methylbutylcarbonyl group, a benzoyl group, a 1-naphthoyl group, a 2-naphthoyl group, a methylbenzoyl group, an ethylbenzoyl group, a tolylcarbonyl group, a propylbenzoyl group, a 4-tert-butylbenzoyl group, a nitrobenzylcarbonyl group, a 3-butoxy-2-naphthoyl group, and a cinnamoyl group.

According to a preferred embodiment, when $R^8$, $R^{8A}$, or $R^{8'}$ is an acyl group having 1 to 16 carbon atoms, the acyl group having 1 to 16 carbon atoms may be a formyl group or an acetyl group.

According to a preferred embodiment, when $R^8$ is present, $R^8$ is a protective group such as an acyl group having 1 to 16 carbon atoms, an Fmoc group, a Boc group, a Z group, a Troc group, or an Alloc group in order to stabilize the compound of the present invention or the salt thereof under acidic conditions (e.g., pH 1 to pH 6).

[$R^9$]

Each $R^9$ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group.

When one or more of the $R^9$ moieties is halogen, the halogen is preferably fluorine, chlorine, bromine, or iodine.

When one or more of the $R^9$ moieties is an acyl group having 1 to 3 carbon atoms, the acyl group having 1 to 3 carbon atoms may be a substituted or unsubstituted acyl group. Examples of the unsubstituted acyl group can include, but are not limited to, a formyl group, an acetyl group, and a propionyl group. According to a preferred embodiment, when one or more of the $R^9$ moieties is an acyl group having 1 to 3 carbon atoms, the acyl group having 1 to 3 carbon atoms may be a formyl group or an acetyl group.

When one or more of the $R^9$ moieties is an alkyl group having 1 to 4 carbon atoms, the alkyl group having 1 to 4 carbon atoms may be a substituted or unsubstituted alkyl group. Examples of the unsubstituted alkyl group can include a methyl group, an ethyl group, a propyl group, and a butyl group. According to a preferred embodiment, when one or more of the $R^9$ moieties is an alkyl group having 1 to 4 carbon atoms, the alkyl group having 1 to 4 carbon atoms may be a methyl group or an ethyl group.

When one or more of the $R^9$ moieties is an alkoxy group having 1 to 4 carbon atoms, the alkoxy group having 1 to 4 carbon atoms may be a substituted or unsubstituted alkoxy group. Examples of the unsubstituted alkoxy group can include a methoxy group, an ethoxy group, a n-propoxy group, and a n-butoxy group. According to a preferred embodiment, when one or more of the $R^9$ moieties is an alkoxy group having 1 to 4 carbon atoms, the alkoxy group having 1 to 4 carbon atoms may be a methoxy group or an ethoxy group.

The present inventor has found that, surprisingly, the $R^9$ is preferably an electron-withdrawing group for immediately cleaving the glycosylated linker moiety from the compound comprising a glycosylated linker moiety and a physiologically active substance moiety or the salt thereof according to the present invention and thereby immediately releasing the physiologically active substance. Thus, according to a preferred embodiment, at least one of the four $R^9$ moieties may be independently substituted by halogen, a cyano group, a nitro group, a mesyl group (methanesulfonyl group), a tosyl group (p-toluenesulfonyl group), or an acyl group having 1 to 3 carbon atoms for immediately cleaving the glycosylated linker moiety from the compound of the present invention or the salt thereof and thereby immediately releasing the physiologically active substance.

Likewise, according to another preferred embodiment, when $R^{5A}$ and $R^{5B}$ in the glycosylated linker, the glycosylated linker moiety, or the linker moiety according to the present invention form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded or when $R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which $R^{5C}$ is bonded and the carbon atom to which $R^{5D}$ is bonded, at least one hydrogen atom present on these rings may be independently replaced by halogen, a cyano group, a nitro group, a mesyl group (methanesulfonyl group), a tosyl group (p-toluenesulfonyl group), or an acyl group having 1 to 3 carbon atoms.

A larger number of the electron-withdrawing groups is preferred for further accelerating the cleavage of the glycosylated linker moiety. The electron-withdrawing group is preferably halogen, more preferably chlorine.

Thus, according to a preferred embodiment, a physiologically active substance desired to exert its pharmacological activity or the like immediately after reaching a target environment (e.g., in blood) may be used for the compound of the present invention or the salt thereof or the glycosylated linker of the present invention.

When a hydrogen atom in the glycosylated linker moiety according to the present invention is replaced by a glycosylated amino acid or a glycosylated polypeptide, this replacement is preferably achieved by the amino acid moiety in the glycosylated amino acid or an amino acid moiety constituting the polypeptide in the glycosylated polypeptide. This replacement is not limited as long as the replacement is a binding manner generally known to those skilled in the art.

According to a preferred embodiment, the sugar chain, the glycosylated amino acid, and/or the glycosylated polypeptide according to the present invention is bonded through the replacement of at least one hydrogen atom bonded to the nitrogen atom, the carbon atom, and/or the sulfur atom, etc., present in the glycosylated linker moiety.

As an example, in the case of the glycosylated linker moiety according to the present invention represented by the formula (I), when $R^2$ or $R^3$ is a hydrogen atom (both of $R^2$ and $R^3$ are not hydrogen atoms at the same time), this hydrogen atom may be replaced by a glycosylated amino acid or a glycosylated polypeptide; or when $R^2$ and/or $R^3$ is an alkyl group having 1 to 16 carbon atoms or an aryl group having 5 to 16 carbon atoms or when $R^2$ and $R^3$ form a 3- to 7-membered heterocyclic ring together with the nitrogen atom to which they are bonded, at least one hydrogen atom bonded to the alkyl group, the aryl group, or the heterocyclic ring may be replaced by a sugar chain, a glycosylated amino acid, or a glycosylated polypeptide.

For example, when the $R^2$ is a methyl group, at least one hydrogen atom on the methyl group (—$CH_3$) may be replaced by a glycosylated amino acid or a glycosylated polypeptide. Alternatively, for example, when the $R^2$ and the $R^3$ form piperazine together with the nitrogen atom to which they are bonded, a hydrogen atom bonded to a nitrogen atom on the ring structure of the piperazine may be replaced by a glycosylated amino acid or a glycosylated polypeptide.

Preferably, at least one hydrogen atom bonded to the alkyl group, the aryl group, or a nitrogen atom present in the heterocyclic ring is replaced by a sugar chain, a glycosylated amino acid, or a glycosylated polypeptide. More preferably, at least one hydrogen atom bonded to the alkyl group, the aryl group, or a nitrogen atom present in the heterocyclic ring is replaced by a glycosylated amino acid or a glycosylated polypeptide. Further preferably, the replacement is a bond at the site of the amino acid or the polypeptide in the "glycosylated amino acid or glycosylated polypeptide".

As an example, in the case of the glycosylated linker moiety according to the present invention represented by the formula (II), the sugar chain, the glycosylated amino acid, or the glycosylated polypeptide represented by $R^6$ is bonded to a nitrogen atom on the ring structure of piperazine in the formula (II). According to one embodiment, $R^6$ is preferably a glycosylated amino acid or a glycosylated polypeptide. In this case, the bonding of $R^6$ to the nitrogen atom is preferably a bond at the site of the amino acid or the polypeptide in the "glycosylated amino acid or glycosylated polypeptide".

As an example, in the case of the glycosylated linker moiety according to the present invention represented by the formula (III) or the formula (IV), by the adoption of —S—$CH_2$—CONH-sugar chain or —CONH-sugar chain as $R^7$, the glycosylated linker moiety according to the present invention represented by the formula (III) or the formula (IV) has a sugar chain structure. When the glycosylated linker moiety further has a sugar chain, $R^8$ is the sugar chain, a glycosylated amino acid, or a glycosylated polypeptide and may be bonded to the nitrogen atom bonded to $R^8$ in the formula (III) or the formula (IV).

$R^8$ which is, for example, a hydrogen atom or a protective group such as an acyl group having 1 to 16 carbon atoms, an Fmoc group, a Boc group, a Z group, a Troc group, or an Alloc group may be further substituted by a sugar chain, a glycosylated amino acid, or a glycosylated polypeptide by use of the nucleophilicity of the amino group derived from the nitrogen atom bonded to $R^8$, though there is no limitation. When the substituted $R^8$ is a glycosylated amino acid or a glycosylated polypeptide, the substitution is preferably a bond at the site of the amino acid or the polypeptide in the "glycosylated amino acid or glycosylated polypeptide", though there is no limitation. As a matter of course, $R^8$ which is a hydrogen atom or a protective group such as an acyl group having 1 to 16 carbon atoms, an Fmoc group, a Boc group, a Z group, a Troc group, or an Alloc group is first substituted by an amino acid or a polypeptide, to which a sugar chain may be further added by a method well known to those skilled in the art.

According to one embodiment, the glycosylated amino acid according to the present invention may be bonded to the glycosylated linker moiety through the dehydration condensation reaction of the —OH moiety in a carboxy group present in the backbone of the amino acid with the aforementioned hydrogen atom derived from the glycosylated linker moiety. Alternatively, according to another embodiment, the glycosylated amino acid having serine, threonine, or tyrosine as its amino acid may be bonded thereto through the dehydration condensation reaction of a hydroxy group present in the side chain of this amino acid with the hydrogen atom. According to a further alternative embodiment, the glycosylated amino acid having aspartic acid or glutamic acid as its amino acid may be bonded thereto through the dehydration condensation reaction of the —OH moiety in a carboxy group present in the side chain of this amino acid with the hydrogen atom.

According to one embodiment, the glycosylated polypeptide according to the present invention may be bonded to the glycosylated linker moiety through the dehydration condensation reaction of the —OH moiety in the carboxy group of the C-terminal amino acid constituting the polypeptide with the aforementioned hydrogen atom derived from the glycosylated linker moiety. Alternatively, according to another embodiment, the glycosylated polypeptide containing a serine residue, a threonine residue, or a tyrosine residue as an amino acid residue constituting the polypeptide may be bonded thereto through the dehydration condensation reaction of a hydroxy group present in the side chain of this amino acid residue with the hydrogen atom. According to a further alternative embodiment, the glycosylated polypeptide containing an aspartic acid residue or a glutamic acid residue as an amino acid residue constituting the polypeptide may be bonded thereto through the dehydration condensation reaction of the —OH moiety in a carboxy group present in the side chain of this amino acid residue with the hydrogen atom.

In the present invention, $R^7$ may be bonded to any site (e.g., reducing end) of the sugar chain via the —S—CH$_2$—CONH— moiety or the —CONH— moiety. The sugar chain is bonded to the nitrogen atom in —S—CH$_2$—CONH— or —CONH—. When $R^7$ is —S—CH$_2$—CONH-sugar chain, —CH$_2$—CONH— represents a linker and, preferably, the sulfur atom may be derived from cysteine. When $R^7$ is —CONH-sugar chain, preferably, —CONH— may be derived from asparagine.

The glycosylated linker of the present invention is capable of binding to at least one amino group, hydroxy group, thiol group, or carboxy group carried by the physiologically active substance. The binding manner is not limited as long as the manner is generally known to those skilled in the art.

When the physiologically active substance has an amino group, the bonding is preferably an amide bond. When the physiologically active substance has a hydroxy group, the bonding is preferably an ester bond. When the physiologically active substance has a thiol group, the bonding is preferably a thioester bond. When the physiologically active substance has a carboxy group, the bonding is preferably an acid anhydride bond. When the physiologically active substance according to the present invention is a low-molecular physiologically active substance or a biopolymer, its binding manner is as described above.

When the physiologically active substance is a polynucleotide or partially contains a polynucleotide, the physiologically active substance may be bonded to the glycosylated linker of the present invention through an amide bond or an ester bond via an amino group or a hydroxy group carried by the polynucleotide, though there is no limitation.

When the physiologically active substance is a peptide nucleic acid or partially contains a peptide nucleic acid, the physiologically active substance may be bonded to the glycosylated linker of the present invention through an amide bond via an amino group or a carboxy group carried by the peptide nucleic acid, though there is no limitation.

When the physiologically active substance is a protein or a polypeptide or partially contains a peptide moiety, the physiologically active substance may be bonded to the glycosylated linker of the present invention through an amide bond, an ester bond, a thioester bond, or an acid anhydride bond via an amino group, a hydroxy group, a thiol group, or a carboxy group carried by the protein or the polypeptide or the peptide moiety, though there is no limitation.

According to a preferred embodiment, the physiologically active substance according to the present invention is a protein or a polypeptide which preferably
(I) has an amino acid-derived amino group at the N terminus,
(II) contains a serine residue, a threonine residue, or a tyrosine residue having a hydroxy group on the side chain,
(III) contains an aspartic acid residue or a glutamic acid residue having a carboxy group on the side chain,
(IV) contains a lysine residue, an asparagine residue, an arginine residue, a histidine residue, or a tryptophan residue having an amino group on the side chain,
(V) contains a cysteine residue having a thiol group on the side chain, or
(VI) has an amino acid-derived carboxy group at the C terminus.
The aspartic acid may be D-aspartic acid. Also, the glutamic acid may be D-glutamic acid. Likewise, other artificial amino acids may be adopted.

In such an embodiment, the bonding between the physiologically active substance moiety and the glycosylated linker moiety is preferably
(1) an amide bond at the N-terminal amino group in the physiologically active substance,
(2) an ester bond at the hydroxy group present in the side chain of the serine residue, the threonine residue, or the tyrosine residue in the physiologically active substance (but only in the case where the physiologically active substance has the serine residue, the threonine residue, or the tyrosine residue),
(3) an acid anhydride bond at the carboxy group (specifically, the —OH moiety in the —COOH group) present in the side chain of the aspartic acid residue or the glutamic acid residue in the physiologically active substance (but only in the case where the physiologically active substance has the aspartic acid residue or the glutamic acid residue), (4) an amide bond at the amino group present in the side chain of the lysine residue, the asparagine residue, the arginine residue, the histidine residue, or the tryptophan residue in the physiologically active substance (but only in the case where the physiologically active substance has the lysine residue, the asparagine residue, the arginine residue, the histidine residue, or the tryptophan residue), (5) a thioester bond at the thiol group present in the side chain of the cysteine residue in the physiologically active substance (but only in the case where the physiologically active substance has the cysteine residue), or (6) an acid anhydride bond at the C-terminal carboxy group in the physiologically active substance.

In the case of (1) or (4), the physiologically active substance moiety and the glycosylated linker moiety are linked via the —NH— moiety through the bond.

In the case of (2), (3), or (6), the physiologically active substance moiety and the glycosylated linker moiety are linked via the —O— moiety through the bond.

In the case of (5), the physiologically active substance moiety and the glycosylated linker moiety are linked via the —S— moiety through the bond.

When the physiologically active substance according to the present invention has a peptide moiety, the binding manner between the physiologically active substance moiety and the glycosylated linker moiety may be similar to the manner of the bond mentioned above for the protein or the polypeptide as the physiologically active substance.

It has been found that a larger number of sugar chains added to the linker moiety further improves the water solubility of the compound of the present invention or the salt thereof, but does not alter its half-life. This suggests that the presence of the sugar chain does not interfere with the cleavage of the linker moiety from the compound of the present invention or the salt thereof. Thus, in the present invention, when the glycosylated linker moiety and the physiologically active substance moiety are linked via an amide bond, the amide bond is cleaved, thereby cleaving the glycosylated linker. This mechanism, without intending to be bound to any theory, was considered to be based on the report of International Publication No. WO 2009/095479. This literature also specifically discloses (carrier) linker moieties having various structures (e.g., structures represented by

[Formula 43]

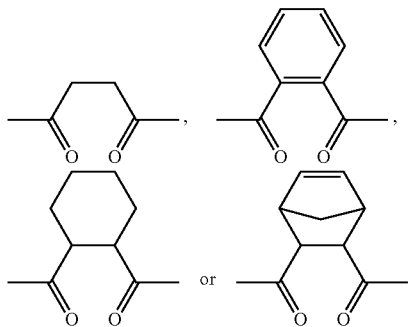

as structures corresponding to the substituent Y in the glycosylated linker moiety or the linker moiety according to the present invention, and also specifically discloses that the (carrier) linker moiety was cleaved to release and produce an unmodified drug. The literature has further reported that the release rate of the drug by the cleavage of the carrier-linker moiety from the "carrier-linker-drug conjugate" had in vivo/in vitro positive correlation. Thus, those skilled in the art understand that the release rate of the physiologically active substance resulting from the cleavage of the glycosylated linker moiety from the compound of the present invention or the salt thereof has in vivo/in vitro positive correlation.

Thus, according to a very preferred embodiment, a feature of the cleavage of the glycosylated linker moiety according to the present invention is to have in vivo/in vitro positive correlation. According to a very preferred embodiment, the compound of the present invention or the salt thereof and the glycosylated linker of the present invention have a sugar chain and can therefore be readily dissolved also in an in vivo environment (body fluid, for example, blood or lymph).

In the present invention, when the glycosylated linker moiety and the physiologically active substance moiety are linked via an ester bond, the mechanism underlying the cleavage of the bond was considered to be based on the report of Chem. Pharm. Bull. (2008), Vol. 56, pp. 1515-1520), without intending to be bound to any theory.

In the present specification, the "glycosylated linker" may be represented by the formula (B) "$R^1$-L" in which a glycosylated linker moiety ($R^1$) is bonded to a leaving group L. This glycosylated linker can be stably present in itself. The glycosylated linker of the present invention may be intended to bind to a physiologically active substance having at least one amino group, hydroxy group, thiol group, or carboxy group.

According to one embodiment, the glycosylated linker of the present invention is represented by the following formula (B):

$$R^1\text{-L} \qquad (B)$$

wherein $R^1$ represents a glycosylated linker moiety which is as defined above, and L represents a leaving group.

In this context, preferably, at least one hydrogen atom bonded to the alkyl group, the aryl group, or a nitrogen atom present in the heterocyclic ring is replaced by a glycosylated amino acid or a glycosylated polypeptide. More preferably, the replacement is a bond at the site of the amino acid or the polypeptide in the "glycosylated amino acid or glycosylated polypeptide".

The L represents a group capable of binding to the glycosylated linker moiety ($R^1$). The form and elimination reaction of the leaving group L are not particularly limited as long as they are generally known to those skilled in the art. For example, a leaving group as disclosed in International Publication No. WO 2009/095479 may be used. According to one embodiment, the L is not limited and may be chlorine, bromine, fluorine, nitrophenoxy, imidazolyl, N-hydroxysuccinimidyl, N-hydroxybenzotriazolyl, N-hydroxyazobenzotriazolyl, pentafluorophenoxy, 2-thioxo-thiazolidinyl, or N-hydroxysulfosuccinimidyl.

The glycosylated linker of the present invention can be stably preserved under low-temperature (e.g., −80° C. to 4° C., preferably −80° C. to −30° C.) conditions. The leaving group L can be removed from the glycosylated linker through elimination reaction, and the resulting glycosylated linker moiety can be bonded in the aforementioned manner to the physiologically active substance.

The glycosylated linker moiety self-cleaved from the "compound comprising a glycosylated linker moiety and a physiologically active substance moiety, or the salt thereof" may be recovered by a method well known to those skilled in the art and then reused as the glycosylated linker of the present invention.

When the synthesized or recovered glycosylated linker of the present invention is a glycosylated linker represented by the formula (I"), free carboxylic acid in the glycosylated linker may be subjected to dehydration condensation with at least one amino group, hydroxy group, thiol group, or carboxy group carried by the physiologically active substance so that the glycosylated linker of the present invention is bonded to the physiologically active substance to produce the compound of the present invention or the salt thereof.

Alternatively, only the linker moiety according to the present invention may be synthesized, to which a sugar chain, a glycosylated amino acid, and/or a glycosylated polypeptide can then be bonded to produce the glycosylated linker moiety. To the produced glycosylated linker, a physiologically active substance such as a protein or a polypeptide separately obtained by extraction or expression from an organism, or chemical synthesis, etc., may be bonded. For example, Bioconjugate Chem. (2007), Vol. 18, pp. 1869-1878 has reported that an unmodified protein was produced by the cleavage of a PEG-modified moiety and a linker moiety under reductive conditions (in the presence of thiol) from a PEG-modified linker-protein conjugate in which a protein is bonded through an amide bond to a PEG-modified linker activated with a p-nitrophenyl group. Also, National Publication of International Patent Application No. 2007-528354 has reported that: PEG-S-MAL-FMS-NH-peptide/protein conjugates were synthesized through two different routes by modifying a peptide/protein with a PEG-modified linker activated with a N-hydroxysuccinimide group so that the peptide/protein was bonded to the PEG-modified linker through an amide bond; and as a result, the PEG-modified linker moiety was cleaved under physiological conditions to yield an unmodified peptide/protein. These technical literatures explain that a carrier-linker moiety bonded to a drug through an amide bond releases the drug itself by the degradation of the linker. Those skilled in the art can understand that the glycosylated linker of the present invention can be synthesized and used on the basis of, for example, the instruction of the present specification and these literatures.

Once the glycosylated linker moiety is cleaved from the compound of the present invention or the salt thereof, the site in the cleaved glycosylated linker to which the physiologically active substance moiety having at least one amino group, hydroxy group, thiol group, or carboxy group has been bonded has a —OH group. In other words, the glycosylated linker immediately after cleavage from the compound comprising a glycosylated linker moiety and a physiologically active substance moiety or the salt thereof according to the present invention may be a glycosylated linker represented by the formula (I") in the present specification.

In the present invention, the "linker" (having a non-glycosylated structure) in the glycosylated linker can be produced in a non-glycosylated state. Its production method, production conditions, etc., are not limited. For example, a free carboxy group in dicarboxylic acid derived from dicarboxylic anhydride (e.g., phthalic anhydride) may be condensed with a free amino group (—NH$_2$) in diamine (e.g., N-(2-aminoethyl)piperazine) to synthesize the linker. The dicarboxylic anhydride and the diamine are not limited and may be the same as dicarboxylic anhydride and diamine that may be used in units for forming the glycosylated linker mentioned later. In the case of producing the linker (having a non-glycosylated structure) using dicarboxylic anhydride and diamine, the linker may be synthesized according to a method and procedures for producing the glycosylated linker using units for forming the glycosylated linker mentioned later. In view of the final structure of the glycosylated linker of interest, those skilled in the art can synthesize diverse linkers by appropriately selecting reaction conditions, reaction compounds, etc.

In the present invention, a method for bonding the linker moiety to the physiologically active substance, reaction conditions, etc. are not limited. Those skilled in the art should understand that the bonding can be appropriately performed with reference to a production method, production conditions, etc., described in, for example, International Publication No. WO 2009/095479.

According to one embodiment, the compound comprising a glycosylated linker moiety and a physiologically active substance moiety or the salt thereof according to the present invention may be synthesized by use of a liquid-phase synthesis method or a solid-phase synthesis method. In the case of using, for example, the solid-phase synthesis method, the compound comprising a glycosylated linker moiety and a physiologically active substance moiety or the salt thereof according to the present invention may be synthesized by a process comprising the steps of;

(A) immobilizing the physiologically active substance onto an appropriate resin;

(B) bonding the linker through an amide bond, an ester bond, a thioester bond, or an acid anhydride bond to at least one amino group, hydroxy group, thiol group, or carboxy group carried by the physiologically active substance; and (C) subsequently bonding a sugar chain, a glycosylated amino acid, and/or a glycosylated polypeptide to the linker.

According to one embodiment, the physiologically active substance having the desired linker moiety may be obtained by using, instead of the step (B), (B') condensing a first linker moiety (dicarboxylic anhydride (e.g., phthalic anhydride)) through an amide bond, an ester bond, a thioester bond, or an acid anhydride bond with at least one free amino group, hydroxy group, thiol group, or carboxy group carried by the physiologically active substance, and further condensing a free amino group in a second linker moiety (diamine (e.g., N-(2-aminoethyl)piperazine)) with a free carboxy group in the first linker moiety. Those skilled in the art can synthesize the physiologically active substance having the desired linker moiety by appropriately selecting reaction conditions, compounds constituting a portion of the linker to be reacted, etc., and continuously condensing the compounds with the physiologically active substance.

According to another embodiment, when the physiologically active substance is a protein or a polypeptide or partially contains a peptide moiety, the step (A) may involve synthesizing a protein or a polypeptide on an appropriate resin by a solid-phase synthesis method, prior to the step (B) or the step (B'). The method for synthesizing a protein or a polypeptide by the solid-phase synthesis method is not limited as long as the method is well known to those skilled in the art.

The method for producing the compound of the present invention or the salt thereof by combination with the method for synthesizing a protein or a polypeptide by the solid-phase synthesis method may be carried out, for example, as follows:

(1) A hydroxy group in a hydroxy group-containing resin is first subjected to esterification reaction with a carboxy group in an amino acid with an amino group protected with a lipid-soluble protective group. In this case, since the amino group of the amino acid is protected with a lipid-soluble protective group, the amino acid is prevented from being self-condensed. Hence, the esterification reaction occurs between the hydroxy group of the resin and the carboxy group of the amino acid.

(2) Next, the lipid-soluble protective group in the ester obtained in the step (1) is eliminated to form a free amino group.

(3) The free amino group is subjected to amidation reaction with a carboxy group of another amino acid with an amino group protected with a lipid-soluble protective group.

(4) After the step (3), the lipid-soluble protective group is eliminated to form a free amino group.

(5) The steps (3) and (4) can be repeated as required to obtain a polypeptide composed of a desired number of amino acids linked.

The polypeptide obtained in the step (5) has one end bonded to the resin and a free amino group at the other end. Thus, (6) a linker having the structure of interest is bonded through an amide bond, an ester bond, a thioester bond, or an acid anhydride bond to the free amino group of the polypeptide bonded to the resin.

(7) At least one hydrogen atom in the predetermined substituent of the linker moiety is replaced by a sugar chain, a glycosylated amino acid, and/or a glycosylated polypeptide.

(8) The ester bond formed in the step (1) is cleaved with an acid.

By the production method comprising these steps (1) to (8), the desired linker moiety-polypeptide compound having a sugar chain, glycosylated amino acid, and/or glycosylated polypeptide moiety can be produced.

Alternatively, after the step (6), (7') at least one hydrogen atom in the predetermined substituent of the linker moiety is replaced by an amino acid and/or a polypeptide.

(8') The ester bond formed in the step (1) is cleaved with an acid to obtain the desired linker moiety-polypeptide compound having an amino acid and/or polypeptide moiety.

(9') A sugar chain is added to the amino acid and/or polypeptide moiety of the compound.

By the production method comprising these steps (1) to (6) and (7') to (9'), the desired linker moiety-polypeptide compound having a sugar chain, glycosylated amino acid, and/or glycosylated polypeptide moiety can be produced.

In these cases, the solid-phase resin can be any resin usually used in solid-phase synthesis. For example, Amino-PEGA resin (manufactured by Merck KGaA), Wang resin (manufactured by Merck KGaA), HMPA-PEGA resin (manufactured by Merck KGaA), or 2-chlorotrityl chloride resin (manufactured by Merck KGaA) can be used.

Alternatively, a linker may be located between the Amino-PEGA resin and the amino acid. Examples of such a linker can include 4-hydroxymethylphenoxyacetic acid (HMPA) and 4-(4-hydroxymethyl-3-methoxyphenoxy)-butylacetic acid (HMPB).

Examples of the lipid-soluble protective group can include, but are not particularly limited to, carbonyl-containing groups such as a 9-fluorenylmethoxycarbonyl (Fmoc) group, a t-butyloxycarbonyl (Boc) group, a benzyloxycarbonyl (Z) group, a 2,2,2-trichloroethoxycarbonyl (Troc) group, and an allyloxycarbonyl (Alloc) group, acyl groups such as an acetyl (Ac) group, and other protective groups such as an allyl group and a benzyl group.

In the case of introducing the lipid-soluble protective group, for example, an Fmoc group, 9-fluorenylmethyl-N-succinimidyl carbonate and sodium bicarbonate can be added and reacted to introduce the Fmoc group. The reaction can be carried out at 0 to 50° C., preferably room temperature, for approximately 1 to 5 hours.

The amino acids mentioned above can be protected by the method described above and used as amino acids protected with the lipid-soluble protective group. Alternatively, commercially available products may be used. Examples thereof can include Fmoc-Ala-OH, Fmoc-Cys(Acm)-OH, Fmoc-Cys(tButhio)-OH, Fmoc-Cys(Trt)-OH, Fmoc-Asp(OtBu)-OH, Fmoc-Glu(OtBu)-OH, Fmoc-Phe-OH, Fmoc-Gly-OH, Fmoc-His(Trt)-OH, Fmoc-Ile-OH, Fmoc-Lys(Boc)-OH, Fmoc-Leu-OH, Fmoc-Met-OH, Fmoc-Asn(Trt)-OH, Fmoc-Pro-OH, Fmoc-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, and Fmoc-Tyr(tBu)-OH.

A dehydration condensation agent known in the art, for example, 1-mesitylenesulfonyl-3-nitro-1,2,4-triazole (MSNT), dicyclohexylcarbodiimide (DCC), or 1,3-diisopropylcarbodiimide (DIC), can be used as an esterification catalyst. The ratio between the amino acid and the dehydration condensation agent used may be usually 1 to 10 parts by weight, preferably 2 to 5 parts by weight, of the dehydration condensation agent with respect to 1 part by weight of the amino acid.

The esterification reaction is preferably carried out, for example, by placing a resin in a solid-phase column, washing this resin with a solvent, and then adding an amino acid solution thereto. Examples of the solvent for washing can include dimethylformamide (DMF), 2-propanol, and dichloromethane. Examples of the solvent for dissolving the amino acid can include dimethyl sulfoxide (DMSO), DMF, and dichloromethane. The esterification reaction can be carried out at 0 to 50° C., preferably at room temperature, for approximately 10 minutes to 30 hours, preferably approximately 15 minutes to 24 hours. After the esterification reaction, unreacted functional groups on the solid phase are preferably capped by acetylation using acetic anhydride or the like.

The lipid-soluble protective group can be eliminated by treatment with, for example, a base. Examples of the base can include piperidine and morpholine. This treatment is preferably carried out in the presence of a solvent. Examples of the solvent can include DMSO, DMF, and methanol.

The amidation reaction of a free amino group with a carboxy group in any amino acid or polypeptide with amino group nitrogen protected with a lipid-soluble protective group is preferably carried out in the presence of an activator and a solvent.

Examples of the activator can include dicyclohexylcarbodiimide (DCC), 1-ethyl-3-(3-dimethylaminopropyl)carbodiimide hydrochloride (WSC/HCl), diphenylphosphorylazide (DPPA), carbonyldiimidazole (CDI), diethyl cyanophosphonate (DEPC), 1,3-diisopropylcarbodiimide (DIC), benzotriazol-1-yloxy-trispyrrolidinophosphonium hexafluorophosphate (PyBOP), 3-diethoxyphosphoryloxy-1,2,3-benzotriazin-4(3H)-one (DEPBT), 1-hydroxybenzotriazole (HOBt), hydroxysuccinimide (HOSu), dimethylaminopyridine (DMAP), 1-hydroxy-7-azabenzotriazole (HOAt), 3-hydroxy-4-oxo-3,4-dihydro-5-azabenzo-1,2,3-triazine (HODhbt), hydroxyphthalimide (HOPht), pentafluorophenol (Pfp-OH), 2-(1H-benzotriazol-1-yl)-1,1,3,3-tetramethyluronium hexafluorophosphate (HBTU), O-(7- azabenzotriazol-1-yl)-1,1,3,3-tetramethyluronium hexafluorophosphonate (HATU), O-(6-chloro-1H-benzotriazol-1-yl)-N,N,N',N'-tetramethyluronium hexafluorophosphate (HCTU), and 0-benzotriazol-1-yl-1,1,3,3-tetramethyluronium tetrafluoroborate (TBTU).

The amount of the activator used is preferably set to 1 to 20 equivalents, preferably 1 to 10 equivalents, more preferably 1 to 5 equivalents, with respect to any amino acid or polypeptide with amino group nitrogen protected with a lipid-soluble protective group.

The reaction proceeds even in the presence of only the activator. Amine is preferably used as an auxiliary in combination therewith. For example, diisopropylethylamine (DIPEA), N-ethylmorpholine (NEM), N-methylmorpholine (NMM), N-methylimidazole (NMI), or 2,4,6-trimethylpyridine can be used as the amine. The amount of the auxiliary used is preferably set to 1 to 20 equivalents, preferably 1 to 10 equivalents, more preferably 1 to 5 equivalents, with respect to any amino acid or polypeptide with amino group nitrogen protected with a lipid-soluble protective group.

Examples of the solvent can include DMSO, DMF, and dichloromethane. The reaction can be carried out at 0 to 50° C., preferably at room temperature, for approximately 10 minutes to 30 hours, preferably approximately 15 minutes to 24 hours. Meanwhile, unreacted amino groups on the solid phase are preferably capped by acetylation using acetic anhydride or the like. The lipid-soluble protective group can be eliminated in the same way as above.

The peptide chain is preferably cleaved from the resin by treatment with an acid. Examples of the acid can include trifluoroacetic acid (TFA) and hydrogen fluoride (HF). Since the lipid-soluble protective group used in the amino acid and the linker on the resin may form highly reactive cation species, a nucleophilic reagent is preferably added thereto for scavenging the cation species. Examples of the nucleophilic reagent can include triisopropylsilane (TIS), phenol, thioanisole, and ethanedithiol (EDT).

Conditions for the condensation reaction of the physiologically active substance (e.g., polypeptide) obtained by chemical synthesis, biosynthesis, or purchase, etc., with the linker are not particularly limited and can be appropriately selected on the basis of a method well known to those skilled in the art. For example, units for forming the glycosylated linker (e.g., dicarboxylic acid, diamine, and a sugar chain, a glycosylated amino acid, and/or a glycosylated polypeptide) may be allowed to act sequentially on the physiologically active substance. In this case, dicarboxylic acid is first introduced thereto, subsequently diamine is introduced via an amide bond to one carboxylic acid in the dicarboxylic acid, and finally a sugar chain, a glycosylated amino acid, and/or a glycosylated polypeptide may be introduced via an amide bond to the other amino group of the diamine. In the case where the other amino group in the diamine has been used, for example, in the formation of a substituted or unsubstituted 3- to 7-membered heterocyclic ring, the amino group to be subjected to the amide bond with the glycosylated amino acid and/or the glycosylated polypeptide may be an amino group derived from the 3- to 7-membered heterocyclic ring structure. The introduction of the dicarboxylic acid can be carried out, for example, through the reaction of acid anhydride of the dicarboxylic acid with, for example, a free amino group in the diamine in the presence of a base such as pyridine. The introduction of the diamine can be carried out, for example, by the condensation of the diamine with a free carboxy group in the dicarboxylic acid in the presence of the activator and the auxiliary amine. Examples of the solvent for the reaction can include DMSO, DMF, and dichloromethane. This reaction can be carried out at 0 to 50° C., preferably at room temperature, for approximately 10 minutes to 30 hours, preferably approximately 15 minutes to 24 hours, though there is no limitation.

Examples of the acid anhydride of the dicarboxylic acid include, but are not limited to, compounds given below. Examples of the acid anhydride of the dicarboxylic acid having an aryl ring include

[Formula 44]

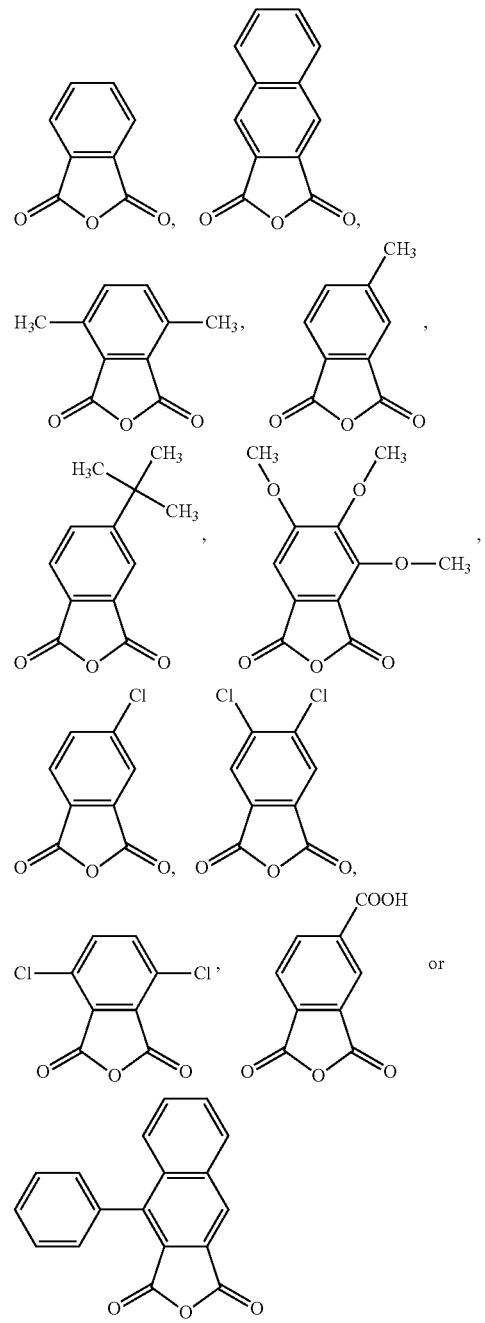

Examples of the acid anhydride of the dicarboxylic acid having a cycloalkyl ring include

[Formula 45]
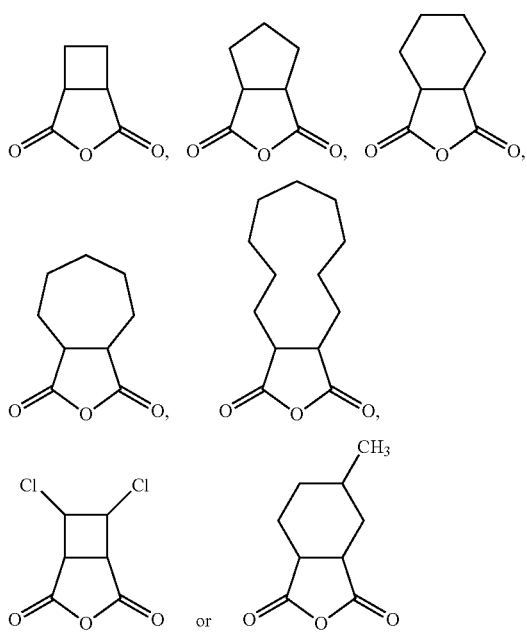
Examples of the acid anhydride of the dicarboxylic acid having a cycloalkenyl ring include
[Formula 46]
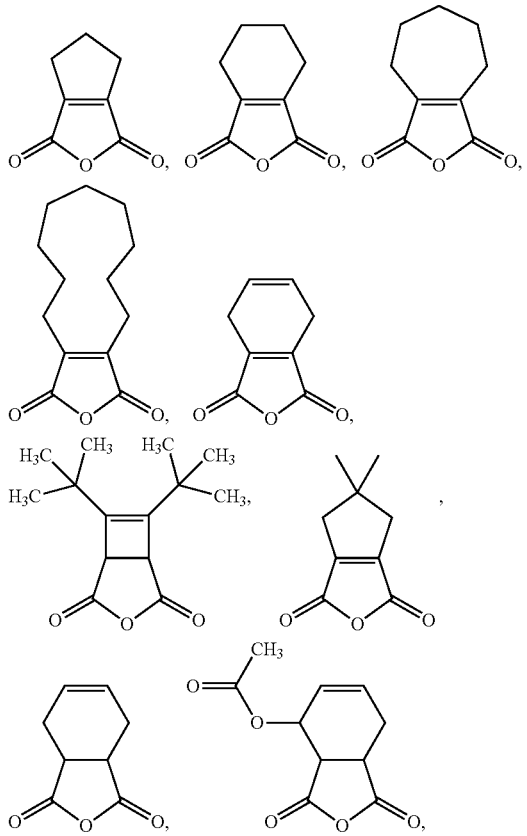
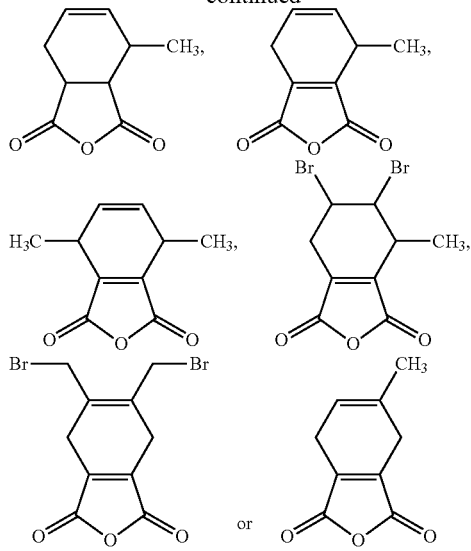
Examples of the acid anhydride of the dicarboxylic acid having a heterocyclic ring include
[Formula 47]
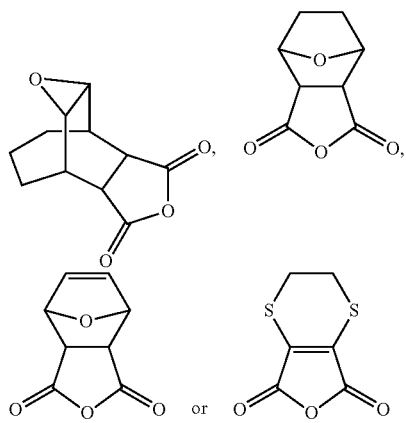
Examples of the acid anhydride of the dicarboxylic acid having bicyclyl include
[Formula 48]
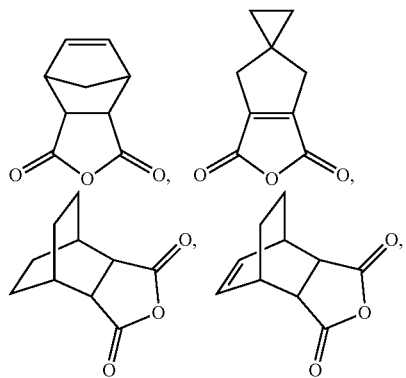

-continued

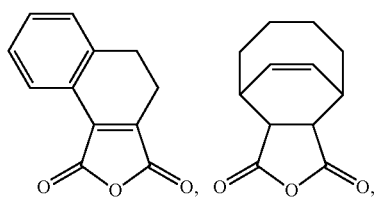

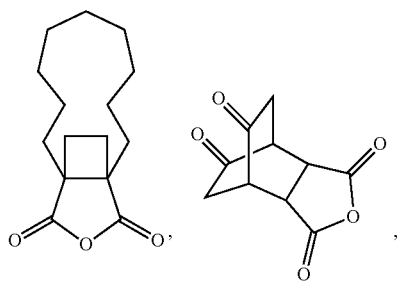

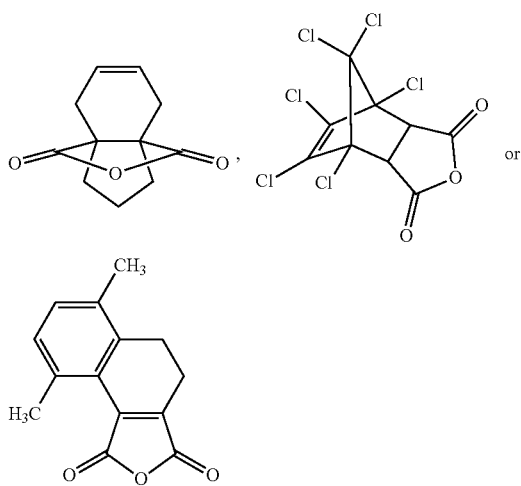

Examples of the acid anhydride of the dicarboxylic acid having tricyclyl include

[Formula 49]

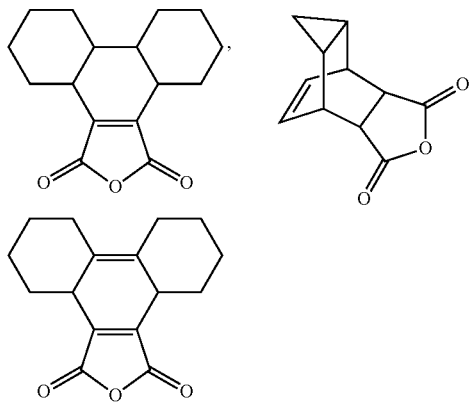

Examples of the acid anhydride of the dicarboxylic acid having a quinone structure include

[Formula 50]

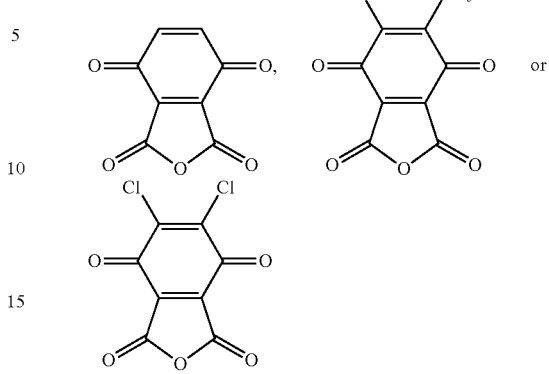

Other examples thereof may include the following acid anhydrides of the dicarboxylic acid:

[Formula 51]

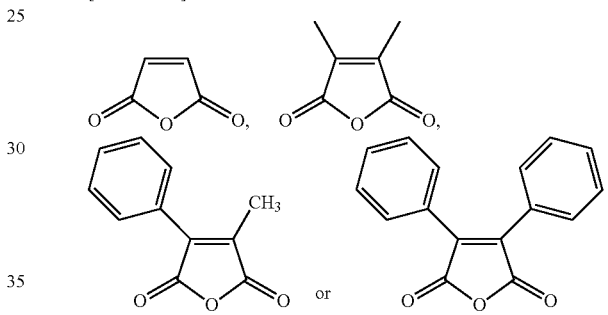

As for the substituent Y in the glycosylated linker, the glycosylated linker moiety, or the linker moiety according to the present invention, when $R^{5A}$ and $R^{5B}$ form aryl having 5 to 16 carbon atoms, cycloalkenyl having 5 to 16 carbon atoms, bicyclyl having 7 to 13 carbon atoms, tricyclyl having 9 to 14 carbon atoms, quinone having 6 to 14 carbon atoms, or a 5- to 10-membered heterocyclic ring together with the carbon atom to which $R^{5A}$ is bonded and the carbon atom to which $R^{5B}$ is bonded, or when $R^{5C}$ and $R^{5D}$ form cycloalkyl having 4 to 16 carbon atoms, cycloalkenyl having 5 to 16 carbon atoms, bicyclyl having 7 to 13 carbon atoms, tricyclyl having 9 to 14 carbon atoms, or a 5- to 10-membered heterocyclic ring together with the carbon atom to which RCC is bonded and the carbon atom to which $R^{5D}$ is bonded, the structure of Y corresponds to, for example, the structural moiety, except for C(=O)—O—C(=O), of the diverse acid anhydrides of the dicarboxylic acid specifically shown above. In the case of producing, for example, the compound of the present invention or the salt thereof, the glycosylated linker of the present invention, or the linker (having a non-glycosylated structure) using phthalic anhydride as the dicarboxylic anhydride, the phenyl ring moiety surrounded by the dotted line in the following formula in the phthalic anhydride (i.e., the structural moiety of the phthalic anhydride except for C(=O)—O—C(=O)) corresponds to the structure of the substituent Y:

[Formula 52]

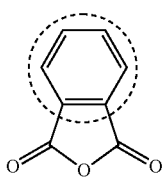

Those skilled in the art should naturally understand that the structural moiety, except for C(=O)—O—C(=O), of the diverse acid anhydrides of the dicarboxylic acid can be introduced as a portion of a moiety constituting the glycosylated linker or the linker.

The diamine is not limited and may be substituted or unsubstituted ethylenediamine. When one or more hydrogen atoms present at a site other than amino groups in ethylenediamine are replaced by substituents, the substituents may be an alkyl group having 1 to 16 carbon atoms or an aryl group having 5 to 16 carbon atoms. In the substituted or unsubstituted ethylenediamine, one of the amino groups may be further used in the formation of a substituted or unsubstituted 3- to 7-membered heterocyclic ring. In this case, a commercially available product may be used as such diamine, or the diamine may be synthesized by a method well known to those skilled in the art. Examples thereof include, but are not limited to, diamine derivatives represented respectively by the following chemical structural formulas:

N-(2-aminoethyl)imidazolidine

[Formula 53]

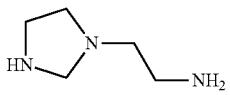

N-(2-aminoethyl)piperazine

[Formula 54]

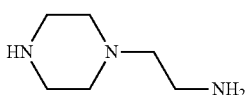

4-(2-aminoethyl)-1,4-diazepane

[Formula 55]

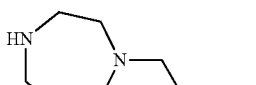

N-(2-aminopropyl)piperazine

[Formula 56]

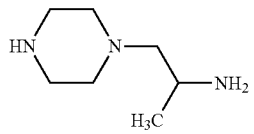

4-(2-aminoethyl)piperazin-2-one

[Formula 57]

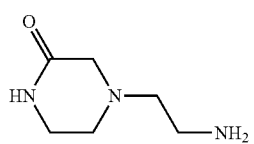

1-(2-aminoethyl)-piperidin-3-ol

[Formula 58]

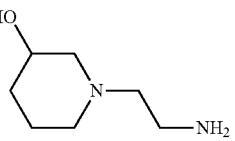

1-(2,5-dimethylpiperazin-1-yl)propan-2-amine

[Formula 59]

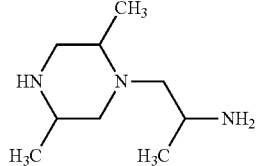

The substituted or unsubstituted 3- to 7-membered heterocyclic ring may be the same as the substituted or unsubstituted 3- to 7-membered heterocyclic ring mentioned above in relation to the substituent $R^2$ and/or $R^3$.

According to one embodiment, when $R^2$ and/or $R^3$ in the glycosylated linker moiety represented by the formula (I) according to the present invention is an alkyl group having 1 to 16 carbon atoms, a functional group, for example, an amino group, a carboxy group, a hydroxy group, or a thiol group may be introduced onto the alkyl group and, for example, a sugar chain, an amino acid, a polypeptide, a glycosylated amino acid, or a glycosylated polypeptide can be introduced via this functional group. For example, the functional group can be introduced to any position on the alkyl group by chemical synthesis according to a method well known to those skilled in the art. For example, a glycosylated amino acid and/or a glycosylated polypeptide can be bonded to the amino group through an amide bond, to the carboxy group through an amide bond or an ester bond, to the hydroxy group through an ester bond or an ether bond, or to the thiol group through a thioether bond or a thioester bond, though there is no limitation.

Examples of the aforementioned ethylenediamine derivatives having an alkyl group having 1 to 16 carbon atoms at a site corresponding to $R^2$ and/or $R^3$ in the glycosylated linker moiety represented by the formula (I) according to the present invention, and an amino group introduced thereto include the following derivatives (diamine derivatives):

3-(2-aminoethylamino)propylamine

[Formula 60]

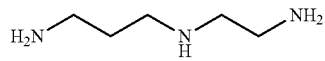

tris(2-aminoethyl)amine

[Formula 61]

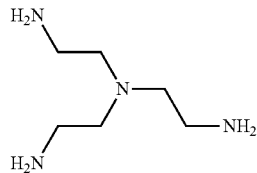

Alternatively, examples of the aforementioned ethylenediamine derivatives having an alkyl group having 1 to 16 carbon atoms at a site corresponding to $R^2$ and/or $R^3$ in the glycosylated linker moiety represented by the formula (I) according to the present invention, and a carboxy group introduced thereto include the following derivative:

[(2-aminoethyl)amino]acetic acid

[Formula 62]

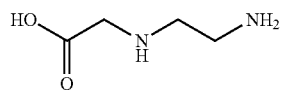

Alternatively, examples of the aforementioned ethylenediamine derivatives having an alkyl group having 1 to 16 carbon atoms at a site corresponding to $R^2$ and/or $R^3$ in the glycosylated linker moiety represented by the formula (I) according to the present invention, and a hydroxy group introduced thereto include the following derivatives:

3-(2-aminoethylamino)propanol

[Formula 63]

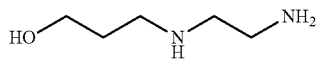

N,N-bis(2-hydroxyethyl)ethylenediamine

[Formula 64]

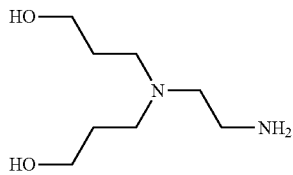

Alternatively, examples of the aforementioned ethylenediamine derivatives having an alkyl group having 1 to 16 carbon atoms at a site corresponding to $R^2$ and/or $R^3$ in the glycosylated linker moiety represented by the formula (I) according to the present invention, and a thiol group introduced thereto include the following derivative:

2-(2-aminoethylamino)ethanethiol

[Formula 65]

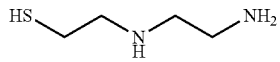

Those skilled in the art also understand similarly the introduction of, for example, a sugar chain, an amino acid, a polypeptide, a glycosylated amino acid, and/or a glycosylated polypeptide in the case where an alkyl group having 1 to 16 carbon atoms is present at a site corresponding to $R^2$ and/or $R^3$ in other glycosylated linkers or linkers according to the present invention.

Likewise, according to another embodiment, when $R^2$ and/or $R^3$ in the glycosylated linker moiety represented by the formula (I) according to the present invention is an aryl group having 5 to 16 carbon atoms, a functional group, for example, an amino group, a carboxy group, a hydroxy group, or a thiol group may be introduced onto the aryl group and, for example, a sugar chain, an amino acid, a polypeptide, a glycosylated amino acid, or a glycosylated polypeptide can be introduced via this functional group. For example, the functional group can be introduced to any position on the aryl group by chemical synthesis according to a method well known to those skilled in the art. For example, a glycosylated amino acid and/or a glycosylated polypeptide can be bonded to the amino group through an amide bond, to the carboxy group through an amide bond or an ester bond, to the hydroxy group through an ester bond or an ether bond, or to the thiol group through a thioether bond or a thioester bond, though there is no limitation.

Examples of the aforementioned ethylenediamine derivatives having an aryl group having 5 to 16 carbon atoms at a site corresponding to $R^2$ and/or $R^3$ in the glycosylated linker moiety represented by the formula (I) according to the present invention, and an amino group introduced thereto include the following derivatives:

N-(2-aminoethyl)-1,4-benzenediamine

[Formula 66]

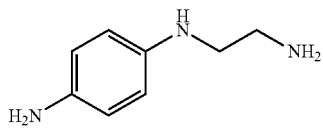

N-(2-aminoethyl)-1,2-benzenediamine

[Formula 67]

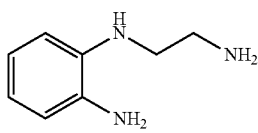

N-(2-aminoethyl)-1,3-benzenediamine

[Formula 68]

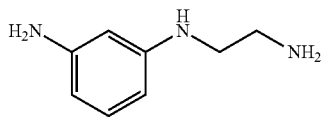

Alternatively, examples of the aforementioned ethylenediamine derivatives having an aryl group having 5 to 16 carbon atoms at a site corresponding to $R^2$ and/or $R^3$ in the glycosylated linker moiety represented by the formula (I) according to the present invention, and a carboxy group introduced thereto include the following derivative:

4-[(2-aminoethyl)amino]-benzoic acid

[Formula 69]

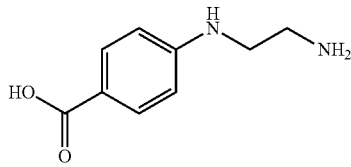

Alternatively, examples of the aforementioned ethylenediamine derivatives having an aryl group having 5 to 16 carbon atoms at a site corresponding to $R^2$ and/or $R^3$ in the glycosylated linker moiety represented by the formula (I) according to the present invention, and a hydroxy group introduced thereto include the following derivative:

4-[(2-aminoethyl)amino]-phenol

[Formula 70]

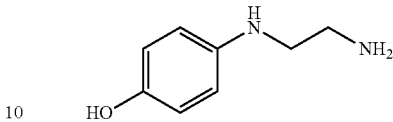

Those skilled in the art also understand similarly the introduction of, for example, a sugar chain, an amino acid, a polypeptide, a glycosylated amino acid, and/or a glycosylated polypeptide in the case where an aryl group having 5 to 16 carbon atoms is present at a site corresponding to $R^2$ and/or $R^3$ in other glycosylated linkers or linkers according to the present invention.

When $R^2$ and/or $R^3$ in the glycosylated linker moiety represented by the formula (I) according to the present invention is an alkyl group having 1 to 16 carbon atoms or an aryl group having 5 to 16 carbon atoms or when $R^2$ and $R^3$ form a 3- to 7-membered heterocyclic ring together with the nitrogen atom to which they are bonded, a thiol group introduced onto the alkyl group, the aryl group, or the heterocyclic ring permits direct bonding of a haloacetylated (e.g., bromoacetylated) complex-type sugar chain derivative (or a haloacetamidated complex-type sugar chain derivative) or the like, though there is no limitation.

Likewise, when $R^2$ and/or $R^3$ in the glycosylated linker moiety represented by the formula (I) according to the present invention is an alkyl group having 1 to 16 carbon atoms or an aryl group having 5 to 16 carbon atoms or when $R^2$ and $R^3$ form a 3- to 7-membered heterocyclic ring together with the nitrogen atom to which they are bonded, and when the sugar chain in the glycosylated amino acid or the glycosylated polypeptide to be bonded thereto is, for example, a sugar chain such as a haloacetylated complex-type sugar chain derivative, those skilled in the art should naturally understand that this sugar chain moiety can be bonded directly to the glycosylated linker moiety without the mediation of an amino acid moiety or a polypeptide moiety.

The haloacetylated complex-type sugar chain derivative (or the haloacetamidated complex-type sugar chain derivative) is a compound in which a hydroxy group bonded to the C1 position of, for example, a complex-type asparagine-linked sugar chain is substituted by —NH—$(CH_2)_a$—(CO)—$CH_2X$ (wherein X represents a halogen atom, and a represents an integer and is preferably an integer of 0 to 4, though there is no limitation unless it inhibits the linker functions of interest).

According to one embodiment, reaction conditions for replacing at least one hydrogen atom in the predetermined substituent of the linker moiety bonded to the physiologically active substance with a sugar chain, a glycosylated amino acid (the amino acid may be, for example, asparagine), and/or a glycosylated polypeptide (for example, at an asparagine residue in the polypeptide) are not limited and may be appropriately selected on the basis of a method well known to those skilled in the art. For example, the replacement can be carried out by the reaction of the sugar chain, the glycosylated amino acid, and/or the glycosylated polypeptide in the presence of the activator and the auxiliary amine.

According to another embodiment, reaction conditions for replacing at least one hydrogen atom in the predetermined substituent of the linker moiety bonded to the physiologically active substance with an amino acid (e.g., cysteine) and/or polypeptide moiety (for example, at a cysteine residue in the polypeptide) are not limited and may be appropriately selected on the basis of a method well known to those skilled in the art. For example, the replacement can be carried out by the introduction of Cys to the desired glycosylation site by a solid-phase synthesis method, a liquid-phase synthesis method, or the like. In such a case, reaction conditions for further adding a sugar chain to the amino acid and/or the polypeptide after the replacement are not limited and may be appropriately selected on the basis of a method well known to those skilled in the art. For example, a haloacetylated complex-type sugar chain derivative is reacted with the thus-obtained compound containing unprotected Cys so that the sugar chain is reacted with the thiol group of unprotected Cys to bond the sugar chain to the compound. The reaction is preferably carried out at usually 0 to 80° C., preferably 10 to 60° C., more preferably 15 to 35° C., in a phosphate buffer solution, a tris-HCl buffer solution, a citrate buffer solution, or a mixed solution thereof. The reaction time is not limited and may be usually approximately 10 minutes to 24 hours, preferably, usually approximately 30 minutes to 5 hours. After the completion of the reaction, the resulting compound may be appropriately purified by a method known in the art (e.g., HPLC). In this context, the haloacetylation may be, for example, chloroacetylation, bromoacetylation, or iodoacetylation. The haloacetylated complex-type sugar chain derivative may mean, for example, a haloacetylated product of a complex-type sugar chain such as a biantennary complex-type sugar chain, a triantennary complex-type sugar chain, or a tetraantennary complex-type sugar chain. For the haloacetylation method and manner of the sugar chain, see, for example, International Publication No. WO 2005/10053 (US2007060543 (A1)). Also, the method and manner are generally known to those skilled in the art.

According to one embodiment, the linker moiety used in the method for producing the compound comprising a glycosylated linker moiety and a physiologically active substance moiety or the salt thereof according to the present invention is represented by the formula (I') mentioned above, wherein each substituent and the wavy line are as defined above.

In this context, preferably, at least one hydrogen atom bonded to the alkyl group, the aryl group, or a nitrogen atom present in the heterocyclic ring is replaced by a glycosylated amino acid or a glycosylated polypeptide. More preferably, the replacement is a bond at the site of the amino acid or the polypeptide in the "glycosylated amino acid or glycosylated polypeptide".

According to a preferred embodiment, the linker moiety used in the method for producing the compound comprising a glycosylated linker moiety and a physiologically active substance moiety or the salt thereof according to the present invention is not limited and may be a linker moiety represented by the following formula (II') instead of the linker moiety represented by the formula (I') mentioned above:

[Formula 71]

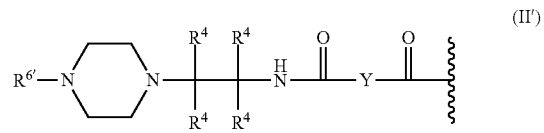

(II')

in the formula (II'), $R^4$, Y, and the wavy line are as defined above respectively, and $R^{6'}$ represents a hydrogen atom.

In such a case, for obtaining the glycosylated linker moiety, the hydrogen atom represented by $R^{6'}$ in the linker moiety is further replaced by a sugar chain, a glycosylated amino acid, or a glycosylated polypeptide (according to one embodiment, the hydrogen atom represented by $R^{6'}$ in the linker moiety is preferably replaced by a glycosylated amino acid or a glycosylated polypeptide, and the replacement is preferably a bond at the site of the amino acid or the polypeptide in the "glycosylated amino acid or glycosylated polypeptide", though there is no limitation).

According to a preferred embodiment, the hydrogen atom of $R^{6'}$ in the linker moiety represented by the formula (II') may be replaced by glycosylated asparagine (the asparagine is protected at its backbone amino group with a protective group) to form the structure of a glycosylated linker moiety represented by the formula (IIIa), though there is no limitation.

[Formula 72]

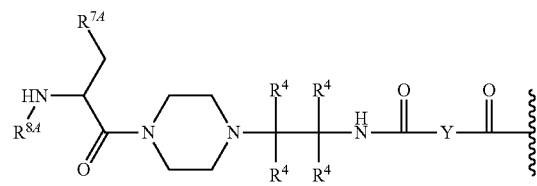

(IIIa)

in the formula (IIIa), $R^4$, Y, and the wavy line are as defined above respectively, $R^{74}$ represents —CONH-sugar chain, and $R^{84}$ represents a protective group such as an acyl group having 1 to 16 carbon atoms, an Fmoc group, a Boc group, a Z group, a Troc group, or an Alloc group.

The protective group represented by $R^{84}$ may be further replaced by a hydrogen atom, an amino acid, a polypeptide, a sugar chain, a glycosylated amino acid, or a glycosylated polypeptide. According to one embodiment, when $R^{84}$ is a glycosylated amino acid or a glycosylated polypeptide, the bonding of $R^{84}$ to the nitrogen atom is preferably a bond at the site of the amino acid or the polypeptide in the "glycosylated amino acid or glycosylated polypeptide".

According to an alternative preferred embodiment, the hydrogen atom of $R^{6'}$ in the linker moiety represented by the formula (II') may be replaced by cysteine protected at its backbone amino group with a protective group to form the structure of a linker moiety represented by the formula (III'), though there is no limitation.

[Formula 73]

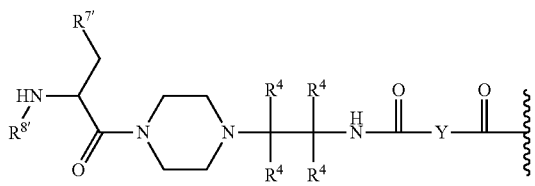

(III')

in the formula (III'),
$R^4$, Y, and the wavy line are as defined above respectively,
$R^{7'}$ represents —SH, and
$R^{8'}$ represents a protective group such as an acyl group having 1 to 16 carbon atoms, an Fmoc group, a Boc group, a Z group, a Troc group, or an Alloc group.

In this context, the protective group represented by $R^{8'}$ may be further replaced by a hydrogen atom, an amino acid, a polypeptide, a sugar chain, a glycosylated amino acid, or a glycosylated polypeptide. According to one embodiment, when $R^{8'}$ is a glycosylated amino acid or a glycosylated polypeptide, the bonding of $R^{8'}$ to the nitrogen atom is preferably a bond at the site of the amino acid or the polypeptide in the "glycosylated amino acid or glycosylated polypeptide".

The hydrogen atom in the —SH represented by $R^{7'}$ may be replaced by —CH$_2$—CONH-sugar chain to form the glycosylated linker moiety.

According to one embodiment, the present invention preferably provides a compound or a salt thereof obtainable by any of the production methods mentioned above. The obtainable compound or salt thereof is not limited to those produced by any of the production methods mentioned above and also includes those produced by other production methods.

According to another embodiment, the present invention preferably provides a compound or a salt thereof obtained by any of the production methods mentioned above.

According to a preferred embodiment, by use of the glycosylated linker of the present invention, a physiologically active substance can be readily dissolved, as the compound comprising a glycosylated linker moiety and a physiologically active substance moiety or the salt thereof according to the present invention, in an aqueous solution or an emulsion prepared from the aqueous solution, regardless of whether or not the physiologically active substance is poorly soluble. After the dissolution, the glycosylated linker moiety can be cleaved to release the unmodified physiologically active substance.

According to a preferred embodiment, the glycosylated linker moiety according to the present invention can be cleaved in an enzyme- or light-independent manner from the compound comprising a glycosylated linker moiety and a physiologically active substance moiety or the salt thereof according to the present invention. Specifically, the glycosylated linker moiety may be cleaved by autohydrolysis from the "compound comprising a glycosylated linker moiety and a physiologically active substance moiety or the salt thereof" through its intramolecular catalysis. However, the cleavage is not intended to exclude, for example, biological cleavage such as cleavage by an enzyme present in vivo (e.g., in the case of an amide bond, examples of the enzyme include amidase; and in the case of an ester bond, examples of the enzyme include esterase), or chemical cleavage such as cleavage by light.

In the present specification, the "self-cleavage" or the "autocatalytic cleavage" means that in the compound comprising a glycosylated linker moiety and a physiologically active substance moiety or the salt thereof according to the present invention, the bond between the glycosylated linker moiety and the physiologically active substance moiety is cleaved by autohydrolysis (hydrolysis for which a foreign factor such as an enzyme or light is unnecessary) as a result of activation by intramolecular catalysis within the linker moiety.

According to a preferred embodiment, a feature of the compound of the present invention or the salt thereof is that after the dissolution in an aqueous solution or an emulsion, the cleavage of the glycosylated linker moiety is accelerated in a manner dependent on pH and/or temperature (pH- and/or temperature-dependent cleavage). The compound of the present invention or the salt thereof and the glycosylated linker of the present invention may be preserved, for example, at a low temperature (e.g., −80° C. to 4° C.) and/or a low pH (e.g., pH 1 to pH 4). The step of preparing the "compound comprising a glycosylated linker moiety and a physiologically active substance moiety, or the salt thereof" by bonding the physiologically active substance to the glycosylated linker moiety may be carried out, for example, at a low temperature (e.g., 0° C. to 25° C.) and/or a low pH (e.g., pH 1 to pH 7). The compound comprising a glycosylated linker moiety and a physiologically active substance moiety or the salt thereof according to the present invention and the glycosylated linker of the present invention may be stabilized by the protection of the N-terminal amino group of the glycosylated amino acid with a protective group such as an acyl group having 1 to 16 carbon atoms, an Fmoc group, a Boc group, a Z group, a Troc group, or an Alloc group.

Preferably, the compound of the present invention or the salt thereof may be used at a temperature and a pH close to physiological conditions (e.g., the in vivo physiological environment of a mammal or a similar environment, for example, 35° C. to 43° C. and pH 6.8 to 7.8).

According to a preferred embodiment, by use of the compound of the present invention or the salt thereof, the physiologically active substance can be efficiently dissolved in an aqueous solution or an emulsion prepared from the aqueous solution. Thus, according to a preferred embodiment, by use of the compound of the present invention or the salt thereof, even a low water-soluble (poorly soluble) physiologically active substance can be filter-sterilized. According to a preferred alternative embodiment, by use of the compound of the present invention or the salt thereof, even a low water-soluble physiologically active substance can be administered to an organism.

According to a preferred alternative embodiment, by use of the compound of the present invention or the salt thereof, even a highly water-soluble physiologically active substance can be dissolved with higher efficiency in an aqueous solution or an emulsion prepared from the aqueous solution. Thus, advantageously, the present invention can reduce "losses" that may be caused by the insolubility, etc., of a substance in the course of preparing a preparation containing an expensive physiologically active substance or administering such a preparation.

According to a preferred alternative embodiment, the glycosylated linker of the present invention having a known half-life in a solvent can be appropriately selected, thereby controlling the release duration and timing of the unmodified physiologically active substance to be released into an in vitro environment or an in vivo environment. The glycosylated linker of the present invention is advantageous to the delivery of, for example, a physiologically active substance desired to exert its effects immediately at the desired site after administration to an organism.

According to a particularly preferred embodiment, the compound comprising a glycosylated linker moiety and a physiologically active substance moiety or the salt thereof according to the present invention can provide improved water solubility compared with an unmodified physiologically active substance. The improved water solubility is not limited and is preferably 2 times to 1,000,000 times, more preferably 10 times to 1,000,000 times, further preferably 100 times to 1,000,000 times the water solubility of the unmodified physiologically active substance in terms of molar concentration. Those skilled in the art can appropriately select the compound comprising a glycosylated linker moiety and a physiologically active substance moiety or the salt thereof according to the present invention or the glycosylated linker of the present invention having necessary solubility according to the use and purpose of the physiologically active substance.

The molar absorption coefficient (specific absorbance) necessary for determining the solubility of the compound comprising a glycosylated linker moiety and a physiologically active substance moiety or the salt thereof according to the present invention, or the unmodified physiologically active substance may be determined by ultraviolet-visible spectroscopy (e.g., a wavelength in the ultraviolet-visible region, such as 280 nm) using, as a sample, a solution having a known protein concentration measured by a method generally known to those skilled in the art, for example, an amino acid composition analysis method or a nitrogen quantification method.

The composition of the present invention comprises one or more compounds of the present invention or salts thereof and optionally contains one or more additional components (active and/or inert ingredient(s)). The composition of the present invention is not particularly limited by its use and may be used in, for example, an assay system (e.g., an in vitro assay system). Also, the pharmaceutical composition of the present invention is a composition suitable for medical uses and is formulated in the form of an ordinary pharmaceutical composition using diluents or excipients usually used, such as a filler, an expander, a binder, a wetting agent, a disintegrant, a surfactant, and a lubricant. Examples of such a pharmaceutical composition include, but are not limited to, tablets, pills, powders, solutions, suspensions, emulsions, granules, capsules, suppositories, and injections. The medical uses of the pharmaceutical composition may target diseases or disorders involving a physiologically active substance contained as the physiologically active substance moiety in the composition. When the physiologically active substance is, for example, GLP-1 or its derivative, the medical uses may target diabetes mellitus or the like. Those skilled in the art can similarly understand other medical uses, also in view of the types of diseases or disorders involving each physiologically active substance.

In the present specification, the pharmacologically acceptable carrier is not particularly limited. The addition of the pharmacologically acceptable carrier may influence the absorbability or concentration in blood of the compound of the present invention or the salt thereof and cause change in its disposition.

Particularly preferably, when an antigen is used as the physiologically active substance, the compound of the present invention or the salt thereof and the pharmaceutical composition of the present invention comprising the same may be used as a vaccine. According to a preferred embodiment, for example, even a poorly soluble antigen can be dissolved, as the compound of the present invention or the salt thereof, in an aqueous solution or an emulsion. In addition, the unmodified antigen can be released after cleavage of the glycosylated linker moiety in vivo. Preferably, the compound of the present invention or the salt thereof and the glycosylated linker of the present invention can be used in the development of various vaccines such as peptide vaccines.

In the present specification, the vaccine (also called immunogenic composition) means a substance capable of causing immune response when inoculated into an animal. The vaccine may contain an antigen or may express the antigen, thereby inducing immune response against the antigen. The pharmaceutical composition of the present invention used as a vaccine can be used not only in the prevention or treatment of viral infections, bacterial infections (sepsis, etc.), and communicable diseases but in the treatment, etc., of any disease that may be related to immune response, for example, cancers and autoimmune diseases (e.g., type I diabetes mellitus, multiple sclerosis, and articular rheumatism).

The antigen is a molecule containing one or more epitopes and can be any molecule capable of inducing antigen-specific immune response by stimulating the immune system of a host. The immune response may be humoral immune response and/or cellular immune response. Although approximately 3 to several (e.g., 5 or 6) amino acids may serve as one epitope, one epitope in a protein typically contains 7 to 15 amino acids, for example, 8, 9, 10, 12, or 14 amino acids. According to one embodiment, the antigen is preferably a peptide or an epitope. When the antigen is used in the treatment of cancers, such a peptide is also called cancer peptide.

Also, the pharmaceutical composition of the present invention (including that for use as a vaccine) may be administered to an organism. The pharmaceutical composition of the present invention is not particularly limited by its administration method and is administered by a method suitable for various dosage forms, the age, sex, and disease severity of a patient, and other conditions. Examples of methods for administering tablets, pills, solutions, suspensions, emulsions, granules, and capsules include oral administration. Alternatively, an injection can be administered either alone or as a mixture with an ordinary fluid replacement such as glucose or an amino acid through an intravenous, intramuscular, intracutaneous, subcutaneous, or intraperitoneal route. A suppository is administered into the rectum. Particularly, the pharmaceutical composition of the present invention used as a vaccine may be administered through subcutaneous injection, intramuscular injection, an oral route, a stump form, intracutaneous injection, or the like.

The dose of the pharmaceutical composition of the present invention (including that for use as a vaccine) can be appropriately selected according to the usage, the age, sex, and disease severity of a patient, and other conditions. The frequency of administration can be appropriately selected according to the usage, the age, sex, and disease severity of a patient, and other conditions. For example, 3 times/day, twice/day, once/day, or less frequent administration (e.g., once/week or once/month) according to the stability thereof in blood may be selected. The pharmaceutical composition of the present invention may confer sustained release properties to the physiologically active substance by gradual cleavage of the sugar chain linker moiety. Alternatively, the pharmaceutical composition of the present invention may confer fast acting properties to the physiologically active substance by rapid cleavage of the sugar chain linker moiety.

In a certain aspect, the present invention relates to use of the glycosylated linker or the compound comprising a glycosylated linker moiety and a physiologically active substance moiety or the salt thereof for the production of a therapeutic or preventive drug for diseases or disorders targeted by a physiologically active substance. In an alternative aspect, the present invention also relates to use of the glycosylated linker or the compound comprising a glycosylated linker moiety and a physiologically active substance moiety or the salt thereof for the treatment or prevention, etc., of diseases or disorders targeted by a physiologically active substance.

The glycosylated linker of the present invention in which a sugar chain having biodegradable nature is added to a linker has a reduced adverse effect on organisms compared with a PEG-added linker. As a result, long-term administration to organisms is expected.

In the present specification, the aqueous solution may be any liquid of a substance (e.g., acetate) dissolved in water as a solvent and includes every aqueous solution generally known to those skilled in the art and every novel aqueous solution.

In the present specification, the emulsion is not limited and may be any preparation from the aqueous solution. The emulsion may be an oil-in-water (O/W) emulsion or a water-in-oil (W/O) emulsion, though there is no limitation. Methods generally known to those skilled in the art may be used as methods for dispersion and emulsification in the aqueous solution.

The subject to which the compound of the present invention or the salt thereof, or the pharmaceutical composition of the present invention is administered (applied) includes, but is not limited to, animals (humans, nonhuman mammals (e.g., mice, rats, dogs, cats, rabbits, cattle, horses, sheep, goats, and pigs), and non-mammalian animals (e.g., fish, reptiles, amphibians, and bird)), plants, insects, bacteria, and cells derived therefrom (including cultured cells), tissues, and organs, etc. Alternatively, the subject may be an artificial environment (e.g., an in vitro reaction system). Preferably, the subject according to the present invention is a human.

The terms used in the present specification are given for illustrating particular embodiments and are not intended to limit the present invention.

The term "comprising" used in the present specification means that described items (members, steps, factors, numbers, etc.) are present, and does not exclude the presence of the other items (members, steps, factors, numbers, etc.), unless the context evidently requires different interpretation.

According to one embodiment, the compound comprising a glycosylated linker moiety and a physiologically active substance moiety or the salt thereof according to the present invention may consist substantially of the physiologically active substance moiety and the glycosylated linker moiety (in other words, the compound comprising a glycosylated linker moiety and a physiologically active substance moiety or the salt thereof according to the present invention may contain other components without influencing the basic or essential constitution of the present invention) or may consist only of the physiologically active substance moiety and the glycosylated linker moiety, though there is no limitation.

All terms (including technical terms and scientific terms) used herein have the same meanings as those understood in a broad sense by those skilled in the art to which the present invention belongs, unless otherwise defined. The terms used herein should be interpreted as having meanings consistent with meanings in the present specification and related technical fields and should not be interpreted in an idealized or excessively formal sense, unless otherwise defined.

The embodiments of the present invention may be described with reference to a schematic diagram. However, such a schematic diagram may be exaggerated for the purpose of clear illustration.

The terms such as "first" or "second" are used for expressing various factors. However, these factors are understood to be not limited by these terms. These terms are used merely for differentiating one factor from the other factors. For example, the first factor may be described as the second factor, and vice versa, without departing from the scope of the present invention.

Those skilled in the art understand that, for example, the phrase "alkyl group having 1 to 16 carbon atoms" in the present specification specifically represents each individual of alkyl groups having 1, 2, 3, 4, 5, 6, 7, 8, 9, 10, 11, 12, 13, 14, 15, or 16 carbon atoms.

Any numerical value used in the present specification for indicating the content of a component or a numerical range is interpreted as including the meaning of the term "approximately", unless otherwise specified. For example, the term "10 times" is interpreted as meaning "approximately 10 times", unless otherwise specified.

All literatures cited herein should be incorporated herein by reference in their entirety. Those skilled in the art understand the contents of related disclosure in these prior technical literatures as a part of the present specification by reference without departing from the spirit and scope of the present invention according to the context of the present specification.

Hereinafter, the present invention will be described in more detail with reference to Examples. However, the present invention can be embodied in various aspects and must not be interpreted as being limited to Examples described herein.

EXAMPLES

Some abbreviations used in Examples will be described below:
Ac: Acetyl (group)
AcOH: Acetic acid
Alloc group: Allyloxycarbonyl group Asn: Asparagine
Boc: tert-Butyloxycarbonyl group
Cys: Cysteine
DIC: Diisopropylcarbodiimide
DIPEA: N,N-Diisopropylethylamine
DMF: N,N-Dimethylformamide
DMSO: Dimethyl sulfoxide
DTT: Dithiothreitol
ESI-MS: Electrospray ionization mass spectrometry
Fmoc (group): 9-Fluorenylmethyloxycarbonyl (group)
GlcNAc: N-Acetylglucosamine
HCTU: O-(6-Chloro-1H-benzotriazol-1-yl)-N,N,N',N'-tetramethyluronium hexafluorophosphate
HMPB: 4-Hydroxymethyl-3-methoxyphenoxy-butyric acid
HOBt: 1-Hydroxybenzotriazole
HPLC: High-performance liquid chromatography
$H_2O$: Water
Leu: Leucine or leucine residue
ln 2: $\log_e 2$
MSNT: 1-(Mesitylene-2-sulfonyl)-3-nitro-1,2,4-triazole
PBS: Phosphate-buffered saline
Pbf: 2,2,4,6,7-Pentamethyldihydrobenzofuran-5-sulfonyl
tBu: tert-Butyl group
TBTU: O-(1H-Benzotriazol-1-yl)N,N,N',N'-tetramethyluronium
TFA: Trifluoroacetic acid
Trt: Trityl group Example 1

(Synthesis of Glycosylated (Asn (Asialo)-Type) Linker-Chemerin 9 Conjugate (Compound 1) and Cleavage Evaluation of Glycosylated Linker Moiety)

For the purpose of developing a linker capable of further enhancing the solubility of a physiologically active substance, an attempt was made to synthesize a novel compound composed of a glycosylated linker having a highly water-soluble sugar chain added to a linker, and a peptide. The sugar chain used was an asialo sugar chain. The peptide used was chemerin 9. The compound composed of the asialo sugar chain-attached linker and the peptide (glycosylated (Asn (asialo)-type) linker-chemerin 9 conjugate (compound 1 (SEQ ID NO: 6)) was synthesized as mentioned later.

Short-chain chemerin 9 was selected as an example of the physiologically active substance. Chemerin 9 (9 residues, sequence: YFPGQFAFS) corresponds to the 4th to 12th amino acid residues of SEQ ID NO: 31 (18 amino acid residues) in the Sequence Listing of U.S. Patent Publication No. 2003/096299. Chemerin 9 has agonistic activity against a G protein coupled receptor ChemR23 and therefore has the potential as a therapeutic and/or preventive agent for immunological diseases, inflammatory diseases, and diabetes mellitus. Chemerin 9, however, is known to undergo degradation by protease in vivo and be therefore very unstable (Japanese Patent Laid-Open No. 2010-229093). Although its production method, reaction conditions and temperature, etc., are known in the art and are obvious to those skilled in the art, chemerin 9 may be synthesized according to a method described in the literature.

(Synthesis of Glycosylated (Fmoc-Asn (Asialo)-Type) Linker-Chemerin 9 Conjugate (Compound 7))

In order to synthesize the glycosylated (Asn (asialo)-type) linker-chemerin 9 conjugate (compound 1), first, glycosylated (Fmoc-Asn (asialo)-type) linker-chemerin 9 conjugate (compound 7) (SEQ ID NO: 5) was synthesized [Formula 74] as described in FIG. 5.

Amino-PEGA resin (manufactured by Merck KGaA) (200 µmol) was placed in a column for solid-phase synthesis and washed with DMF. A DMF (5.0 mL) solution containing HMPB (121.2 mg, 0.504 mmol), TBTU (161.7 mg, 0.504 mmol), and N-ethylmorpholine (57.3 µL, 0.495 mmol) was added thereto, and the mixture was shaken at room temperature for 3 hours. After washing with DMF and dichloromethane, a dichloromethane (10 mL) solution containing Fmoc-Ser(tBu)-OH (383.1 mg, 1.00 mmol), MSNT (296.4 mg, 1.00 mmol), and N-methylimidazole (55.8 µL, 0.700 mmol) was added thereto, and the mixture was shaken at room temperature for 3 hours. After washing with dichloromethane and DMF, DMF (4 mL), pyridine (1.2 mL), and acetic anhydride (189 µL, 2.00 mmol) were added thereto sequentially, and the mixture was shaken at room temperature. After 1 hour, the resin was washed with DMF and dichloromethane.

Fmoc groups in an aliquot (100 µmol) of the resin thus obtained were removed by treatment with 20% piperidine in DMF for 15 minutes. After washing with DMF, chemerin 9 protected with tBu and Trt was synthesized on the resin by a solid-phase peptide synthesis method according to the Fmoc method using a Prelude (trademark) peptide synthesizer. The condensation reaction was carried out in DMF using HCTU as a condensing agent.

Fmoc groups in an aliquot (70 µmol) of the resin thus obtained were removed by treatment with 20% piperidine in DMF to obtain a resin bonded to chemerin 9 protected with tBu and Trt (compound 12) (SEQ ID NO: 2). After washing with DMF and dichloromethane, phthalic anhydride (104 mg, 0.702 mmol), dichloromethane (2.1 mL), and pyridine (126 µL) were added thereto sequentially, and the mixture was shaken at room temperature for 3 hours. After washing with dichloromethane and DMF, a DMF (1.75 mL) solution of HOBt (47.3 mg, 0.35 mmol) and DIC (51.2 µL, 0.33 mmol) were added thereto, and the mixture was shaken at room temperature. After 15 minutes, N-(2-aminoethyl)piperazine (46.1 µL, 0.35 mmol) was added thereto, and the mixture was shaken at room temperature for 1 hour. After washing with DMF, this condensation operation was repeated once, and the resin was then washed with DMF to obtain a resin bonded to chemerin 9 protected with tBu and Trt and a linker moiety (compound 13) (SEQ ID NO: 3).

To an aliquot (20 µmol) of the obtained resin (compound 13), Fmoc-Asn (asialo)-OH (compound 14) (75 mg, 38 µmol) represented by the following chemical formula:

[Formula 75]

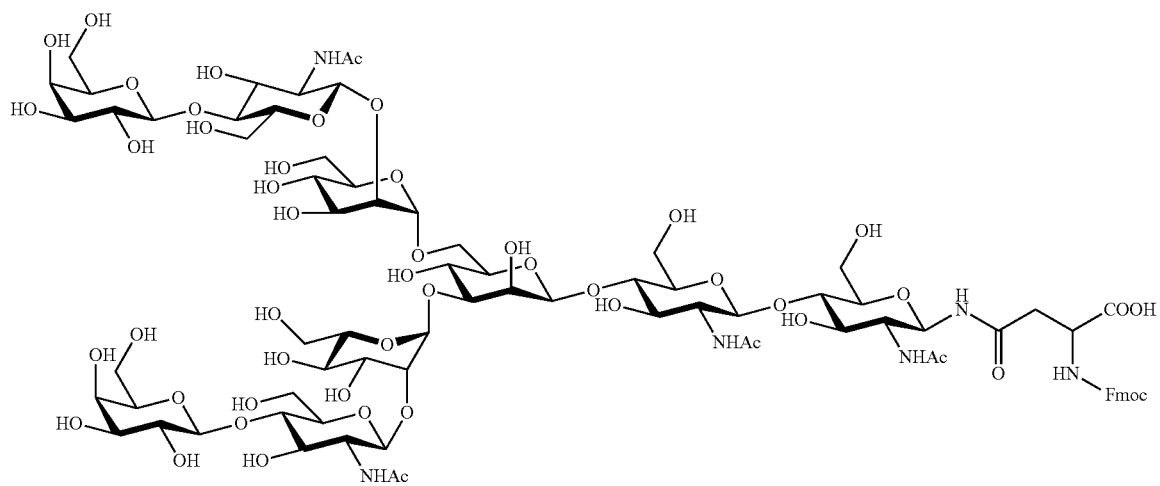

14 a DMSO-DMF (1/1, v/v, 833 μL) solution, TBTU (16.1 mg, 50 μmol), and DIPEA (13.1 μL, 75.2 μmol) were added sequentially, and the mixture was shaken at room temperature for 4.5 hours. The resin was washed with DMF and dichloromethane to obtain a resin bonded to a compound having chemerin 9 protected with tBu and Trt (compound 15) (SEQ ID NO: 4). To the resin (compound 15), TFA: water:triisopropylsilane:ethanedithiol (90:2.5:5:2.5, respectively, parts by volume) were added, and the mixture was shaken at room temperature for 3 hours. To the filtrate, cooled diethyl ether was added to obtain the compound as precipitates. The compound was purified by HPLC [column: SHISEIDO CAPCELL PAK C18 UG-120 (5 μm), ϕ20×250 mm, flow rate: 7.0 mL/min, eluent A: 0.1% TFA in water, eluent B: 0.09% TFA/10% water/90% acetonitrile, gradient A:B=65:35→40:60 (30 min) linear concentration gradient elution] to obtain the glycosylated (Fmoc-Asn (asialo)-type) linker-chemerin 9 conjugate (compound 7) (8.6 mg).

ESI-MS: (m/z) calcd for $C_{149}H_{201}N_{19}O_{64}$ $[M+3H]^{3+}$ 1094.4, $[M+4H]^{4+}$ 821.1, found 1094.4, 821.1.

Example 2

(Synthesis of Glycosylated (Asn (Asialo)-Type) Linker-Chemerin 9 Conjugate (Compound 1))

[Formula 76]

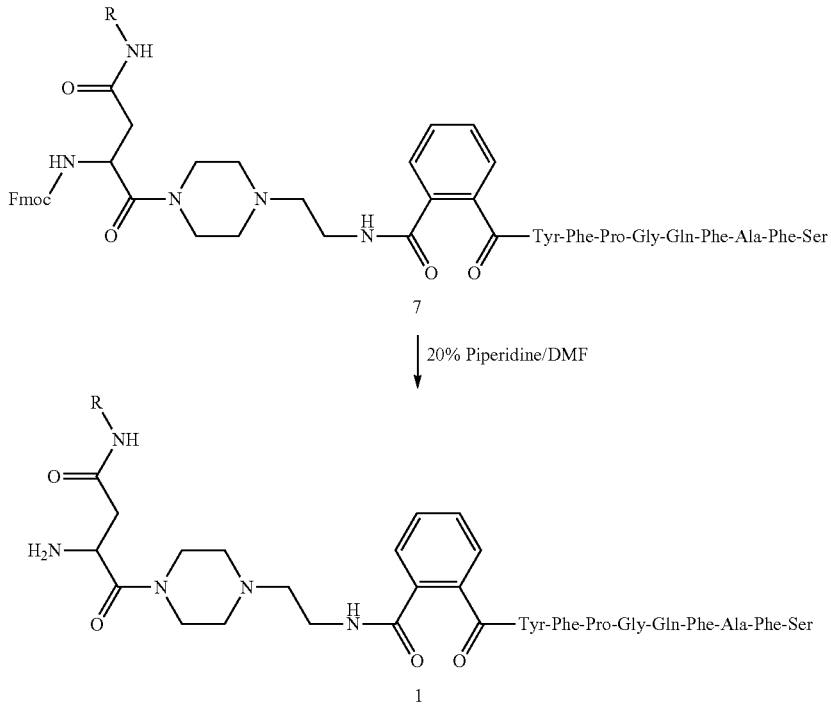

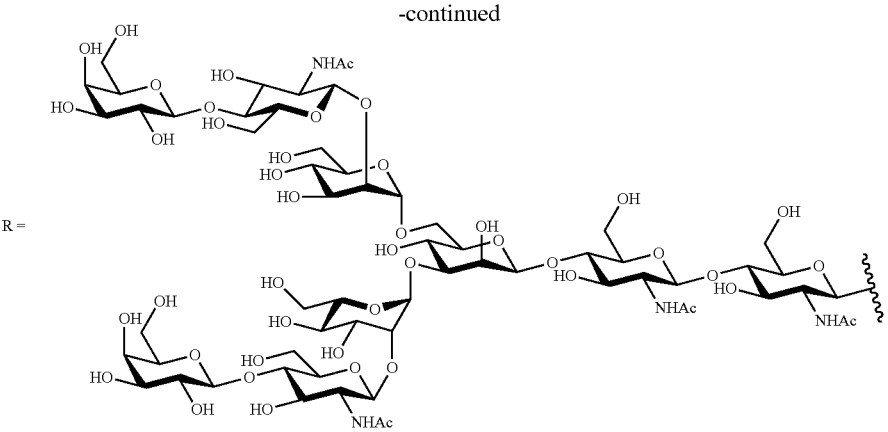

wherein R represents the chemical formula shown above.

The glycosylated (Fmoc-Asn (asialo)-type) linker-chemerin 9 conjugate (compound 7) (4.0 mg, 1.2 μmol) was treated with a 20% solution of piperidine in DMF (60 μL) for 5 minutes to deprotect Fmoc groups. After addition of acetic acid (57.5 μL) and a 0.1% aqueous TFA solution (1300 μL), the resulting compound was purified by HPLC [column: SHISEIDO CAPCELL PAK C18 UG-120 (5 μm), (φ4.6× 250 mm, flow rate: 0.7 mL/min, eluent A: 0.1% TFA in water, eluent B: 0.09% TFA/10% water/90% acetonitrile, gradient A:B=80:20→50:50 (30 min) linear concentration gradient elution] to obtain the glycosylated (Asn (asialo)-type) linker-chemerin 9 conjugate (compound 1) (3.5 mg, 1.1 μmol, 92%). ESI-MS: (m/z) calcd for $C_{134}H_{191}N_{19}O_{62}$ $[M+3H]^{3+}$ 1020.4, $[M+4H]^{4+}$ 765.6, found 1020.4, 765.6.

Example 3

(Cleavage Evaluation of Glycosylated Linker Moiety of Glycosylated (Asn (Asialo)-Type) Linker-Chemerin 9 Conjugate (Compound 1) in Aqueous Solution)

(a. Release and Production of Unmodified Chemerin 9 by Self-Cleavage of Glycosylated (Asn (Asialo)-Type) Linker-Chemerin 9 Conjugate (Compound 1))

Subsequently, the autocatalytic cleavage behavior of the glycosylated linker moiety in an aqueous solution was traced for the glycosylated (Asn (asialo)-type) linker-chemerin 9 conjugate (compound 1) obtained as described above. The reaction is shown below.

[Formula 77]

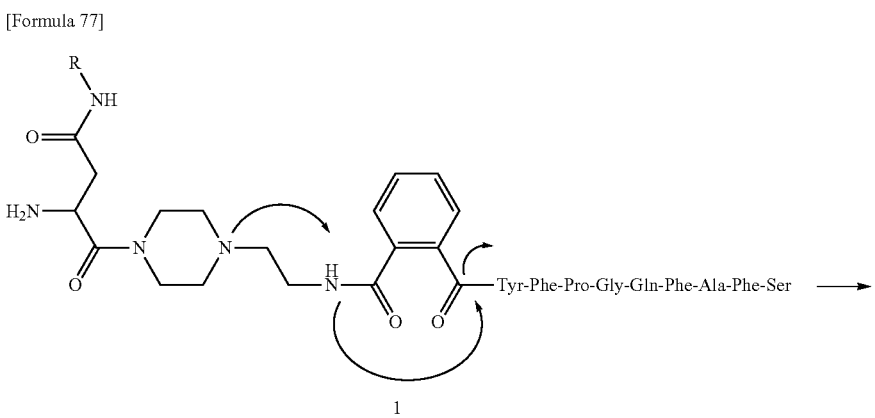

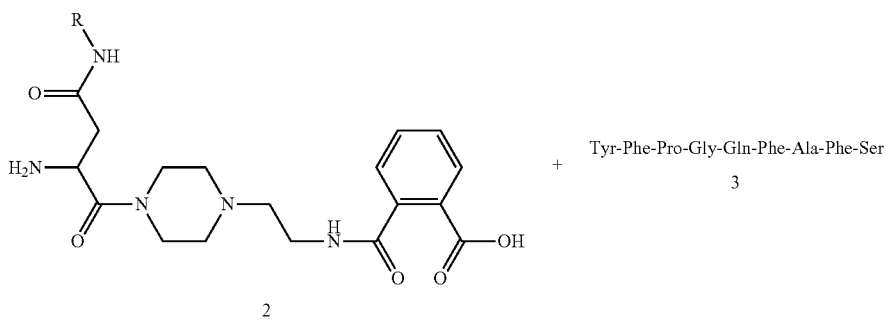

R = 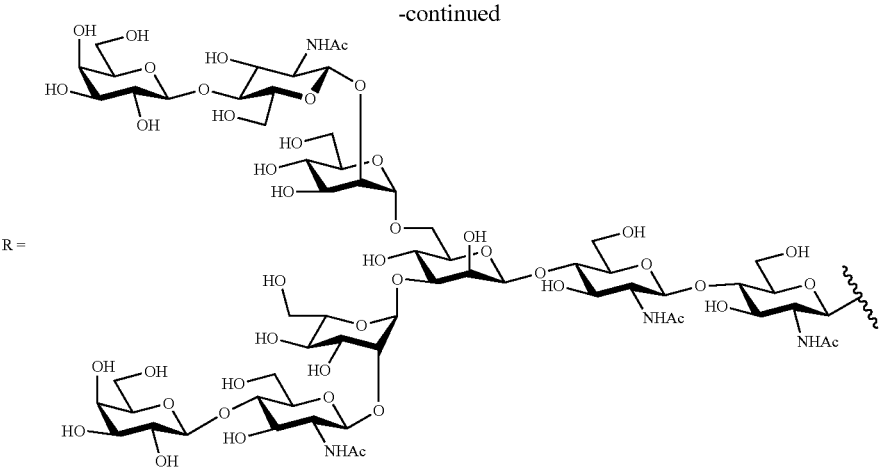

wherein R represents the chemical formula shown above.

The cleavage behavior was traced as follows:

The freeze-dried glycosylated (Asn (asialo)-type) linker-chemerin 9 conjugate (compound 1) was dissolved in a PBS solution (37° C., pH 7.4, 350 μL) and then left standing at 37° C. for incubation. Then, a portion (28 μL) of the PBS solution containing the glycosylated (Asn (asialo)-type) linker-chemerin 9 conjugate (compound 1) dissolved therein was sampled at given time intervals. To each sampled solution, a 0.5% aqueous TFA solution (28 μL) was added, and this solution was then frozen. The obtained solution was dissolved immediately before HPLC analysis, and a 50 μL aliquot thereof was injected and analyzed by HPLC [column: SHISEIDO CAPCELL PAK C18 UG-120 (5 μm), φ4.6×250 mm, flow rate: 0.7 mL/min, eluent A: 0.1% TFA in water, eluent B: 0.09% TFA/10% water/90% acetonitrile, gradient A:B=77:23→50:50 (20 min) linear concentration gradient elution]. The compound was detected using a diode array detector with a detection wavelength set to 220 nm. From the HPLC chromatogram and ESI-MS analysis, the cleavage of the glycosylated linker moiety was confirmed to proceed with time to release the unmodified chemerin 9 (compound 3) (SEQ ID NO: 1) (peak 3 indicated by the arrow in FIG. 1). After 6 hours into the test, the glycosylated (Asn (asialo)-type) linker-chemerin 9 conjugate (compound 1) was rarely present, whereas the unmodified chemerin 9 (compound 3) was present in a large amount.

After 6 hours, the reaction solution was analyzed by HPLC [column: SHISEIDO CAPCELL PAK C18 UG-120 (5 μm), φ4.6×250 mm, flow rate: 0.7 mL/min, eluent A: 0.1% TFA in water, eluent B: 0.09% TFA/10% water/90% acetonitrile, gradient A:B=95:5→95:5 (8 min) and subsequently A:B=95:5→5:95 (20 min) linear concentration gradient elution]. As a result, the peak of the glycosylated linker moiety (compound 2) was confirmed at a retention time of 9.6 minutes.

ESI-MS of compound 2: (m/z) calcd for $C_{80}H_{127}N_9O_{50}$ $[M+2H]^{2+}$ 1007.9, $[M+3H]^{3+}$ 672.3, found 1007.9, 672.2.

The area of the peak (corresponding to the glycosylated (Asn (asialo)-type) linker-chemerin 9 conjugate (compound 1)) indicated by the arrow 1 in FIG. 1 was plotted against incubation time to calculate the relative concentration ($C/C_0$) vs. time of the glycosylated (Asn (asialo)-type) linker-chemerin 9 conjugate (compound 1) (FIG. 2). The natural logarithm of the relative concentration was further plotted against incubation time to obtain a linear plot (FIG. 3) (wherein $C_0$ represents the initial concentration of the compound 1, and C represents the concentration of the compound 1 at an arbitrary time). FIG. 3 showed that the cleavage rate of the glycosylated linker was primary reaction.

Accordingly, a slope k of the linear plot obtained from FIG. 3 was substituted into the following formula:

$t_{1/2}=\ln 2/k$ (wherein k represents the slope of the linear plot)

to calculate an elimination half-life $t_{1/2}$ of the starting material (glycosylated (Asn (asialo)-type) linker-chemerin 9 conjugate (compound 1)). The elimination half-life was 1.2 hours.

(c. Temperature and pH Dependence of Glycosylated (Asn (Asialo)-Type) Linker-Chemerin 9 Conjugate (Compound 1))

Next, the autocatalytic cleavage of the glycosylated linker moiety was observed for the glycosylated (Asn (asialo)-type) linker-chemerin 9 conjugate (compound 1) under various temperature (4° C., 25° C., and 37° C.) and pH (pH 4.0 and pH 7.4) conditions.

TABLE 5

Elimination half-life of glycosylated (Asn (asialo)-type) linker-chemerin 9 conjugate (compound 1) under various conditions

| Entry | Solvent | | Reaction temperature | Half-life |
|---|---|---|---|---|
| 1 | Acetate buffer solution | (pH 4.0) | 37° C. | 4.4 hours |
| 2 | Acetate buffer solution | (pH 4.0) | 25° C. | 16.0 hours |
| 3 | Acetate buffer solution | (pH 4.0) | 4° C. | 10.4 days |
| 4 | PBS | (pH 7.4) | 37° C. | 1.2 hours |
| 5 | PBS | (pH 7.4) | 25° C. | 4.3 hours |
| 6 | PBS | (pH 7.4) | 4° C. | 43.1 hours |

Reference: 9.2 days at 4° C. in water

In the comparison of the half-life at the same temperature, the glycosylated linker moiety was found to be cleaved faster at a higher pH (comparison between Entries 1 and 4 (37° C.), comparison between Entries 2 and 5 (25° C.), and comparison between Entries 3 and 6 (4° C.)).

Furthermore, in the comparison of the half-life at the same pH, the glycosylated linker moiety was found to be cleaved faster at a higher temperature (comparison among Entries 1, 2, and 3 (pH 4.0), and comparison among Entries 4, 5, and 6 (pH 7.4)).

From these results, the present inventor found that the cleavage of the glycosylated linker moiety is promoted with increase in (i) temperature and (ii) pH.

Thus, in order to further examine the correlation between the structure of the compound and the autocatalytic cleavage of the glycosylated linker moiety, a plurality of compounds were synthesized as follows:

Example 4

(Synthesis of Glycosylated (Cys (GlcNAc)-Type) Linker-Chemerin 9 Conjugate (Compound 4))

[Formula 78] Synthesized as Described in FIG. 6.

To the resin bonded to chemerin 9 protected with tBu and Trt and a linker moiety (compound 13) (50 μmol), a DMF (1.25 mL) solution containing Fmoc-Cys(Trt)-OH (146.8 mg, 0.251 mmol), HOBt (33.8 mg, 0.250 mmol), and DIC (36.6 μL, 0.238 mmol) was added, and the mixture was shaken at room temperature for 1 hour for condensation operation. After washing with DMF, this condensation operation was repeated once. After washing with DMF and dichloromethane, an appropriate amount of TFA:water:triisopropylsilane:ethanedithiol (90:2.5:5:2.5, respectively, parts by volume) was added thereto, and the mixture was shaken at room temperature for 3 hours. Then, the resin was filtered off. To the filtrate, cooled diethyl ether was added to obtain the compound as precipitates. The obtained compound was purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient A:B=50:50→42.7:57.3 (22 min) linear concentration gradient elution] to obtain the compound 16 (SEQ ID NO: 7) (6.6 mg).

ESI-MS: (m/z) calcd for $C_{86}H_{98}N_{14}O_{18}S$ $[M+2H]^{2+}$ 824.4, found 824.4.

The compound 16 (6.6 mg, 4.0 μmol) was dissolved in a 20% solution of piperidine in DMF (1.0 mL) to deprotect Fmoc groups. After addition of acetic acid (1.0 mL) and 0.1% TFA in water (2.0 mL), the resulting compound was purified by HPLC [column: SHISEIDO CAPCELL PAK C18 UG-120 (5 μm), φ4.6×250 mm, flow rate: 0.7 mL/min, eluent A: 0.1% TFA in water, eluent B: 0.09% TFA/10% water/90% acetonitrile, gradient A:B=70:30→50:50 (30 min) linear concentration gradient elution] to obtain the compound 17 (SEQ ID NO: 8) (3.4 mg, 2.4 μmol, 60%).

ESI-MS: (m/z) calcd for $C_{71}H_{88}N_{14}O_{16}S$ $[M+2H]^{2+}$ 713.3, found 713.3.

The obtained compound 17 (2.2 mg, 1.5 μmol) and a dehydration condensation product of GlcNAc and 2-bromoacetamide (compound 18) (2.7 mg, 7.9 μmol) represented by the following chemical formula:

[Formula 79]

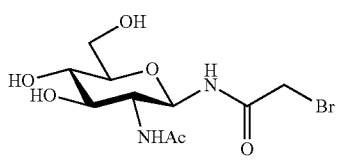

18 were dissolved in a 50 mM phosphate buffer solution (pH 7.4, 316 μL) containing 4.9 mM DTT and reacted at room temperature for 50 minutes. The reaction solution was purified by HPLC [column: SHISEIDO CAPCELL PAK C18 UG-120 (5 μm), 020×250 mm, flow rate: 7.0 mL/min, eluent A: 0.1% TFA in water, eluent B: 0.09% TFA/10% water/90% acetonitrile, gradient A:B=75:25→45:55 (20 min) linear concentration gradient elution] to obtain the glycosylated (Cys (GlcNAc)-type) linker-chemerin 9 conjugate (compound 4) (SEQ ID NO: 9) (1.8 mg, 1.1 μmol, yield: 73%).

ESI-MS: (m/z) calcd for $C_{81}H_{101}N_{16}O_{22}S$ $[M+2H]^{2+}$ 843.4, found 843.4.

Example 5

(Synthesis of Glycosylated (Cys (Asialo)-Type) Linker-Chemerin 9 Conjugate (Compound 5))

The glycosylated (Cys (asialo)-type) linker-chemerin 9 conjugate (compound 5) (SEQ ID NO: 10) was obtained through the same reaction as in the synthesis of the glycosylated (Cys (GlcNAc)-type) linker-chemerin 9 conjugate (compound 4) in Example 4 except that a dehydration condensation product of asialo sugar chain and 2-bromoacetamide (compound 19) represented by the following chemical formula:

[Formula 80]

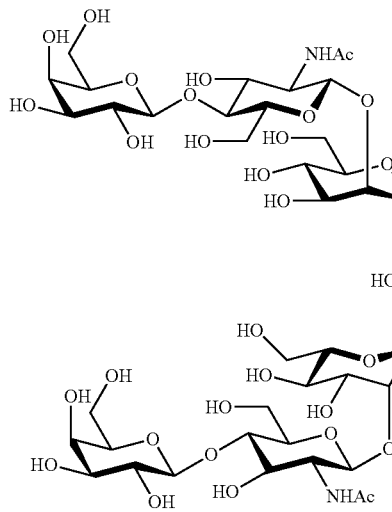

19 was used instead of the dehydration condensation product of GlcNAc and 2-bromoacetamide (compound 18) used in the synthesis of the glycosylated (Cys (GlcNAc)-type) linker-chemerin 9 conjugate (compound 4).

ESI-MS: (m/z) calcd for $C_{135}H_{193}N_{19}O_{62}S$ $[M+2H]^{2+}$ 1553.1, $[M+3H]^{3+}$ 1035.7, found 1553.2, 1035.8.

The chemical formula of the synthesized glycosylated (Cys (asialo)-type) linker-chemerin 9 conjugate (compound 5) is shown below.

[Formula 81]

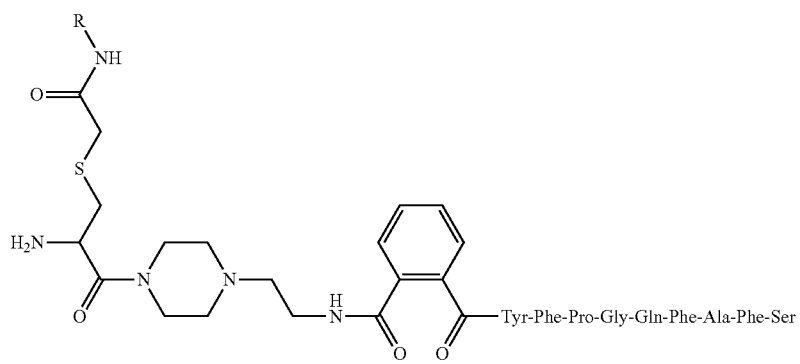

wherein R represents the following chemical formula:

[Formula 82]

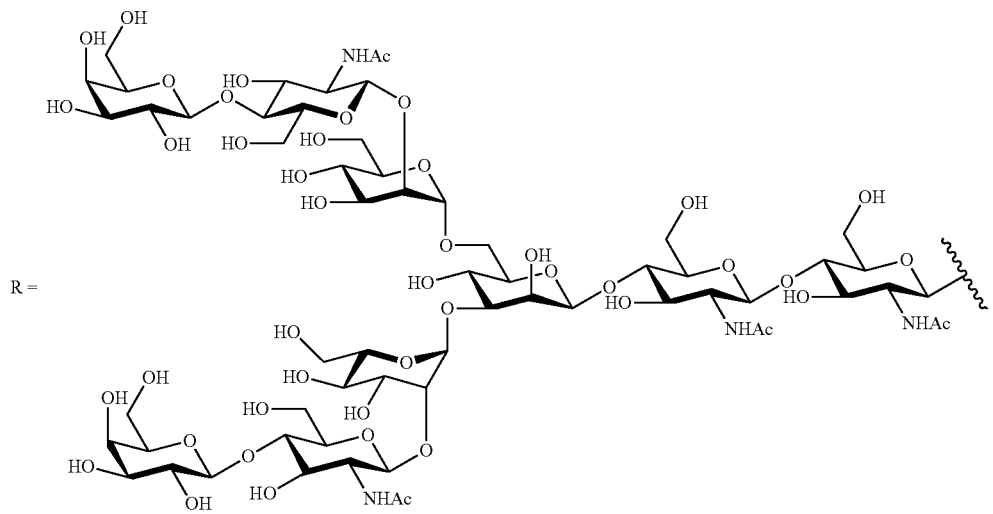

Example 6

(Synthesis of Glycosylated (Cys (Disialo)-Type) Linker-Chemerin 9 Conjugate (Compound 6))

The glycosylated (Cys (disialo)-type) linker-chemerin 9 conjugate (compound 6) (SEQ ID NO: 11) was obtained through the same reaction as in the synthesis of the glycosylated (Cys (GlcNAc)-type) linker-chemerin 9 conjugate (compound 4) in Example 4 except that a dehydration condensation product of disialo sugar chain and 2-bromoacetamide (compound 20) represented by the following chemical formula:

[Formula 83]

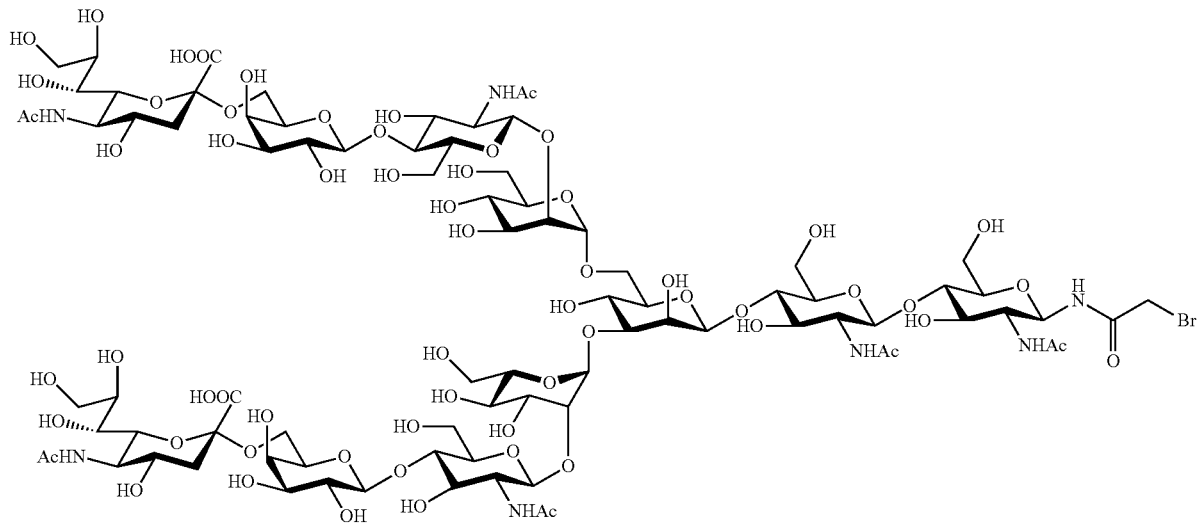

20 was used instead of the dehydration condensation product of GlcNAc and 2-bromoacetamide (compound 18) used in the synthesis of the glycosylated (Cys (GlcNAc)-type) linker-chemerin 9 conjugate (compound 4).

ESI-MS: (m/z) calcd for $C_{157}H_{227}N_{21}O_{78}S$ $[M+3H]^{3+}$ 1229.8, $[M+4H]^{4+}$ 922.6, found 1229.8, 922.6.

The chemical formula of the synthesized glycosylated (Cys (disialo)-type) linker-chemerin 9 conjugate (compound 6) is shown below.

[Formula 84]

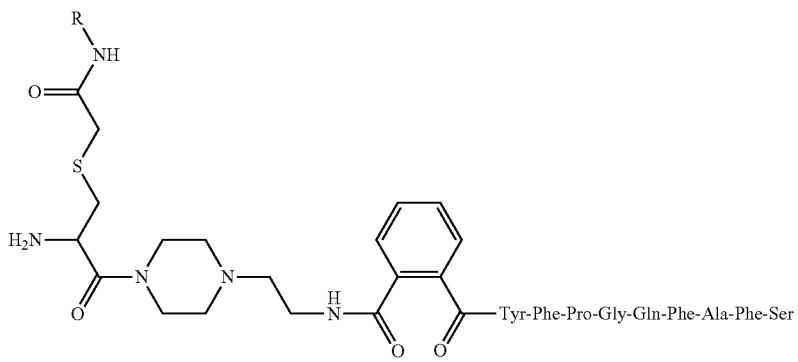

6 wherein R represents the following chemical formula:

[Formula 85]

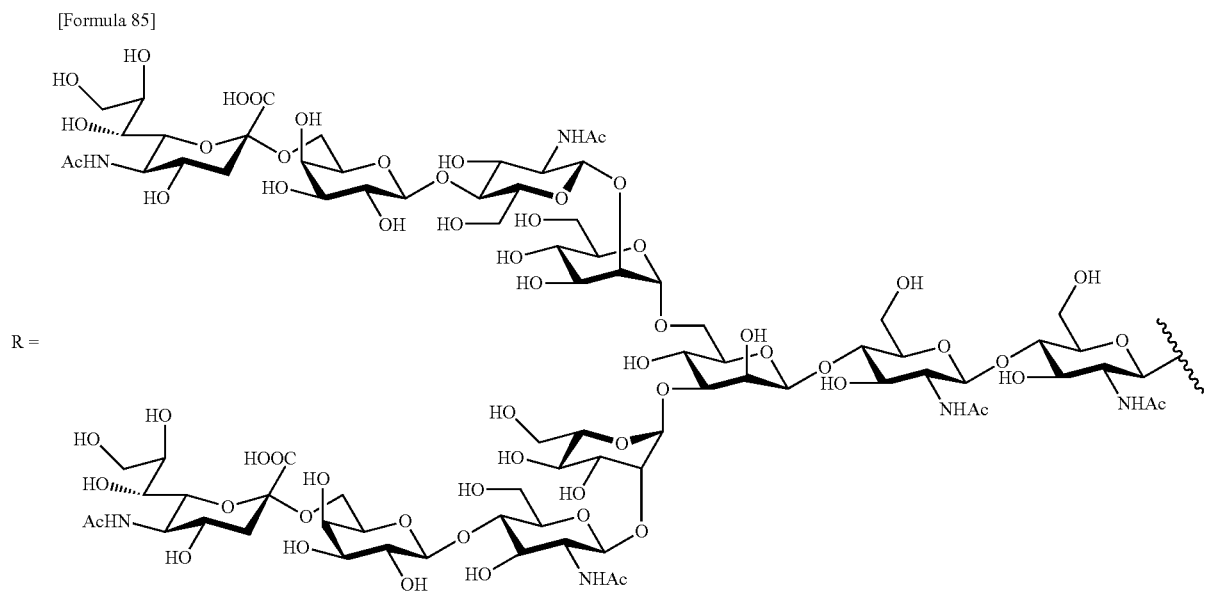

Example 7

(Synthesis of Glycosylated (Fmoc-Cys (Disialo)-Type) Linker-Chemerin 9 Conjugate (Compound 8))

The compound 16 (0.4 mg, 0.24 μmol) obtained in the course of the synthesis of the glycosylated (Cys (GlcNAc)-type) linker-chemerin 9 conjugate (compound 4) of Example 4, and the dehydration condensation product of disialo sugar chain and 2-bromoacetamide (compound 20) (0.9 mg, 0.38 μmol) also used in the synthesis of the glycosylated (Cys (disialo)-type) linker-chemerin 9 conjugate (compound 6) of Example 6 were dissolved in a 0.2 M phosphate buffer solution (pH 7.4, 56 μL) containing 7 M guanidine hydrochloride and reacted at room temperature for 2.5 hours. The reaction solution was purified by HPLC [column: SHISEIDO CAPCELL PAK C18 UG-120 (5 μm), φ4.6×250 mm, flow rate: 0.7 mL/min, eluent A: 0.1% TFA in water, eluent B: 0.09% TFA/10% water/90% acetonitrile, gradient A:B=60:40→40:60 (20 min) linear concentration gradient elution] to obtain the glycosylated (Fmoc-Cys (disialo)-type) linker-chemerin 9 conjugate (compound 8) (SEQ ID NO: 12) (0.9 mg, 0.23 μmol, yield: 96%).

ESI-MS: (m/z) calcd for $C_{172}H_{237}N_{21}O_{80}S$ $[M+3H]^{3+}$ 1303.8, $[M+4H]^{4+}$ 978.1, found 1308.8, 978.1.

The chemical formula of the synthesized glycosylated (Fmoc-Cys (disialo)-type) linker-chemerin 9 conjugate (compound 8) is shown below.

[Formula 86]

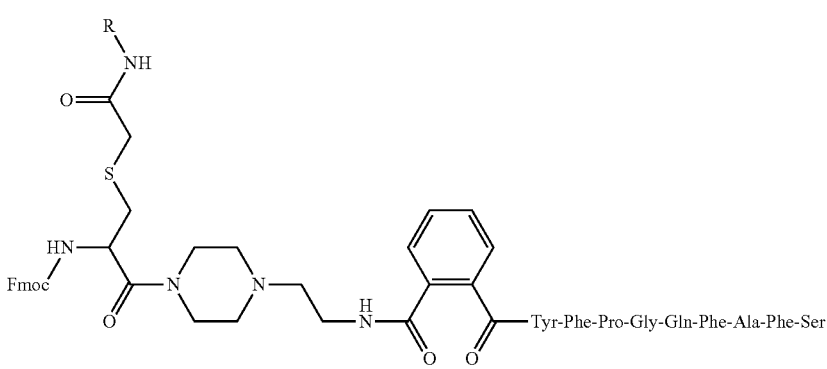

wherein R represents the following chemical formula:

[Formula 87]

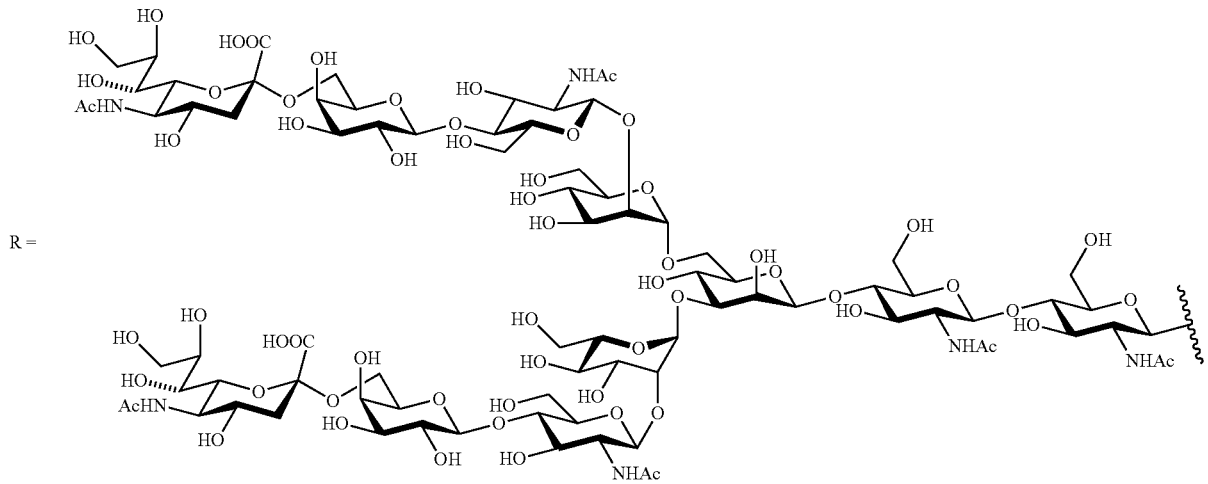

R =

Example 8

(Synthesis of Glycosylated (Ac-Asn (Asialo)-Type) Linker-Chemerin 9 Conjugate (Compound 9))

[Formula 88] Synthesized as Described in FIG. 7.

Fmoc groups in the resin (compound 15) (15 μmol) bonded to chemerin 9 protected with tBu and Trt and a linker moiety were removed by treatment with 20% piperidine in DMF. After washing with DMF, a DMF solution (375 μL) containing acetic acid (4.3 μL), HOBt (10.1 mg, 75 μmol), and DIC (11.0 μL, 71 μmol) was added thereto, and the mixture was shaken at room temperature for 1 hour for condensation operation. After washing with DMF, this condensation operation was repeated once. After washing with DMF and dichloromethane, an appropriate amount of TFA:water:triisopropylsilane:ethanedithiol (90:2.5:5:2.5, respectively, parts by volume) was added thereto, and the mixture was shaken at room temperature for 3 hours. Then, the resin was filtered off. To the filtrate, cooled diethyl ether was added to obtain the compound as precipitates. The obtained compound was purified by HPLC [column: SHISEIDO CAPCELL PAK C18 UG-120 (5 μm), φ20×250 mm, flow rate: 7.0 mL/min, eluent A: 0.1% TFA in water, eluent B: 0.09% TFA/10% water/90% acetonitrile, gradient A:B=75:25→67:33 (8 min) linear concentration gradient elution] to obtain the glycosylated (Ac-Asn (asialo)-type) linker-chemerin 9 conjugate (compound 9) (SEQ ID NO: 13) (5.0 mg).

ESI-MS: (m/z) calcd for $C_{136}H_{193}N_{19}O_{63}$ $[M+2H]^{2+}$ 1551.1, $[M+3H]^{3+}$ 1034.4, found 1551.1, 1034.4.

Example 9

(Synthesis of Glycosylated (Asn (Asialo)-Tetrachlorophthaloyl-Type) Linker-Chemerin 9 Conjugate (Compound 10))

The glycosylated (Fmoc-Asn (asialo)-type) linker-chemerin 9 conjugate (compound 7) was synthesized as described in Example 1. Then, the glycosylated (Asn (asialo)-tetrachlorophthaloyl-type) linker-chemerin 9 conjugate (compound 10) (SEQ ID NO: 14) was obtained by using tetrachlorophthalic anhydride instead of phthalic anhydride in the course of the synthesis of the glycosylated (Asn (asialo)-type) linker-chemerin 9 conjugate (compound 1) as described in Example 2.

ESI-MS: (m/z) calcd for $C_{134}H_{187}C_{14}N_{19}O_{62}$ $[M+2H]^{2+}$ 1598.0, $[M+3H]^{3+}$ 1065.7, found 1598.0, 1065.7.

The chemical formula of the synthesized glycosylated (Asn (asialo)-tetrachlorophthaloyl-type) linker-chemerin 9 conjugate (compound 10) is shown below.

[Formula 89]

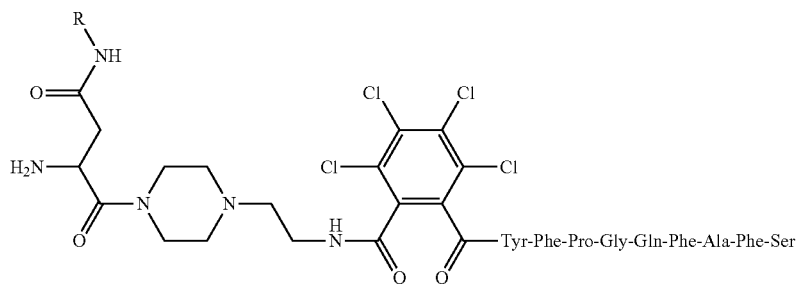

wherein R represents the following chemical formula:

[Formula 90]

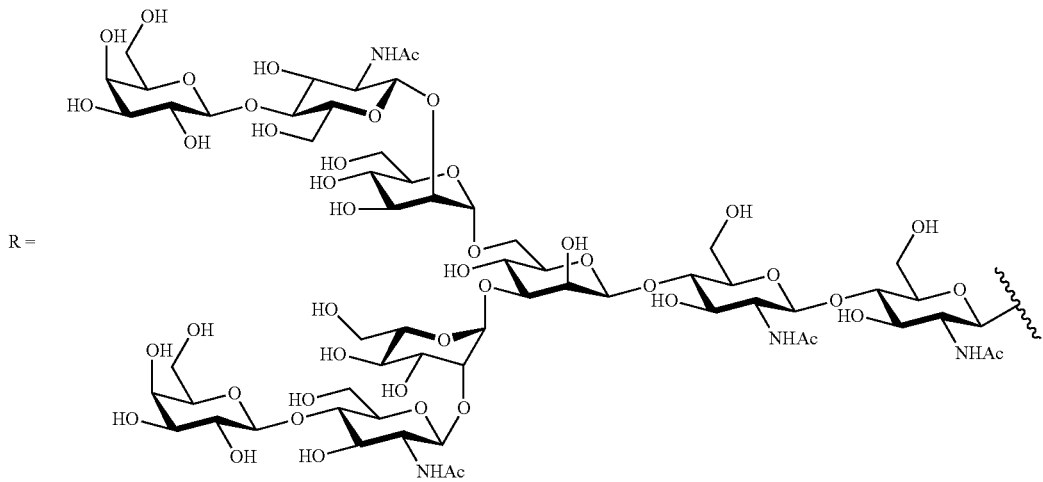

Example 10

(Cleavage Evaluation of Various Synthesized Glycosylated Linker-Chemerin 9 Conjugates)

The schematic structures of the glycosylated linker-chemerin 9 conjugates synthesized in Examples above are shown below.

[Formula 91]

(1)

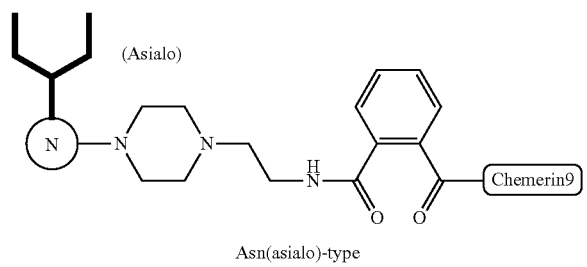

Asn(asialo)-type (4)

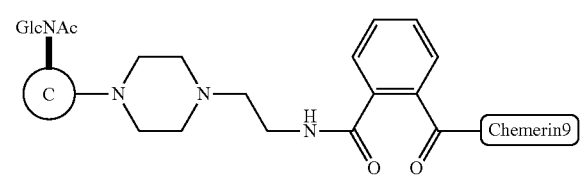

Cys(GlcNAc)-type (5)

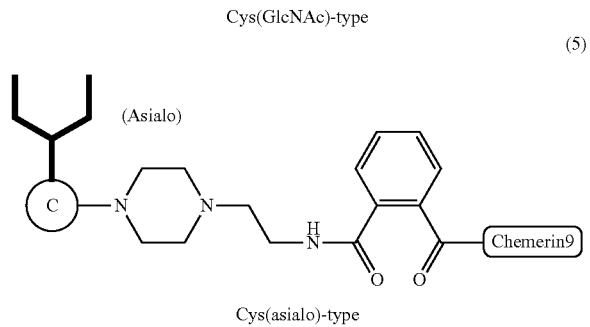

Cys(asialo)-type (6)

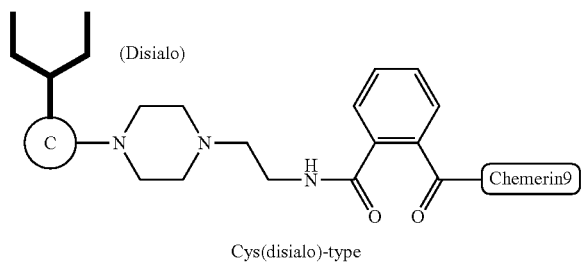

Cys(disialo)-type (7)

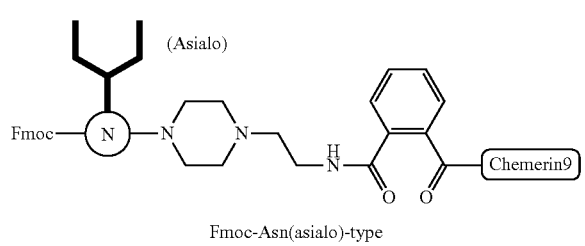

Fmoc-Asn(asialo)-type (8)

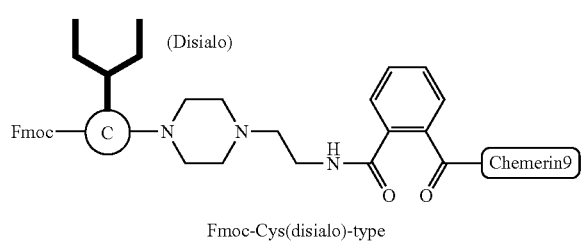

Fmoc-Cys(disialo)-type

-continued (9)

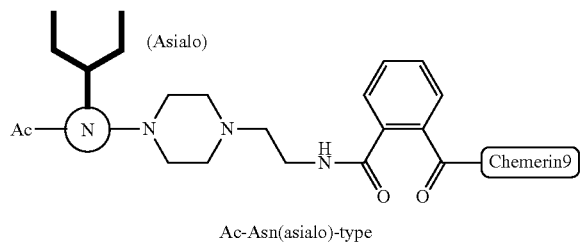

Ac-Asn(asialo)-type (10)

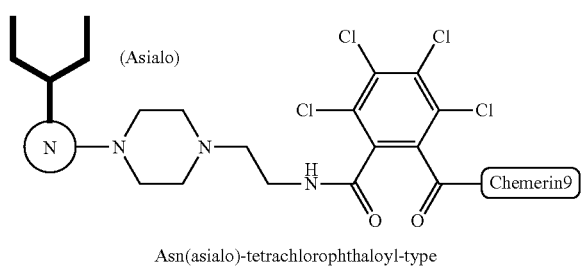

Asn(asialo)-tetrachlorophthaloyl-type wherein
Asn (asialo)-type (1) represents the glycosylated (Asn (asialo)-type) linker-chemerin 9 conjugate (compound 1),
Cys (GlcNAc)-type (4) represents the glycosylated (Cys (GlcNAc)-type) linker-chemerin 9 conjugate (compound 4),
Cys (asialo)-type (5) represents the glycosylated (Cys (asialo)-type) linker-chemerin 9 conjugate (compound 5),
Cys (disialo)-type (6) represents the glycosylated (Cys (disialo)-type) linker-chemerin 9 conjugate (compound 6),
Fmoc-Asn (asialo)-type (7) represents the glycosylated (Fmoc-Asn (asialo)-type) linker-chemerin 9 conjugate (compound 7),
Fmoc-Cys (disialo)-type (8) represents the glycosylated (Fmoc-Cys (disialo)-type) linker-chemerin 9 conjugate (compound 8),
Ac-Asn (asialo)-type (9) represents the glycosylated (Ac-Asn (asialo)-type) linker-chemerin 9 conjugate (compound 9),
Asn (asialo)-tetrachlorophthaloyl-type (10) represents the glycosylated (Asn (asialo)-tetrachlorophthaloyl-type) linker-chemerin 9 conjugate (compound 10),

[Formula 92]

represents asparagine, and the asparagine is bonded at its side chain amino group to the asialo sugar chain and bonded at its backbone carboxy group to the linker moiety, and

[Formula 93]

represents cysteine, and the cysteine is bonded at its side chain thiol group to the asialo sugar chain, disialo sugar chain, or GlcNAc via the group —$CH_2$—CONH— and bonded at its backbone carboxy group to the linker moiety.

The autocatalytic cleavage of the glycosylated linker moiety was observed for the synthesized glycosylated linker-chemerin 9 conjugates (compound 1) and (compound 4) to (compound 10). Each experiment was conducted in the same way as the method described in Example 3. As a result, all of the synthesized glycosylated linker-chemerin 9 conjugates were confirmed to release and produce the unmodified chemerin 9 in the solution. Also, the elimination half-life of each glycosylated linker-chemerin 9 conjugate was determined. The half-life is shown in the table below.

TABLE 6

Elimination half-life of synthesized glycosylated linker-chemerin 9 conjugate

| | | | Half-life | |
|---|---|---|---|---|
| Entry | Compound | Reaction temperature | Acetate buffer solution (pH 4.0) | PBS (pH 7.4) |
| 1 | Asn (asialo)-type (1) | 37° C. | 4.4 hours | 1.2 hours |
| 2 | Cys (GlcNAc)-type (4) | 37° C. | 4.3 hours | 1.4 hours |
| 3 | Cys (asialo)-type (5) | 37° C. | 4.5 hours | 1.3 hours |
| 4 | Cys (disialo)-type (6) | 37° C. | 4.8 hours | 1.4 hours |
| 5 | Fmoc-Asn (asialo)-type (7) | 37° C. | 12.2 hours | 2.6 hours |
| 6 | Fmoc-Cys (disialo)-type (8) | 37° C. | 10.5 hours | 2.5 hours |
| 7 | Ac-Asn (asialo)-type (9) | 37° C. | 12.7 hours | 1.4 hours |
| 8 | Asn (asialo)-tetrachlorophthaloyl-type (10) | 37° C. | 1.3 hours | 0.25 hours |
| 9 | Asn (asialo)-tetracholorophthaloyl-type (10) | 25° C. | 4.5 hours | 1.1 hours |

The half-lives of the Asn (asialo)-type (1) and the Cys (asialo)-type (5) were very similar hours both at pH 4.0 and at pH 7.4. From these results, the present inventor found that change in the amino acid residue added to the sugar chain does not largely influence the cleavage rate of the glycosylated linker.

The half-lives of the Cys (GlcNAc)-type (4), the Cys (asialo)-type (5), and the Cys (disialo)-type (6) were similar amounts of time to each other. From these results, the present inventor found that the size of the sugar chain in the glycosylated linker does not largely influence the cleavage efficiency of the glycosylated linker. Thus, those skilled in the art can understand that the unmodified physiologically active substance can be released and produced in vivo even by use of a glycosylated linker having a larger size.

The Fmoc-Asn (asialo)-type (7) in which the N terminus of asparagine added to the sugar chain was protected with an Fmoc group exhibited a delayed cleavage time both at pH 4.0 and at pH 7.4 compared with the Asn (asialo)-type (1) with the N terminus of the asparagine unprotected. Likewise, the Fmoc-Cys (disialo)-type (8) in which the N terminus of cysteine added to the sugar chain was protected with an Fmoc group exhibited a delayed cleavage time both at pH 4.0 and at pH 7.4 compared with the Cys (disialo)-type (6) with the N terminus of the cysteine unprotected. The Ac-Asn (asialo)-type (9) in which the N terminus of asparagine added to the sugar chain was protected with an acetyl group did not largely differ in half-life at pH 7.4 from the Asn (asialo)-type (1) with the N terminus of the asparagine unprotected, whereas its half-life at pH 4.0 was prolonged by nearly 3 times compared with the Asn (asialo)-type (1). The half-life of the Ac-Asn (asialo)-type (9) at pH 4.0 was very similar to that of the Fmoc-Asn (asialo)-type (7). From these results, the present inventor found that the protection of the N-terminal amino group of the amino acid added to the sugar chain can improve the stability of the glycosylated linker-physiologically active substance conjugate under acidic conditions (e.g., pH 4.0).

The Asn (asialo)-tetrachlorophthaloyl-type (10) had a half-life of 15.3 minutes (approximately 0.25 hours) in PBS (37° C., pH 7.4). The half-life of the Asn (asialo)-tetrachlorophthaloyl-type (10) was only approximately ⅕ of that of the Asn (asialo)-type (1) with the phthaloyl group unsubstituted by a chlorine atom. From these results, the present inventor found that the glycosylated linker moiety with the phthaloyl group replaced by a tetrachlorophthaloyl group is autocatalytically cleaved approximately 5 times faster. Without intending to be bound to any theory, this is probably because a hydrogen atom on the aromatic ring of the phthaloyl group was replaced by an electron-withdrawing chlorine atom so that the electron density of carbonyl carbon bonded to the peptide was decreased, resulting in susceptibility to nucleophilic attack by nitrogen. Those skilled in the art understand that by the exploitation of such structural properties of the compound, the compound is applicable to a physiologically active substance desired to immediately exert its activity after administration to an organism.

The half-life of the Asn (asialo)-tetrachlorophthaloyl-type (10) in an aqueous solution was 15.3 minutes (approximately 0.25 hours) in PBS (37° C., pH 7.4) and, on the other hand, was 4.5 hours in an acetate buffer solution (25° C., pH 4.0). From this difference in half-life, it should be understood that the compound comprising a glycosylated linker moiety and a physiologically active substance moiety according to the present invention can be prepared at pH 4.0 and room temperature (e.g., 25° C.) and then administered into an organism (e.g., pH 7.4, for example, 37° C.), thereby releasing and producing the unmodified physiologically active substance immediately and controllably.

Example 11

(Cleavage Evaluation of Glycosylated Linker Moiety of Glycosylated Linker-Chemerin 9 Conjugate in Emulsion)

When an antigen solution was mixed with an emulsion and administered as a vaccine to an organism, the effects of allowing the antigen to remain at the vaccination site and to be sustained-released can be expected. Thus, the applicability of the compound comprising a glycosylated linker moiety and a physiologically active substance moiety or the salt thereof according to the present invention to the development of various vaccines such as peptide vaccines was studied by examining whether the glycosylated linker moiety according to the present invention was self-cleaved from the compound comprising a glycosylated linker moiety and a physiologically active substance moiety or the salt thereof not only in an aqueous solution but in an emulsion. The stability of the compound comprising a glycosylated linker moiety and a physiologically active substance moiety or the salt thereof according to the present invention was compared between in an emulsion prepared from the aqueous solution and in an acetate buffer solution as follows:

The freeze-dried glycosylated (Asn (asialo)-type) linker-chemerin 9 conjugate (compound 1) was dissolved in a 0.1 M acetate buffer solution (pH 4.0, 25° C., 175 µL). To the acetate buffer solution, 175 µL of a mineral oil adjuvant MONTANIDE ISA 206 VG (manufactured by SEPPIC) was then added. Subsequently, the mixture was vigorously stirred by vortex to form an emulsion. The emulsion was left standing at 37° C. for incubation. Then, a 28 µL aliquot of the emulsion solution of the glycosylated (Asn (asialo)-type) linker-chemerin 9 conjugate (compound 1) was injected at given time intervals and analyzed by HPLC, by which the cleavage reaction of the glycosylated linker moiety was traced over time.

For a control group, the freeze-dried glycosylated (Asn (asialo)-type) linker-chemerin 9 conjugate (compound 1) was dissolved in a 0.1 M acetate buffer solution (25° C., pH 4.0, 350 µL) and then left standing at 37° C. for incubation. Then, a 28 µL aliquot of the acetate buffer solution of the glycosylated (Asn (asialo)-type) linker-chemerin 9 conjugate (compound 1) was injected at given time intervals and analyzed by HPLC.

From the HPLC chromatogram and ESI-MS analysis, the cleavage of the glycosylated linker moiety was confirmed to also proceed with time in the emulsion to release the unmodified chemerin 9.

For each of the emulsion solution and the acetate buffer solution, the area of the peak corresponding to the glycosylated (Asn (asialo)-type) linker-chemerin 9 conjugate (compound 1) in the HPLC chromatogram was plotted against incubation time to calculate the relative concentration vs. incubation time of the glycosylated (Asn (asialo)-type) linker-chemerin 9 conjugate (compound 1), followed by comparison (FIG. 4). As a result, the cleavage of the glycosylated linker moiety was confirmed to proceed in the emulsion at the same rate as that in the buffer solution.

Thus, those skilled in the art understand that the unmodified physiologically active substance can also be released in the emulsion prepared from the aqueous solution at the same rate as that in the aqueous solution by use of the physiologically active substance derivative having the glycosylated linker moiety according to the present invention. The results described above demonstrated that the glycosylated linker moiety according to the present invention can be applied to the utilization of the physiologically active substance as a vaccine.

Example 12

(Synthesis of Glycosylated (Asn (Asialo)-Type) Linker-HER2$_{8-16}$ Conjugate (Compound 11), Cleavage Evaluation of Glycosylated Linker Moiety, and Solubility Evaluation)

As mentioned above, the physiologically active substance derivative having the glycosylated linker moiety according to the present invention can be used even in the form of an emulsion and can therefore be applied to the development of various vaccines. Thus, the present inventor prepared a conjugate of HER2$_{8-16}$, which may also be used as a tumor antigen peptide, and a glycosylated linker as an example. In this context, HER2$_{8-16}$ (sequence: RWGLLLALL) is a peptide corresponding to the 8th to 16th amino acid residues in the amino acid sequence of the HER2/neu protein, a member of the HER (human epidermal growth factor receptor) family. HER2$_{8-16}$, also called code HE1, has the ability to bind to HLA-A24, one of HLA (human leukocyte antigen) molecules, and can induce cytotoxic T lymphocyte (CTL) by HLA-mediated antigen presentation. This peptide has therefore been identified as a tumor vaccine candidate peptide (see e.g., International Publication No. WO 2005/007694).

(Synthesis of Glycosylated (Asn (Asialo)-Type) Linker-HER2$_{8-16}$ Conjugate (Compound 11))

The present inventor synthesized a compound composed of an asialo sugar chain-attached linker and a peptide (glycosylated (Asn (asialo)-type) linker-HER2$_{8-16}$ conjugate (compound 11)) having the following schematic structure:

[Formula 94]

11

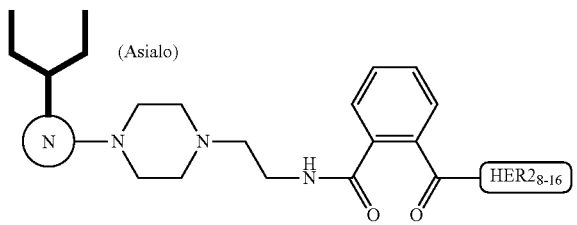

wherein

[Formula 95]

is as defined above.

Amino-PEGA resin (200 μmol) was placed in a column for solid-phase synthesis and washed with DMF. A DMF (5.0 mL) solution containing HMPB (120.2 mg, 0.500 mmol), TBTU (160.6 mg, 0.500 mmol), and N-ethylmorpholine (57.3 μL, 0.495 mmol) was added thereto, and the mixture was shaken at room temperature for 3 hours. After washing with DMF and dichloromethane, a dichloromethane (5 mL) solution containing Fmoc-Leu-OH (176.7 mg, 0.500 mmol), MSNT (148.2 mg, 0.500 mmol), and N-methylimidazole (27.9 μL, 0.35 mmol) was added to an aliquot (100 μmol) of the obtained resin, and the mixture was shaken at room temperature for 3 hours. After washing with dichloromethane and DMF, DMF (4 mL), pyridine (1.2 mL), and acetic anhydride (189 μL, 2.00 mmol) were added thereto sequentially, and the mixture was shaken at room temperature. After 1 hour, the resin was washed with DMF and dichloromethane.

The Fmoc groups were removed by treatment with 20% piperidine in DMF for 15 minutes. After washing with DMF, a protected HER2$_{8-16}$ peptide (SEQ ID NO: 16) bonded to the resin as represented by the formula (21) given below was synthesized by a solid-phase peptide synthesis method according to the Fmoc method using a Prelude (trademark) peptide synthesizer. The condensation reaction was carried out in DMF using HCTU as a condensing agent.

[Formula 96]

21

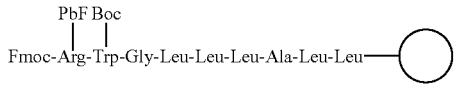

HMPB-PEGA resin

Fmoc groups in an aliquot (50 μmol) of the obtained resin (compound 21) were removed by treatment with 20% piperidine in DMF for 20 minutes to obtain a resin bonded to a protected peptide. After washing with DMF and dichloromethane, phthalic anhydride (75.7 mg, 0.511 mmol), dichloromethane (1.5 mL), and pyridine (90 μL) were added thereto sequentially, and the mixture was shaken at room temperature for 3 hours. After washing with dichloromethane and DMF, a DMF (1.25 mL) solution of HOBt (33.8 mg, 0.25 mmol) and DIC (36.6 μL, 0.238 mmol) were added thereto, and the mixture was shaken at room temperature. After 15 minutes, N-(2-aminoethyl)piperazine (330 μL, 2.51 mmol) was added thereto, and the mixture was shaken at room temperature for 1 hour. After washing with DMF, Fmoc-Asn (asialo)-OH (compound 14) (186 mg, 94.1 μmol) represented by the following chemical formula:

[Formula 97]

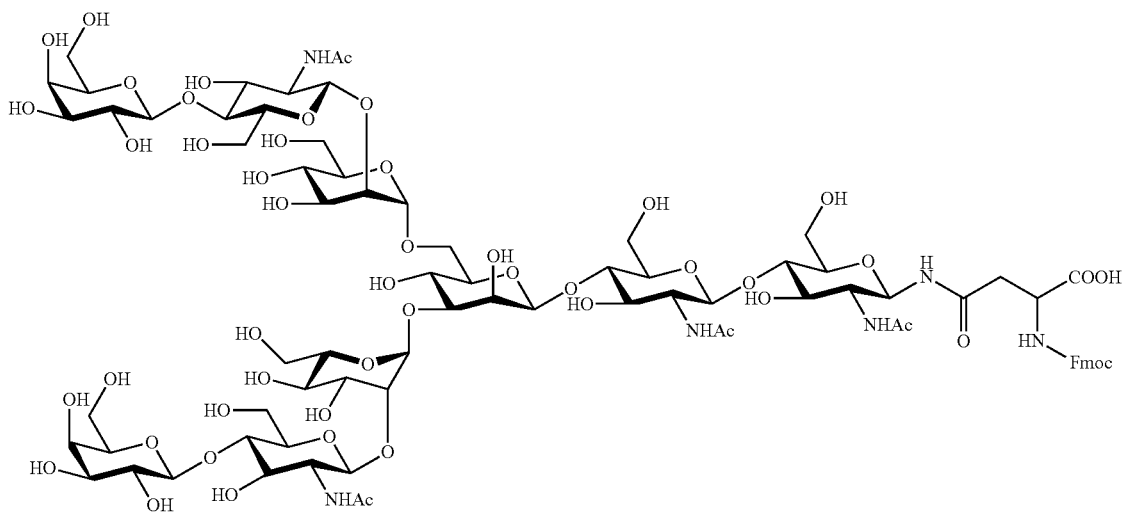

14 a DMSO-DMF (1/1, v/v, 2.1 mL) solution, TBTU (40.5 mg, 0.126 mmol), and DIPEA (33 μL, 0.19 mmol) were added thereto sequentially, and the mixture was shaken at room temperature for 12 hours. After washing with DMF, dichloromethane, and DMF sequentially, Fmoc groups were removed by treatment with 20% piperidine in DMF for 15 minutes. After washing with DMF and dichloromethane, TFA:water:triisopropylsilane:ethanedithiol (90:2.5:5:2.5, respectively, parts by volume) was added to the resin, and the mixture was shaken at room temperature for 3 hours. To the filtrate, cooled diethyl ether was added to obtain the compound as precipitates. The compound was purified by HPLC [column: SHISEIDO CAPCELL PAK C18 UG-120 (5 μm), ϕ20×250 mm, flow rate: 7.0 mL/min, eluent A: 0.1% TFA in water, eluent B: 0.09% TFA/10% water/90% acetonitrile, gradient A:B=60:40→55.5:44.5 (11 min) linear concentration gradient elution] to obtain the glycosylated (Asn (asialo)-type) linker-HER2$_{8-16}$ conjugate (compound 11) (SEQ ID NO: 17) (11.1 mg).

ESI-MS: (m/z) calcd for $C_{132}H_{212}N_{22}O_{59}$ [M+2H]$^{2+}$ 1525.7, [M+3H]$^{3+}$ 1017.5, [M+4H]$^{4+}$ 763.4, found 1525.7, 1017.5, 763.4.

The chemical formula of the synthesized glycosylated (Asn (asialo)-type) linker-HER2$_{8-16}$ conjugate (compound 11) is shown below.

[Formula 98]

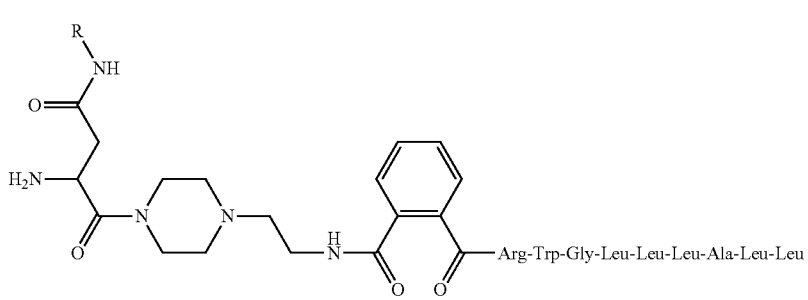

11 wherein R represents the following chemical formula:

[Formula 99]

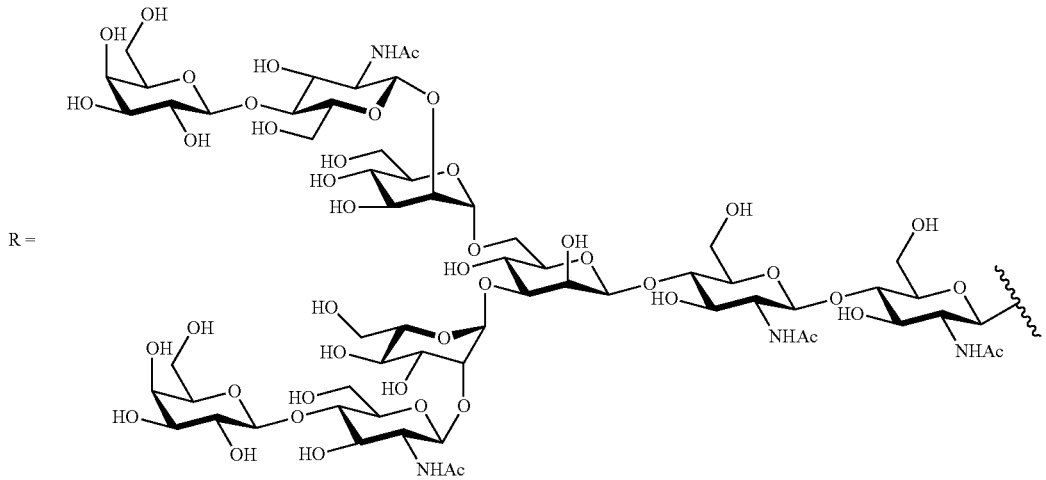

R =

(Cleavage Evaluation of Glycosylated Linker Moiety of Glycosylated (Asn (Asialo)-Type) Linker-HER2$_{8-16}$ Conjugate (Compound 11) in Aqueous Solution)

Subsequently, the autocatalytic cleavage behavior of the glycosylated linker moiety in an aqueous solution was traced for the obtained glycosylated (Asn (asialo)-type) linker-HER2$_{8-16}$ conjugate (compound 11).

The cleavage behavior was traced in the same way as the method described in Example 3. Specifically, the freeze-dried glycosylated (Asn (asialo)-type) linker-HER2$_{8-16}$ conjugate (compound 11) was dissolved in PBS (pH 7.4) or a 0.1 M acetate buffer solution (pH 4.0) and then left standing at 25° C. or 37° C. for incubation. Then, a given amount of the PBS solution or the 0.1 M acetate buffer solution containing the glycosylated (Asn (asialo)-type) linker-HER2$_{8-16}$ conjugate (compound 11) dissolved therein was injected at given time intervals and analyzed by HPLC. From the HPLC chromatogram and ESI-MS analysis, the cleavage of the glycosylated linker moiety was confirmed to proceed with time in the aqueous solution to produce the unmodified HER2$_{8-16}$ (SEQ ID NO: 15). The elimination half-life of the glycosylated (Asn (asialo)-type) linker-HER2$_{8-16}$ conjugate (compound 11) under various conditions is shown in the table below.

TABLE 7

Elimination half-life of glycosylated linker-HER2$_{8-16}$ conjugate (compound 11) under various conditions

| Entry | Solvent | | Temperature | Half-life |
|---|---|---|---|---|
| 1 | Acetate buffer solution | (pH 4.0) | 37° C. | 6.2 hours |
| 2 | Acetate buffer solution | (pH 4.0) | 25° C. | 21.4 hours |
| 3 | PBS | (pH 7.4) | 37° C. | 2.6 hours |
| 4 | PBS | (pH 7.4) | 25° C. | 8.3 hours |

In the comparison of the half-life at the same temperature, the glycosylated linker moiety was found to be cleaved faster at a higher pH (comparison between Entries 1 and 3 (37° C.), and comparison between Entries 2 and 4 (25° C.)). In the comparison of the half-life at the same pH, the glycosylated linker moiety was found to be cleaved faster at a higher temperature (comparison between Entries 1 and 2 (pH 4.0), and comparison between Entries 3 and 4 (pH 7.4)).

From these results, the present inventor found that the cleavage of the glycosylated linker moiety is promoted with increase in (i) temperature and (ii) pH, as with the results observed for the glycosylated linker-chemerin 9 conjugate.

Thus, considering the results of Tables 5 to 7 together, those skilled in the art understand that the physiologically active substance having the glycosylated linker moiety according to the present invention can produce the unmodified physiologically active substance by the cleavage of the glycosylated linker moiety in a manner dependent on temperature and/or pH.

(Solubility Evaluation of Glycosylated (Asn (Asialo)-Type) Linker-HER2$_{8-16}$ Conjugate (Compound 11))

A water solubility-improving effect was evaluated in the case of using the physiologically active substance derivative having the glycosylated linker moiety according to the present invention. HER2$_{8-16}$ was used as an example of the physiologically active substance.

The glycosylated linker-HER2$_{8-16}$ conjugate (compound 11) and the HER2$_{8-16}$ peptide were placed in amounts of approximately 3.5 mg and 3.5 mg, respectively, into separate microtubes. To each microtube, 30 μL of a 0.1% aqueous TFA solution was added. These microtubes were shaken at 25° C. for 15 minutes and then centrifuged at 16100×g at 25° C. for 10 minutes. Subsequently, the absorbance of the supernatant at 280 nm was measured in each of these microtubes. From the obtained values, the respective concentrations of the glycosylated linker-HER2$_{8-16}$ conjugate (compound 11) and the HER2$_{8-16}$ peptide were calculated to determine solubility.

In this context, the molar absorption coefficient of the glycosylated linker-HER2$_{8-16}$ conjugate (compound 11) at 280 nm was determined by the following method: the solution of the compound 11 was dispensed in equal amounts into five tubes and freeze-dried. Then, three of these tubes were used in amino acid composition analysis to determine sample contents. Also, to one of the five tubes, 1 mL of a 0.1% aqueous TFA solution was added, and the absorbance of the glycosylated linker-HER2$_{8-16}$ conjugate (compound 11) at 280 nm was measured for this tube. This absorbance at 280 nm was divided by the concentration determined in the amino acid composition analysis to determine the molar absorption coefficient. As a result, the molar absorption coefficient $\epsilon_M$ of the glycosylated linker-HER2$_{8\text{-}16}$ conjugate (compound 11) at 280 nm was 5922.

The molar absorption coefficient $\epsilon_M$ of the HER2$_{8\text{-}16}$ peptide (SEQ ID NO: 15) at 280 nm was calculated according to the following expression (C. N. Pace et al., Prot. Sci., 1995, 4, pp. 2411-2423):

$$\epsilon_M = \text{Trp} \times 5500 + \text{Tyr} \times 1490 + \text{Cystine} \times 125 \, [A_{280}/\text{mol/cm}]$$

wherein Trp represents the number of tryptophan residues, Tyr represents the number of tyrosine residues, and Cystine represents the number of disulfide bonds. Since the HER2$_{8\text{-}16}$ peptide (amino acid sequence: RWGLLLALL) contained one tryptophan residue, its molar absorption coefficient $\epsilon_M$ at 280 nm was 5500.

As a result, the HER2$_{8\text{-}16}$ peptide unbound with the glycosylated linker had a solubility of 0.21 mg/mL ($2.0 \times 10^2$ μM)) in the 0.1% aqueous TFA solution. In this respect, the precipitation of the HER28-16 peptide was able to be visually confirmed in the microtube. On the other hand, the glycosylated (Asn (asialo)-type) linker-HER2$_{8\text{-}16}$ conjugate (compound 11) was confirmed to have a solubility of 100 mg/mL or higher in the 0.1% aqueous TFA solution. Surprisingly, the precipitation of the glycosylated (Asn (asialo)-type) linker-HER2$_{8\text{-}16}$ conjugate (compound 11) was unable to be confirmed even at a concentration of 116 mg/mL ($3.8 \times 10^4$ μM). These results demonstrated that, surprisingly, the water solubility of the HER2$_{8\text{-}16}$ peptide is improved by 190 or more times in terms of molar concentration by the bonding of the glycosylated (Asn (asialo)-type) linker of the present invention.

TABLE 8

| Comparison of solubility between presence and absence of glycosylated linker | | |
|---|---|---|
| Entry | Compound | Solubility[a] |
| 1 | HER2$_{8\text{-}16}$ | 0.21 mg/mL ($2.0 \times 10^2$ μM) |
| 2 | Glycosylated linker-HER2$_{8\text{-}16}$ conjugate (compound 11) | >116 mg/mL (>$3.8 \times 10^4$ μM) |

[a]Solvent: 0.1% aqueous TFA solution

Thus, the present inventor found the solubility in an aqueous solution or an emulsion can be significantly improved as compared with the unmodified physiologically active substance by use of the compound comprising a glycosylated linker moiety and a physiologically active substance moiety or the salt thereof according to the present invention.

The invention claimed is:
1. A compound comprising a glycosylated linker moiety and a physiologically active substance moiety, or a salt thereof, the compound being represented by the following formula (A):

wherein the $R^1$ is represented by the following formula (IV):

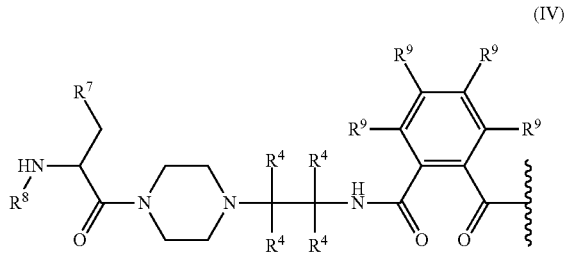

in the formula (IV),
each $R^4$ independently represents a hydrogen atom, an alkyl group having 1 to 16 carbon atoms, or an aryl group having 5 to 16 carbon atoms;
$R^7$ represents —S—$CH_2$—CONH-sugar chain or —CONH-sugar chain;
$R^8$ represents a hydrogen atom, an acyl group having 1 to 16 carbon atoms, an Fmoc group, a Boc group, a Z group, a Troc group, an Alloc group, a carbamate protective group, a sugar chain, an amino acid, a polypeptide, a glycosylated amino acid, or a glycosylated polypeptide;
each $R^9$ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group; and
the wavy line represents a binding site to X;
X represents the physiologically active substance moiety, the physiologically active substance has at least one amino group; and
the bonding of the X to the $R^1$ is a bond at the at least one amino group.
2. The compound or salt thereof according to claim 1, wherein all of the four $R^4$ moieties are hydrogen atoms.
3. The compound or salt thereof according to claim 1, wherein at least one of the $R^9$ moieties is halogen.
4. The compound or salt thereof according to claim 1, wherein all of the four $R^9$ moieties are chlorine atoms.
5. The compound or salt thereof according to claim 1, wherein the sugar chain in the "glycosylated amino acid or glycosylated polypeptide" is bonded to Asn or Cys in the amino acid or the polypeptide.
6. The compound or salt thereof according to claim 1, wherein the sugar chain in the "glycosylated amino acid or glycosylated polypeptide" is bonded to the amino acid or the polypeptide without the mediation of a linker.
7. The compound or salt thereof according to claim 1, wherein the sugar chain in the "sugar chain, glycosylated amino acid, or glycosylated polypeptide" consists of 4 or more sugar residues.
8. The compound or salt thereof according to claim 1, wherein the sugar chain in the "sugar chain, glycosylated amino acid, or glycosylated polypeptide" is a biantennary complex-type sugar chain, a triantennary complex-type sugar chain, or a tetraantennary complex-type sugar chain.
9. The compound or salt thereof according to claim 8, wherein the sugar chain is a biantennary complex-type sugar chain selected from the group consisting of a disialo sugar chain, a monosialo sugar chain, an asialo sugar chain, a di-GlcNAc sugar chain, and a dimannose sugar chain.
10. The compound or salt thereof according to claim 1, wherein
the sugar chain in the "sugar chain, glycosylated amino acid, or glycosylated polypeptide" is a sugar chain represented by the following formula:

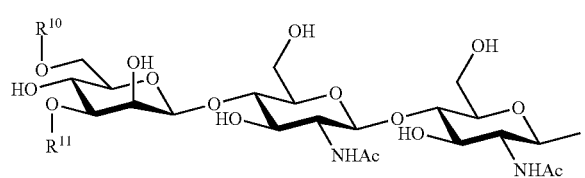

wherein
$R^{10}$ and $R^{11}$ are the same or different and each represent

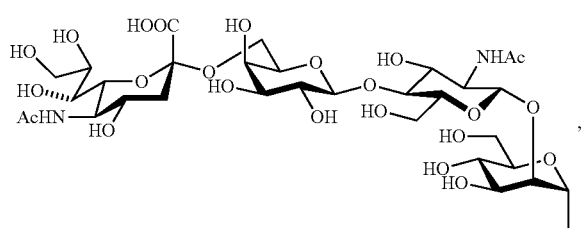

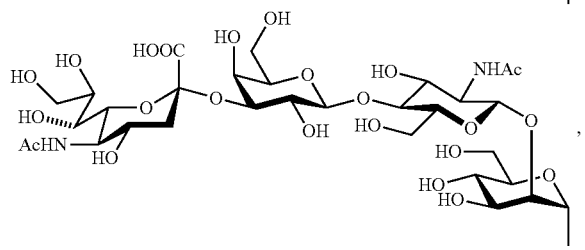

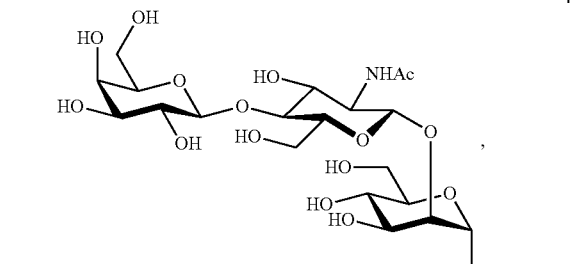

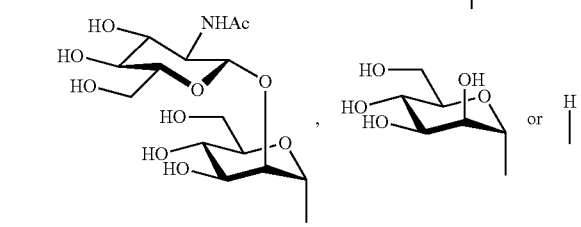

and Ac represents an acetyl group.
11. The compound or salt thereof according to claim 1, wherein the physiologically active substance is a low molecular-weight physiologically active substance, or a biopolymer.

12. The compound or salt thereof according to claim 11, wherein the biopolymer is selected from the group consisting of a protein, a polypeptide, a polynucleotide, and a peptide nucleic acid.

13. The compound or salt thereof according to claim 1, wherein the compound or the salt thereof has improved water solubility compared with an unmodified physiologically active substance.

14. The compound or salt thereof according to claim 13, wherein the improved water solubility is 10 to 1,000,000 times the water solubility of the "unmodified physiologically active substance" in terms of molar concentration.

15. The compound or salt thereof according to claim 1, wherein the glycosylated linker moiety is capable of being autocatalytically cleaved in a manner dependent on pH and/or temperature.

16. A composition comprising a compound or salt thereof according to claim 1, wherein sugar chains in the compound or the salt thereof are substantially homogeneous.

17. A pharmaceutical composition comprising
(I) a compound or salt thereof according to claim 1, and
(II) a pharmacologically acceptable carrier.

18. The pharmaceutical composition according to claim 17, wherein the physiologically active substance immediately exerts its activity after administration to a subject.

19. A method of vaccination comprising administering to a subject the pharmaceutical composition according to claim 17.

20. A method for producing a compound comprising a glycosylated linker moiety and a physiologically active substance moiety, or a salt thereof, the compound being represented by the following formula (A):

R¹—X  (A)

wherein X represents the physiologically active substance moiety, and the physiologically active substance comprises a peptide moiety having at least one amino group, hydroxy group, thiol group, or carboxy group,
the production method comprising:
(a) synthesizing the peptide moiety on a resin by a solid-phase synthesis method; and
(b) bonding a linker moiety represented by the following formula (IV) to the "amino group, hydroxy group, thiol group, or carboxy group" in the peptide moiety synthesized in the step (a):
wherein R¹ is represented by the following formula (IV):

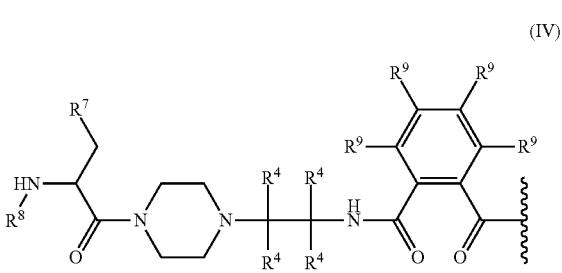

(IV)

in the formula (IV),
each R⁴ independently represents a hydrogen atom, an alkyl group having 1 to 16 carbon atoms, or an aryl group having 5 to 16 carbon atoms;
R⁷ represents —S—CH₂—CONH-sugar chain or —CONH-sugar chain;
R⁸ represents a hydrogen atom, an acyl group having 1 to 16 carbon atoms, an Fmoc group, a Boc group, a Z group, a Troc group, an Alloc group, a carbamate protective group, a sugar chain, an amino acid, a polypeptide, a glycosylated amino acid, or a glycosylated polypeptide;
each R⁹ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group; and
the wavy line represents a binding site to the "amino group, hydroxy group, thiol group, or carboxy group" in the peptide moiety.

21. A compound or a salt thereof obtainable by a production method according to claim 20.

22. A method for producing a compound comprising a glycosylated linker moiety and a physiologically active substance moiety, or a salt thereof, the compound being represented by the following formula (A):

R¹—X  (A)

wherein X represents the physiologically active substance moiety, and the physiologically active substance comprises a peptide moiety having at least one amino group, hydroxy group, thiol group, or carboxy group,
the production method comprising bonding a glycosylated linker represented by the following formula (IV) to the "amino group, hydroxy group, thiol group, or carboxy group" in the peptide moiety by dehydration condensation;
wherein R¹ is represented by the following formula (IV):

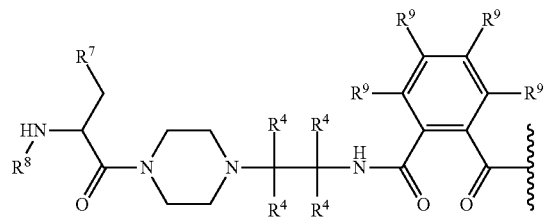

(IV)

in the formula (IV),
each R⁴ independently represents a hydrogen atom, an alkyl group having 1 to 16 carbon atoms, or an aryl group having 5 to 16 carbon atoms;
R⁷ represents —S—CH₂—CONH-sugar chain or —CONH-sugar chain;
R⁸ represents a hydrogen atom, an acyl group having 1 to 16 carbon atoms, an Fmoc group, a Boc group, a Z group, a Troc group, an Alloc group, a carbamate protective group, a sugar chain, an amino acid, a polypeptide, a glycosylated amino acid, or a glycosylated polypeptide;
each R⁹ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group; and
the wavy line represents a binding site to the "amino group, hydroxy group, thiol group, or carboxy group" in the peptide moiety.

23. A compound or a salt thereof obtainable by a production method according to 22.

24. A glycosylated linker for bonding to a physiologically active substance having at least one amino group, hydroxy group, thiol group, or carboxy group, the glycosylated linker being represented by the following formula (B):

R¹-L     (B)

wherein $R^1$ is represented by the following formula (IV):

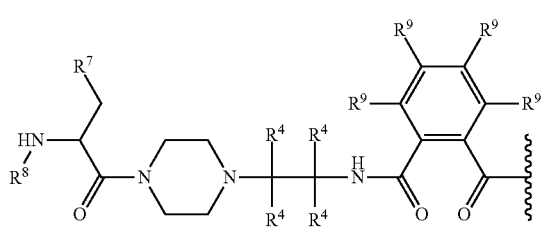

(IV)

in the formula (IV), each $R^4$ independently represents a hydrogen atom, an alkyl group having 1 to 16 carbon atoms, or an aryl group having 5 to 16 carbon atoms;

$R^7$ represents —S—CH$_2$—CONH-sugar chain or —CONH-sugar chain;

$R^8$ represents a hydrogen atom, an acyl group having 1 to 16 carbon atoms, an Fmoc group, a Boc group, a Z group, a Troc group, an Alloc group, a carbamate protective group, a sugar chain, an amino acid, a polypeptide, a glycosylated amino acid, or a glycosylated polypeptide;

each $R^9$ independently represents a hydrogen atom, halogen, a cyano group, an alkyl group having 1 to 4 carbon atoms, an alkoxy group having 1 to 4 carbon atoms, a nitro group, a mesyl group, a tosyl group, an acyl group having 1 to 3 carbon atoms, a hydroxy group, a carboxy group, or an amino group;

the wavy line represents a binding site to L; and

L represents a leaving group.

* * * * *